US011123321B2

(12) United States Patent
Geisser et al.

(10) Patent No.: US 11,123,321 B2
(45) Date of Patent: *Sep. 21, 2021

(54) AQUEOUS IRON CARBOHYDRATE COMPLEXES, THEIR PRODUCTION AND MEDICAMENTS CONTAINING THEM

(71) Applicant: VIFOR (INTERNATIONAL) AG, St. Gallen (CH)

(72) Inventors: Peter Geisser, St. Gallen (CH); Erik Philipp, Arbon (CH); Walter Richie, Gossau (CH)

(73) Assignee: VIFOR (INTERNATIONAL) AG, St. Gallen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/132,652

(22) Filed: Dec. 23, 2020

(65) Prior Publication Data

US 2021/0115163 A1    Apr. 22, 2021

Related U.S. Application Data

(60) Continuation of application No. 16/389,234, filed on Apr. 19, 2019, which is a continuation of application No. 13/835,400, filed on Mar. 15, 2013, now Pat. No. 10,519,252, which is a continuation of application No. 13/556,733, filed on Jul. 24, 2012, now Pat. No. 9,376,505, which is a continuation of application No. 12/581,212, filed on Oct. 19, 2009, now abandoned, which is a division of application No. 10/531,895, filed as application No. PCT/EP03/11596 on Oct. 20, 2003, now Pat. No. 7,612,109.

(30) Foreign Application Priority Data

Oct. 23, 2002    (DE) .................. 10249552.1

(51) Int. Cl.
| | | |
|---|---|---|
| *A61K 31/295* | (2006.01) | |
| *A61P 7/06* | (2006.01) | |
| *A61K 31/718* | (2006.01) | |
| *A61K 33/26* | (2006.01) | |
| *A61K 47/61* | (2017.01) | |
| *A61K 45/06* | (2006.01) | |
| *C08B 31/18* | (2006.01) | |
| *C08B 30/18* | (2006.01) | |
| *C08B 37/00* | (2006.01) | |

(52) U.S. Cl.
CPC .......... *A61K 31/295* (2013.01); *A61K 31/718* (2013.01); *A61K 33/26* (2013.01); *A61K 45/06* (2013.01); *A61K 47/61* (2017.08); *A61P 7/06* (2018.01); *C08B 30/18* (2013.01); *C08B 31/185* (2013.01); *C08B 37/0009* (2013.01); *Y10S 514/814* (2013.01)

(58) Field of Classification Search
None
See application file for complete search history.

(56) References Cited

U.S. PATENT DOCUMENTS

| | | |
|---|---|---|
| 1,129,307 A | 2/1915 | Marsh |
| 2,807,610 A | 9/1957 | Zief et al. |
| 3,065,138 A | 11/1962 | Lynch |
| 3,076,798 A | 2/1963 | Mueller et al. |
| 3,086,009 A | 4/1963 | Zuschek et al. |
| 3,100,202 A | 8/1963 | Miller et al. |
| 3,151,107 A | 9/1964 | Heckel et al. |
| 3,324,109 A | 6/1967 | Eichel et al. |
| 3,536,696 A | 10/1970 | Alsop et al. |
| 3,574,184 A | 4/1971 | Alsop et al. |
| 3,591,616 A | 7/1971 | Baldt |
| 3,592,889 A | 7/1971 | Lindvall et al. |
| 3,639,588 A | 2/1972 | Alsop et al. |
| 3,821,192 A | 6/1974 | Montgomery et al. |
| 3,886,267 A | 5/1975 | Dahlberg et al. |

(Continued)

FOREIGN PATENT DOCUMENTS

| | | |
|---|---|---|
| CA | 623411 | 4/1961 |
| CA | 2195283 | 7/1998 |

(Continued)

OTHER PUBLICATIONS

Plaintiffs' Reply Brief in Support of Motion for Judicial Correction. United States District Court. District of New Jersey. Civil Action No. 19-13955 (FLW) (DEA) (CONSOLIDATED) *Vifor (International) AG and American Regent, Inc.*, Plaintiffs v. *MYLAN Laboratories Ltd. and Sandoz Inc.*, Defendants. Dated Nov. 13, 2020. 15 pages.

Reply Declaration of Brian M. Stoltz, Ph.D. In Support of Plaintiffs' Motion for Judicial Correction. United States District Court. District of New Jersey. Civil Action No. 19-13955 (FLW) (DEA) (CONSOLIDATED) *Vifor (International) AG and American Regent, Inc.*, Plaintiffs v. *MYLAN Laboratories Ltd. and Sandoz Inc.*, Defendants. Dated Nov. 13, 2020. 15 pages.

(Continued)

*Primary Examiner* — John Pak

(74) *Attorney, Agent, or Firm* — Sorell, Lenna & Schmidt, LLP

(57) ABSTRACT

A water soluble iron carbohydrate complex obtainable from an aqueous solution of iron(III) salt and an aqueous solution of the oxidation product of one or more maltrodextrins using an aqueous hypochlorite solution at a pH-value within the alkaline range, where, when one maltodextrin is applied, its dextrose equivalent lies between 5 and 20, and when a mixture of several maltodextrins is applied, the dextrose equivalent of the mixture lies between 5 and 20 and the dextrose equivalent of each individual maltodextrin contained in the mixture lies between 2 and 40, a process for its production and a medicament for the treatment and prophylaxis of iron deficiency conditions.

29 Claims, No Drawings

(56) References Cited

U.S. PATENT DOCUMENTS

| | | |
|---|---|---|
| 3,908,004 A | 9/1975 | Kitching |
| 3,928,581 A | 12/1975 | Dahlberg et al. |
| 3,965,133 A | 6/1976 | Dahlberg et al. |
| 3,969,395 A | 7/1976 | Dahlberg et al. |
| 4,056,672 A | 11/1977 | Dahlberg et al. |
| 4,180,567 A | 12/1979 | Herb |
| 4,189,474 A | 2/1980 | Kurosaki et al. |
| 4,335,116 A | 6/1982 | Howard |
| 4,370,476 A | 1/1983 | Usher et al. |
| 4,599,405 A | 7/1986 | Miller et al. |
| 4,640,837 A | 2/1987 | Coleman et al. |
| 4,788,281 A | 11/1988 | Tosoni et al. |
| 5,102,652 A | 4/1992 | Groman et al. |
| 5,160,726 A | 11/1992 | Josephson et al. |
| 5,541,158 A | 7/1996 | Vance et al. |
| 5,624,668 A | 4/1997 | Larence et al. |
| 5,635,611 A | 6/1997 | Ishiguro et al. |
| 5,746,999 A | 5/1998 | Gries et al. |
| 5,756,715 A | 5/1998 | Monte et al. |
| 5,831,043 A | 11/1998 | Fleche |
| 5,866,533 A | 2/1999 | Beck et al. |
| 6,495,177 B1 | 12/2002 | deVries et al. |
| 6,587,550 B2 | 7/2003 | Council et al. |
| 6,599,498 B1 | 7/2003 | Groman et al. |
| 6,690,571 B2 | 2/2004 | Shindo et al. |
| 6,773,924 B2 | 8/2004 | Beck et al. |
| 6,911,342 B2 | 6/2005 | Helenek et al. |
| 6,960,571 B2 | 11/2005 | Helenek et al. |
| 7,169,359 B2 | 1/2007 | Helenek et al. |
| 7,612,109 B2 | 11/2009 | Geisser et al. |
| 7,687,273 B2 | 3/2010 | Beck et al. |
| 7,754,702 B2 | 7/2010 | Helenek et al. |
| 7,871,597 B2 | 1/2011 | Groman et al. |
| 7,883,897 B2 | 2/2011 | Beck et al. |
| 7,964,568 B2 | 6/2011 | Beck et al. |
| 8,071,542 B2 | 12/2011 | Conner et al. |
| 8,263,577 B2 * | 9/2012 | Reim .................. A61P 7/06 514/54 |
| 8,431,549 B2 | 4/2013 | Helenek et al. |
| 8,722,101 B2 * | 5/2014 | Tanner-Baumgartner .................. A61K 47/61 424/647 |
| 8,772,101 B2 | 7/2014 | Xie et al. |
| 8,778,878 B2 | 7/2014 | Conner et al. |
| 8,895,612 B2 | 11/2014 | Helenek et al. |
| 9,120,838 B2 | 9/2015 | Demchenko et al. |
| 10,478,450 B2 | 11/2019 | Helenek et al. |
| 2003/0191090 A1 | 10/2003 | Andreasen et al. |
| 2003/0232084 A1 | 12/2003 | Groman et al. |
| 2004/0131703 A1 | 7/2004 | Bach et al. |
| 2004/0180849 A1 | 9/2004 | Helenek et al. |
| 2005/0163849 A1 | 7/2005 | Wong et al. |
| 2006/0116349 A1 | 6/2006 | Helenek et al. |
| 2006/0134227 A1 | 6/2006 | Bortz et al. |
| 2007/0161600 A1 | 7/2007 | Helenek et al. |
| 2008/0214496 A1 | 9/2008 | Tanner-Baumgartner et al. |
| 2008/0234226 A1 | 9/2008 | Erichsen et al. |
| 2008/0269167 A1 | 10/2008 | Ziegler et al. |
| 2009/0028962 A1 | 1/2009 | Bortz et al. |
| 2010/0099647 A1 | 4/2010 | Geisser et al. |
| 2011/0144054 A1 | 6/2011 | Groman et al. |
| 2011/0287033 A1 | 11/2011 | Conner et al. |
| 2012/0316133 A1 | 12/2012 | Geisser et al. |
| 2013/0230565 A1 | 9/2013 | Helenek et al. |
| 2014/0187514 A1 | 7/2014 | Tanner-Baumgartner et al. |
| 2019/0276563 A1 | 9/2019 | Geisser et al. |

FOREIGN PATENT DOCUMENTS

| | | |
|---|---|---|
| CA | 2493806 A | 5/2004 |
| CH | 423744 | 11/1966 |
| CN | 1353194 A | 6/2002 |
| CZ | 245379 | 12/1983 |
| DE | 461 370 C | 6/1928 |
| DE | 3 443 251 A1 | 5/1986 |
| DE | 3443251 A1 | 5/1986 |
| DE | 696 15 620 T2 | 4/2002 |
| DE | 102 49 552 A1 | 5/2004 |
| EP | 0051707 | 5/1982 |
| EP | 0150085 A2 | 7/1985 |
| EP | 0 427 349 A2 | 5/1991 |
| EP | 0543020 A1 | 6/1992 |
| EP | 0543020 B1 | 6/1992 |
| EP | 0543020 | 5/1993 |
| EP | 0634174 A1 | 1/1995 |
| EP | 0 755 944 A2 | 1/1997 |
| EP | 0 875 249 A1 | 11/1998 |
| EP | 1554315 | 10/2002 |
| EP | 1231903 B1 | 1/2006 |
| EP | 1 719 496 A2 | 11/2006 |
| EP | 3339329 A1 | 6/2018 |
| ES | 282099 | 11/1962 |
| FR | 1 451 203 | 1/1966 |
| FR | 1451203 | 1/1966 |
| GB | 289 280 A | 4/1928 |
| GB | 335965 | 10/1930 |
| GB | 748024 | 4/1956 |
| GB | 828404 A | 2/1960 |
| GB | 879441 | 10/1961 |
| GB | 879441 A | 10/1961 |
| GB | 928238 A | 6/1963 |
| GB | 978485 A | 12/1964 |
| GB | 985206 | 3/1965 |
| GB | 1 111 929 | 5/1968 |
| GB | 1111929 | 5/1968 |
| GB | 199951 | 7/1970 |
| GB | 1199951 A | 7/1970 |
| GB | 1258566 A | 12/1971 |
| GB | 1377006 A | 12/1974 |
| GB | 2 129 821 A | 5/1984 |
| WO | 199009182 | 8/1990 |
| WO | WO 95/07303 A1 | 3/1995 |
| WO | WO-95/32978 A1 | 12/1995 |
| WO | 97/11711 | 4/1997 |
| WO | WO-97/11711 A1 | 4/1997 |
| WO | WO-97/17377 A1 | 5/1997 |
| WO | 99/48533 | 9/1999 |
| WO | 00/30657 | 6/2000 |
| WO | WO-00/30657 A1 | 6/2000 |
| WO | 00/61191 | 10/2000 |
| WO | 200006634 | 11/2000 |
| WO | WO-00/66634 A1 | 11/2000 |
| WO | WO 01/12163 A1 | 2/2001 |
| WO | 02/07700 A2 | 7/2001 |
| WO | 02/46241 | 6/2002 |
| WO | 2002/046241 A2 | 6/2002 |
| WO | WO-02/46241 | 6/2002 |
| WO | WO-2004/019032 A1 | 3/2004 |
| WO | 2004/037865 A1 | 5/2004 |
| WO | 2004037865 | 5/2004 |
| WO | WO-2004/037865 A1 | 5/2004 |
| WO | WO-2004/082693 A1 | 9/2004 |
| WO | 2004108121 A1 | 12/2004 |
| WO | WO-2006/084782 A1 | 8/2006 |
| WO | WO-2007/023154 A2 | 3/2007 |
| WO | WO-2007/055804 A2 | 5/2007 |
| WO | WO-2007/060038 A2 | 5/2007 |
| WO | WO-2007/081744 A2 | 7/2007 |
| WO | 2011/055374 A2 | 5/2011 |
| WO | 2016/151367 A1 | 9/2016 |
| WO | 2016/181195 A1 | 11/2016 |

OTHER PUBLICATIONS

Reply Declaration of Geert-Jan Boons, Ph.D. in Support of Plaintiffs' Motion for Judicial Correction. United States District Court. District of New Jersey. Civil Action No. 19-13955 (FLW) (DEA) (CONSOLIDATED) *Vifor (International) AG and American Regent, Inc.*, Plaintiffs v. *MYLAN Laboratories Ltd. and Sandoz Inc.*, Defendants. Dated Nov. 13, 2020. 80 pages.

Defendants' Brief in Opposition to Plaintiffs' Motion for Judicial Correction. United States District Court. District of New Jersey.

(56) References Cited

OTHER PUBLICATIONS

Civil Action No. 19-13955 (FLW) (DEA) (CONSOLIDATED) *Vifor (International) AG and American Regent, Inc.*, Plaintiffs v. *MYLAN Laboratories Ltd. and Sandoz Inc.*, Defendants. Dated Nov. 2, 2020. 22 pages.
Declaration of Alexei Demchenko, PhD., In Opposition to Plaintiffs' Motion for Judicial Correction of Claim 1 of U.S. Pat. No. 10,519,252. United States District Court. District of New Jersey. Civil Action No. 19-13955 (FLW) (DEA) (CONSOLIDATED) *Vifor (International) AG and American Regent, Inc.*, Plaintiffs v. *MYLAN Laboratories Ltd. and Sandoz Inc.*, Defendants. Dated Nov. 2, 2020. 110 pages.
Declaration of Adam D. Sussman in Support of Defendants' Brief in Opposition to Plaintiffs' Motion for Judicial Correction. United States District Court. District of New Jersey. Civil Action No. 19-13955 (FLW) (DEA) (CONSOLIDATED) *Vifor (International) AG and American Regent, Inc.*, Plaintiffs v. *MYLAN Laboratories Ltd. and Sandoz Inc.*, Defendants. Dated Nov. 2, 2020. 3 pages.
Exhibit 1. Declaration Under 37 CFR Section 1.132 of Dr. Erik Phillipp. In re Patent Application of Peter Geisser et al. U.S. Appl. No. 13/835,400, filed Mar. 15, 2013. Dated Feb. 15, 2016. 45 pages.
Exhibit 2. Defendants' Invalidity Contentions Regarding U.S. Pat. No. 7,612,109, 7,754,702, 8,895,612, 9,376,505 and 10,519,252 Made Under Local Patent Rules 3.3 and 3.6. United States District Court. District of New Jersey. Civil Action No. 19-13955 (FLW) (DEA) (CONSOLIDATED) *Vifor (International) AG and American Regent, Inc.*, Plaintiffs v. *MYLAN Laboratories Ltd. and Sandoz Inc.*, Defendants. Dated Mar. 17, 2020. 15 pages.
Exhibit 3. Excerpt from Plaintiffs' Response to Defendants' Invalidity Contentions Regarding U.S. Pat. No. 7,612,109, 9,376,505, 10,519,252, 7,754,702 and 8,895,612. United States District Court. District of New Jersey. Civil Action No. 19-13955 (FLW) (DEA) (CONSOLIDATED) *Vifor (International) AG and American Regent, Inc.*, Plaintiffs v. *MYLAN Laboratories Ltd. and Sandoz Inc.*, Defendants. Dated Jun. 15, 2020. 22 pages.
Exhibit 4. Certified Copy dated Jun. 13, 2019 of original filed Claims of U.S. Appl. No. 11/620,986, filed Jan. 8, 2007, now U.S. Pat. No. 7,754,702. 12 pages.
Exhibit 5. Excerpt from Certified Copy dated Jan. 16, 2020 of U.S. Appl. No. 13/835,400, filed Mar. 15, 2013, now US Patent 10,519,252. 39 pages.
Exhibit 5-A. Excerpt from U.S. Appl. No. 13/835,400, filed Mar. 15, 2013, now U.S. Pat. No. 10,519,252.
Exhibit 5-B. Excerpt from U.S. Appl. No. 13/835,400, filed Mar. 15, 2013, now U.S. Pat. No. 10,519,252.
Exhibit 5-C. Excerpt from U.S. Appl. No. 13/835,400, filed Mar. 15, 2013, now U.S. Pat. No. 10,519,252.
Exhibit 6. Prosecution History of the '252 Patent, Recitations of "3(S)" Chemical Name. 26 pages.
Exhibit 7. U.S. Pat. No. 6,587,550 B2 issued Jul. 1, 2003 from U.S. Appl. No. 09/783,340, filed Feb. 14, 2001. 9 pages.
Exhibit 8. U.S. Pat. No. 9,120,838 B2 issued Sep. 1, 2015 from U.S. Appl. No. 14/112,830, filed Apr. 18, 2012. 26 pages.
Exhibit 9. Thaburet, Jean-Francois, et al. TEMPO-mediated oxidation of maltodextrins and D-glucose: effect of pH on the selectivity and sequestering ability of the resulting polycarboxylates. Carbohydrate Research 330 (2001) pp. 21-29. 10 pages.
Exhibit 10. Suzukamo, G., et al. C3 Epimerization and Selective C2-C3 Bond Fission of Alkyl Chrysanthemate. Tetrahedron Letters, vol. 25, No. 15, pp. 1595-1598, 1984 Pergamon Press Ltd. Great Britain.
Exhibit 11. Guerinot, Amandine, et al. FeCl3—6H20-catalyzed synthesis of substituted cis-2,6-tetrahydropyrans from—hydroxy allylic derivatives. Tetrahedron. vol. 67 (2011) pp. 5024-5033. 11 pages.
Fong, Singh K. A comparison between intravenous iron polymaltose complex (Ferrum Hausmann) and oral ferrous fumarate in the treatment of iron deficiency anaemia in pregnancy. Eur J Haematol 1998: 60; 119-124, 6 pages.

Fielding, J. Intravenous Iron-Dextrin in Iron-Deficiency Anaemia. British Medical Journal. Jul. 29, 1961, pp. 279-283.
Besemer, Arie C., et al. The Catalytic Effect of Bromide in the Hypochlorite Oxidation of Linear Dextrins and Inulin. starch/stiirke 46 (1994) Nr. 3, S. 101-106.
Collins, Peter M. (Ed.), et al. Excerpt from Dictionary of Carbohydrates. First Edition. 1998 Springer Science + Business Media Dordrecht. 5 pages.
Kearsley, M. W. and Dziedzic, S. Z., Editors. Excerpt from Handbook of Starch Hydrolysis Products and their Derivatives. First Edition. 1995 Springer Science + Business Media Dordrecht. 10 pages.
Dextrine. Wikipedia. 2 pages.
United States District Court, District of New Jersey. Plaintiffs' Preliminary Proposed Claim Construction and Identification of Evidence; *Vifor (International) AG and American Regent, Inc.*, Plaintiffs, v. *MYLAN Laboratories Ltd. and Sandoz Inc.*, Defendants. Civil Action No. 19-13955 (FLW) (DEA). Dated Jul. 6, 2020.
United States District Court, District of New Jersey. Defendants Mylan Laboratories Ltd.'s and Sandoz Inc.'s Preliminary Claim Constructions; *Vifor (International) AG and American Regent, Inc.*, Plaintiffs, v. *MYLAN Laboratories Ltd. and Sandoz Inc.*, Defendants. Civil Action No. 19-13955 (FLW) (DEA). Dated Jul. 6, 2020.
Reply to the Patentee's Appeal. Appeal No. T1139/19-3.3.01; Opposition in European Patent No. 1973549 (Vifor (International) AG); Opponent:Generics [UK] Limited (07). Filed in the European Patent Office Oct. 2, 2020, 16 pages.
Response to the communication dated May 19, 2020, forwarding the statements setting out the grounds of appeal of the opponents 03, 06, and 07. Appeal No. T1139/19-3.3.01 to Opposition in European Patent No. 1973549; Appellant: Vifor (International) AG; Respondents: Hoffmann Eitle Patent- und Rechtsanwalte, Partnerschaftsgesellschaft mbB, Pharmacosmos Holding A/S,Teva Pharmaceutical Industries Ltd., HGF Limited, STADA Arzneimittel AG, Taylor Wessing LLP, Generics Limited. Filed in the European Patent Office Oct. 2, 2020.
Reply to the Patentee's Appeal. Appeal No. T1139/19-3.3.01; Opposition in European Patent No. 1973549 (Vifor (International) AG); Opponent:Generics [UK] Limited (07). Filed in the European Patent Office Oct. 2, 2020, 330 pages.
Auxiliary requests during appeals procedure. Appeal No. T1139/19-3.3.01. Amended claims with annotations, filed Sep. 29, 2020 in European Appl. No. 07716309.5 / European Patent No. EP 1973549 (Vifor (International) AG), 145 pages.
Auxiliary requests during appeals procedure. Appeal No. T1139/19-3.3.01. Claims in European Appl. No. 07716309.5 / European Patent No. EP 1973549 (Vifor (International) AG), submitted to European Patent Office Sep. 29, 2020, 67 pages.
Responsive Expert Declaration of Daniel Coyne, MD (Redacted). In the United States District Court, District of New Jersey. Civil Action No. 19-13955. *Vifor (International) AG and American Regent, Inc.*, Plaintiffs v. *Mylan Laboratories Ltd. and Sandoz, Inc.*, Defendants. Dated Sep. 28, 2020. 22 pages.
Fishbane M.D., Steven. Safety in Iron Management. Amer. Jour. Kidney Dis. vol. 41, No. 6, Supp. 5, Jun. 2003, pp. S16-S26.
Aronoff, George, et al. Iron sucrose in hemodialysis patients: Safety of replacement and maintenance regimens. Kidney International, vol. 66 (2004), pp. 1193-1198.
Bailie, George R., et al. Hypersensitivity reactions and deaths associated with intravenous iron preparations. Nephrol Dial Transplant (2005) 20: 1443-1449 Advance Access publication Apr. 26, 2005.
Funk, Felix, et al. The new generation of intravenous iron: chemistry, pharmacology, and toxicology of ferric carboxymaltose. Arzneimittelforschung 2010: 60 (6a), pp. 345-353.
Declaration of Jieun Lee in Support of Defendants' Responsive Claim Construction Brief. In the United States District Court for the District of New Jersey. Civil Action No. 19-13955. *Vifor (International) AG and American Regent, Inc.*, Plaintiffs v. *Mylan Laboratories Ltd. and Sandoz, Inc.*, Defendants. Dated Sep. 28, 2020.
Markman Response Exhibit 40. Excerpt from the United States Pharmacopeia (USP 24) The National Formulary (NF 19) Jan. 1, 2000, 28 pages.

(56) References Cited

OTHER PUBLICATIONS

Markman Response Exhibit 41. Published International Application No. WO 02/46241 A2 published Jun. 13, 2002 in International Application No. PCT/YUOI/00031 filed Dec. 7, 2001, 34 pages.
Markman Response Exhibit 42. Excerpt from Dorland's Illustrated Medical Dictionary, vol. 27th Edition.
Markman Response Exhibit 43. Excerpt from Stedman's Medical Dictionary, Illustrated in Color, vol. 27th Edition.
Markman Response Exhibit 44. Transcript of Videotaped Deposition of Geert-Jan Boons, Ph.D. In the United States District Court for the District of New Jersey. Civil Action No. 19-13955. *Vifor (International) AG and American Regent, Inc.*, Plaintiffs v. *Mylan Laboratories Ltd. and Sandoz, Inc.*, Defendants. Deposition date Sep. 9, 2020. 217 pages.
Markman Response Exhibit 45. Transcript of Videotaped Deposition of Daniel Coyne, M.D. In the United States District Court for the District of New Jersey. Civil Action No. 19-13955. *Vifor (International) AG and American Regent, Inc.*, Plaintiffs v. *Mylan Laboratories Ltd. and Sandoz, Inc.*, Defendants. Deposition date Sep. 11, 2020. 161 pages.
Markman Response Exhibit 46. Chemical structure.
Declaration of M. David Weingarten in Support of Plaintiffs' Responsive Markman Brief. (Redacted) in the United States District Court for the District of New Jersey. Civil Action No. 19-13955. *Vifor (International) AG and American Regent, Inc.*, Plaintiffs v. *Mylan Laboratories Ltd. and Sandoz, Inc.*, Defendants. Dated Sep. 28, 2020.
Plaintiffs Exhibit A. Transcript of Videotaped Deposition of Daniel Coyne, M.D. (Redacted) In the United States District Court for the District of New Jersey. Civil Action No. 19-13955. *Vifor (International) AG and American Regent, Inc.*, Plaintiffs v. *Mylan Laboratories Ltd. and Sandoz, Inc.*, Defendants. Deposition date Sep. 11, 2020.
Plaintiffs Exhibit B. Transcript of Virtual Videotaped Deposition of Anthony L. DeFranco Ph.D. (Redacted) In the United States District Court for the District of New Jersey. Civil Action No. 19-13955. *Vifor (International) AG and American Regent, Inc.*, Plaintiffs v. *Mylan Laboratories Ltd. and Sandoz, Inc.*, Defendants. Deposition date Sep. 14, 2020. 74 pages.
Plaintiffs Exhibit D. van Zyl-Smit, R., et al. Experience with the Use of an Iron Polymaltose (Dextrin) Complex Given by Single Total Dose Infusion to Stable Chronic Haemodialysis Patients. Nephron 2002;92:316-323 Accepted: Dec. 12, 2007. 9 pages.
Plaintiffs Exhibit E. Kennedy, J.F. et al. Maltodextrins. Excerpt from Handbook of Starch Hydrolysis Products and their Derivatives. First Edition. 1995. 7 pages.
Plaintiffs Exhibit F. New Search [Code of Federal Regulations][Title 2i;vol. 3][-Revised as of Apr. 1, 2015] [Cite: 21CFR184.1444] Title 21—Food and Drugs Chapter 1 Food and Drug Administration Department of Health and Human Services Subchapter B—Food for Human Consumption (Continued) Part 184—Direct Food Substances Affirmed as Generally-Recognized as Safe Subpart B—Listing of Specific Substances Affirmed as GRAS Sec.184.1444. Maltodextrin. 3 pages.
Plaintiffs Exhibit G. Dokic, P., et al. Molecular characteristics of maltodextrins and rheological behaviour of diluted and concentrated solutions. Colloids and Surfaces A: Physicochemical and Engineering Aspects 141 ( 1998) 435-440.
Plaintiffs Exhibit M. Published European Patent Application No. EP 3339329 A1 published Jun. 27, 2018 from European Patent Application No. 16206398.6 filed on Dec. 22, 2016.
Plaintiffs Exhibit N. Transcript of Videotaped Deposition of Geert-Jan Boons, Ph.D. In the United States District Court for the District of New Jersey. Civil Action No. 19-13955. *Vifor (International) AG and American Regent, Inc.*, Plaintiffs v. *Mylan Laboratories Ltd. and Sandoz, Inc.*, Defendants. Deposition date Sep. 9, 2020. 100 pages.
Plaintiffs Exhibit O. European Patent No. EP 1231903 B1 issued on Jan. 11, 2006 from European Patent Application No. 00987277.1 filed Nov. 21, 2000. Proprietor: Sandoz AG. 11 pages.
Plaintiffs Exhibit Q. International Patent Publication No. WO 2016/151367 A1 published Sep. 29, 2016 from International Patent Application No. PCT/IB15/53305 filed on May 6, 2015. Assignee: Suven Life Sciences Limited (IN). 24 pages.
Plaintiffs Exhibit R. International Patent Publication No. WO 2016/181195 A1 published Nov. 17, 2016 from International Patent Application No. PCT/IB15/54655 filed on May 8, 2015. Assignee: Suven Life Sciences Limited (IN). 22 pages.
Plaintiffs Exhibit S. International Patent Publication No. WO 2011/055374 A2 published May 12, 2011 from International Patent Application No. PCT/IN09/00624 filed on Nov. 4, 2009. Assignee: Symed Labs Limited (IN). 22 pages.
Letter from Plaintiffs Counsel to the Honorable Freda L. Wilson, United States District Court, District of New Jersey. Re: *Vifor (International) AG, et al.v. Mylan Laboratories Ltd., et al.* Civil Action No. 19-13955 (FLW) (DEA) (CONSOLIDATED). Dated Oct. 5, 2020. 1 page.
Letter from Defendants Counsel to the Honorable Freda L. Wilson, United States District Court, District of New Jersey. RE: *Vifor (International) AG, et al. v. Mylan Laboratories Ltd., et al.* Civil Action No. 19-13955 (FLW) (DEA) (CONSOLIDATED). Dated Oct. 9, 2020. 3 pages.
Plaintiffs Notice of Motion for Judicial Correction. In the United States District Court for the District of New Jersey. Civil Action No. 19-13955. *Vifor (International) AG and American Regent, Inc.*, Plaintiffs v. *Mylan Laboratories Ltd. and Sandoz, Inc.*, Defendants. Dated Oct. 9, 2020. 2 pages.
Plaintiffs Briefs in Support of Motion for Judicial Correction. In the United States District Court for the District of New Jersey. Civil Action No. 19-13955. *Vifor (International) AG and American Regent, Inc.*, Plaintiffs v. *Mylan Laboratories Ltd. and Sandoz, Inc.*, Defendants. Dated Oct. 9, 2020. 13 pages.
Declaration of Brian Stoltz, Ph.D. In Support of Plaintiffs' Motion for Judicial Correction of Claim 1 of U.S. Pat. No. 10,519,252. In the United States District Court for the District of New Jersey. Civil Action No. 19-13955. *Vifor (International) AG and American Regent, Inc.*, Plaintiffs v. *Mylan Laboratories Ltd. and Sandoz, Inc.*, Defendants. Dated Oct. 9, 2020. 66 pages.
Declaration of Erik Philipp, Ph.D. In Support of Plaintiffs' Motion for Judicial Correction of Claim 1 of U.S. Pat. No. 10,519,252. In the United States District Court for the District of New Jersey. Civil Action No. 19-13955. *Vifor (International) AG and American Regent, Inc.*, Plaintiffs v. *Mylan Laboratories Ltd. and Sandoz, Inc.*, Defendants. Dated Oct. 9, 2020. 5 pages.
Declaration of William P. Deni, Jr. In Support of Plaintiffs' Motion for Judicial Correction. In the United States District Court for the District of New Jersey. Civil Action No. 19-13955. *Vifor (International) AG and American Regent, Inc.*, Plaintiffs v. *Mylan Laboratories Ltd. and Sandoz, Inc.*, Defendants. Dated Oct. 9, 2020. 2 pages.
Danielson, Bo G., et al. Iron Therapy. Excerpt from Iron Therapy with Special Emphasis on Intravenous Administration. First Edition. Vifor International. 1996. 18 pages.
Opposition Decision. IP Australia—Australian Patent Office Pharmacosmos Holding A/S v American Regent, Inc. [2020] APO 36; RE: AU Patent Application: 2016205002 for Methods and compositions for administration of iron. Patent Applicant: American Regent, Inc. Opponent: Pharmacosmos Holding A/S; Decision dated Jul. 29, 2020.
United States District Court, District of New Jersey. Joint Claim Construction and Prehearing Statement. *Vifor (International) AG and American Regent, Inc.*, Plaintiffs v. *Mylan Laboratories Ltd. and Sandoz, Inc.*, Defendants. Civil Action No. 19-13955 (FLW) (DEA). Filed in the Court on Jul. 24, 2020.
KDOQI Clinical Practice Guidelines and Clinical Practice Recommendations for Anemia in Chronic Kidney Disease. Amer J Kidney Diseases vol. 47, No. 5, Suppl 3, May 2006.
NDA 17-441/S-171—INFeD® (Iron Dextran Injection USP) Watson Pharmaceuticals, Inc. Revised: Jul. 2009.
NDA 20-955/S-003—Ferrlecit® Description. Watson Pharmaceuticals, Inc and R & D Laboratories, Inc. 2001.

(56) References Cited

OTHER PUBLICATIONS

NDA 21-135—Labeling—Venofer® (iron sucrose injection)—Description NKF-DOQI Clinical Practice Guidelines for the Treatment of Anemia of Chronic Renal Failure, New York Kidney Foundation, 1997.
NDA 40-024/S-022—Dexferrum®—(Iron Dextran Injection, USP) American Regent, Inc. Rev. Aug. 2008.
Neiser, S., et al. Assessment of dextran antigenicity of intravenous iron products by an immunodiffusion assay. Port J Nephrol Hypert 2011; 25(3): 219-224 Advance Access publication Sep. 13, 2011.
Ring, J., et al. Letter and Reply. Port J Nephrol Hypert 2012; 26(4): 000-000 Advance Access publication Sep. 27, 2012.
Neiser, S., et al. Reply to the letter to the editor by Johannes Ring and Rudi Valenta on the article "Assessment of dextran antigenicity of intravenous iron products by an immunodiffusion assay." Port J Nephrol Hyper! 2012; 26(4): 308-312.
Neisser, S., et al. Physico-chemical properties of the new generation IV iron preparations ferumoxytol, iron isomaltoside 1000 and ferric carboxymaltose. Biometals. Mar. 11, 2015.
New Drug Application (NDA) 22-054 for Injectafer (Ferric Carboxymaltose) for the treatment of iron deficiency anemia in patients with heavy uterine bleeding or postpartum patients. FDA Advisory Committee Briefing Document. Drug Safety and Risk Management Committee Feb. 1, 2008.
Fielding, J. Intravenous Iron Dextrin in Iron Deficiency Anaemia. New Intramuscular Haematinic. British Medical Journal. Jul. 29, 1961, pp. 279-283.
New Zealand Data Sheet. Ferrum H solution for injection 100 mg/2mL ampoule. Rev. Apr. 18, 2019.
Newnham, E. Safety of iron polymaltose given as a total dose iron infusion. Internal Medicine Journal. vol. 36 (2006) pp. 672-674.
American Regent Press Release. Venofer (iron sucrose injection USP) receives FDA approval for th treatment of iron deficiency anemia in pre-dialysis patients. Jun. 17, 2005.
Nissenson, A., et al. Controversies in iron management. Kidney International. vol. 64, Suppl. 87 (2003) pp. S64-S71.
National Kidney Foundation. K/DOQI Clinical Practice Guidelines for Hemodialysis Adequacy, 2000. Am J Kidney Dis 37:S7-S64, 2001 (suppl 1).
De Nooy, A., et al. On the use of stable organic nitroxyl radicals for the oxidation of primary and secondary alcohols. Synthesis. Oct. 1996.
Nordmeier, E. Static and dynamic light scattering solution behavior of pullulan and dextran in comparison. Journal of Physical Chemistry, vol. 97, 1997, pp. 5770-5785.
In the United States Patent and Trademark Office. Notice of Correction of Certificate of Service for Petition for Inter Partes Review of U.S. Pat. No. 7,754,702. Dated Jun. 24, 2015.
In the United States Patent and Trademark Office. Notice of Correction of Certificate of Service for Petition for Inter Partes Review of U.S. Pat. No. 8,431,549. Dated Jun. 24, 2015.
In the United States Patent and Trademark Office. Notice of Correction of Certificate of Service for Petition for Inter Partes Review of U.S. Pat. No. 8,895,612. Dated Jun. 24, 2015.
U.S. Appl. No. 14/683,415 (Helenek) for Methods and Compositions for Administration of Iron. 192 pages.
Notice of Response in lieu of Motion (to Board Order, Paper 8) Before the PA Tent Trial and Appeal Board Pharmacosmos A/S Petitioner V. Luitpold Pharmaceuticals, Inc. Patent Owner Cases 1 IPR2015-01490; U.S. Pat. No. 7,754,702 B2; IPR2015-01493; U.S. Pat. No. 8,431,549 B2 IPR2015-01495; U.S. Pat. No. 8,895,612 B2. Served Oct. 20, 2015.
Notice (Regarding the Filing of Corrected Exhibits and Papers) United States Patent and Trademark Office Before the Patent Trial and Appeal Board. Pharmacosmos A/S, Petitioner, V. Luitpold Pharmaceuticals, Inc., Patent Owner. Cases1 IPR2015-01490; U.S. Pat. No. 7,754,702 B2 and IPR2015-01493; U.S. Pat. No. 8,431,549 B2. Apr. 25, 2016.
Notice (Regarding the Filing of Corrected Exhibit) United States Patent and Trademark Office Before the Patent Trial and Appeal Board. Pharmacosmos A/S, Petitioner, V. Luitpold Pharmaceuticals, Inc., Patent Owner. Cases IPR2015-01490; U.S. Pat. No. 7,754,702 B2 and IPR2015-01493; U.S. Pat. No. 8,431,549 B2. May 31, 2016.
Objections to Petitioner's Reply and Opposition Evidence. United States Patent and Trademark Office Before the Patent Trial and Appeal Board. Pharmacosmos A/S, Petitioner, V. Luitpold Pharmaceuticals, Inc., Patent Owner. IPR2015-01493; U.S. Pat. No. 8,431,549 B2. Jun. 27, 2016.
Objections to Petitioner's Reply and Opposition Evidence. United States Patent and Trademark Office Before the Patent Trial and Appeal Board. Pharmacosmos A/S, Petitioner, V. Luitpold Pharmaceuticals, Inc., Patent Owner. IPR2015-01490; U.S. Pat. No. 7,754,702 B2. Jun. 27, 2016.
U.S. Appl. No. 11/620,986, filed Jan. 8, 2007 (Helenek), 99 pgs.
U.S. Appl. No. 12/787,283, filed May 25, 2010 (Helenek), 75 pgs.
U.S. Appl. No. 12/787,283, filed Dec. 9, 2013 (Helenek), 48 pgs.
Dextran. Excerpt from the Merck Index, 14th Edition, 2006, 4 pages.
Online query of Orange Book: Approved Drug Products with Therapeutic Equivalence Evaluations. Query on "022180" dated Mar. 9, 2015, 4 pgs.
Online query of Orange Book: Approved Drug Products with Therapeutic Equivalence Evaluations. Query on "203565" dated Mar. 9, 2015, 4 pgs.
Erni, et al. Chemical Characterization of Iron (III)-Hydroxide-Dextrin Complexes. Arzneimittel Forschung—Drug Research. vol. 34 No. 2 (1984) pp. 1555-1559.
Owens III, Donald E., et al. Opsonization, biodistribution, and pharmacokinetics of polymeric nanoparticles. International Journal of Pharmaceutics. vol. 307 (2006) 93-102.
Mulder, Midas Berend. Comparison of hypersensitivity reactions of intravenous iron: iron isomaltoside-1000 (Monofer) versus ferric carboxy-maltose (Ferinject) A single center, cohort study, British Journal of Clinical Pharmacology, 2019, vol. 85, pp. 385-392.
United States District Court, District of New Jersey. Defendants' Invalidity Contentions Regarding U.S. Pat. Nos. 7,612,109, 7,754,702, 8,895,612, 9,376,505, and 10,519,252 Made Under Local Patent Rules 3.3 and 3.6 [Redacted]; *Vifor (International) AG and American Regent, Inc.*, Plaintiffs, v. *Mylan Laboratories Ltd. and Sandoz Inc.*, Defendants. Civil Action No. 19-13955 (FLW) (DEA).
United States District Court, District of New Jersey. Plaintiff' Preliminary List of Proposed Claim Terms for Construction; *Vifor (International) AG and American Regent, Inc.*, Plaintiffs, v. *Mylan Laboratories Ltd. and Sandoz Inc.*, Defendants. Civil Action No. 19-13955 (FLW) (DEA).
United States District Court, District of New Jersey. Defendants Mylan Laboratories Ltd.'s and Sandoz Inc.'s Identification Ofprosed Claim Terms for Construction; *Vifor (International) AG and American Regent, Inc.*, Plaintiffs, v. *Mylan Laboratories Ltd. and Sandoz Inc.*, Defendants. Civil Action No. 19-13955 (FLW) (DEA).
Auerbach, Michael, et al. "Intravenous Iron Optimizes the Response to Recombinant Human Erythropoietin in Cancer Patients With Chemotherapy-Related Anemia: A Multicenter, Open-Label, Randomized Trial" Journal of Cinical Oncology, vol. 22, No. 7 (Apr. 1, 2004).
Auerbach, Michael, et al. "Clinical use of the total dose intravenous infusion of iron dextran" J Lab Clin Med 1988; 111:566-70 (vol. 111 No. 5, May 1988).
Fox, Sir Theodore, et al. (Ed.) "Rapid Administration of Iron Dextran in Late Pregnancy," The Lancet, vol. 1, Jan.-Jun. 1963. The Lancet Limited, London ("Basu").
Beshara, Soheir et al."Pharmacokinetics and red cell utilization of 52Fe/59Fe-labelled iron polymaltose in anaemic patients using positron emission tomography", British Journal of Haematology, 2003, 120, 853-859 in 2003.
Coe, Emma M., et al. "An Investigation into the Size of an Iron DextranComplex," Journal of Inorganic Chemistry, vol. 60,No. 2, 1995, pp. 149-153.
Danielson, Bo G. "Structure, Chemistry, and Pharmacokinetics of Intravenous Iron Agents" J Am Soc Nephrol, vol. 15; S93-S98, 2004.

(56) References Cited

OTHER PUBLICATIONS

Esposito, B.P. et al. Labile iron in parenteral formulations and its potential for generating plasma nontransferrin-bound iron in dialysis patients European Journal of Clinical Investigation (2002) 32 (Suppl. I), 42-49.
Ferrosig® Label. "The Ferrosig® Label for iron polymaltose 50 mg/mL" date of preparation Jul. 10, 2003.
Fessenden et al. "Organic Chemistry, 6th Edition", Chapter 23 Carbohydrates pp. 923-960. (1998).
Floor et al. "Preparation and Calcium Complexation of Oxidized Polysaccharides" starch 41 (1989) Nr. 9, S. 348-354.
Geisser, P., et al. "Investigation on the Dosage/Efficacy Relationship of Iron Dextran in Veal Calves," Therapeutics for States of Deficiency. Arzneim-Forsch/Drug Res. 41 (I), No. 1 (1991).
Geisser, P., et al. "Structure/Histotoxicity Relationship of Parenteral Iron Preparations" Therapeutics for States of Deficiency. Arzneim-Forsch/Drug Res. 42 (II), No. 12 (1992).
Crichton, R. R. et al. "Iron Therapy With Special Emphasis on Intravenous Administration," 1st Edition, 1996, pp. 57-72; 81-96.
Jahn, M. R., et al. "A Comparative Study of the Physicochemical Properties of Iron Isomaltoside 1000 (Monofer®), a New Intravenous Iron Preparation and Its Clinical Implications" European Journal of Pharmaceutics and Biopharmaceutics 78 (2011) 480-491.
Jankiewicz, B. et al. "Complexing of Iron (III) Hydroxide With Oligomaltose and Products of its Electrochemical Oxidation" Acta Polon. Pharm. XLV, NB 6, 1988.
Macdougall et al. "Administration of Intravenous Iron Sucrose as a 2-Minute Push to CKD Patients: A Prospective Evaluation of 2,297 Injections" Am J Kidney Dis Vo. 46, No. 2 Aug. 2005:283-289.
Marchasin "The Treatment of Iron-Deficiency Anemia with Intravenous Iron Dextran," Blood vol. 23, No. 3 Mar. 1964, pp. 354-358.
Mollan et al. "Maltodextrin" Analytical Profiles of Drug Substances and Excipients, Vo. 24, 1996, pp. 309-349.
Nadarajan et al. "Anaemia and Iron Status Among Blood Donors in a Blood Transfusion Unit in Malaysia" Malaysian J. Pathol. 2002; 24(2): 99-102.
Neiser, Susann, et al. "Physico-chemical properties of the new generation IV iron preparations ferumoxytol, iron isomaltoside 1000 and ferric carbxoymaltose," Biometals (2015) 28:615-635.
Physcians Desk Reference 55th Edition, 2001, INFeD® Uron Dextran Injection, USP) 2878-2881.
Physcians Desk Reference 56th Edition, 2002, pp. 580-581; 3386-3387.
Pond et al. Cadmium-Induced Anemia in Growing Pigs: Protective Effect of Oral or Parenteral Iron., Journal of Animal Science, vol. 36, No. 6, 1973, pp. 1122-1124 (1973).
Perkins, John J. Principles and Methods of Sterilization in Health Sciences. Charles C Thomas Pub Limited, 1983.
Singh, K., et al. "A comparison between intravenous iron polymaltose complex (Ferrum Hausmann®) and oral ferrous fumarate in the treatment of iron deficiency anaemeia in pregnancy" Eur J Haematol. Feb. 1998;60(2):119-24.
Spinowitz, B.S., et al. "The Safety and Efficacy of Ferumoxytol Therapy in Anemic Chronic Kidney Disease Patients," Kidney International, 2005, vol. 68, pp. 1801-1807.
Stranz et al. "A Review of pH and Osmolarity" International Journal of Pharmaceutical Compounding, vol. 6, No. 3, May/Jun. 2002.
Thaburet et al. "TEMPO-mediated Oxidation of Maltodextrins and D-Glucose: Effect of pH on the Selectivity and Sequestering Ability of the Resulting Polycarboxylates" Carbohydrate Research 330 (2001) 21-29.
USPNF, Maltodextrin Official Monographs, 2577-2578 (2002).
Van Zyl-Smit et al. "Experience with the Use of an Iron Polymaltose (Dextrin) Complex Given by Single Total Dose Infusion to Stable Chronic Haemodialysis Patients," Nephron (Oct. 2002, 92, pp. 316-323).
Weiss et al. "Anemia of Chronic Disease" N. Engl. J. Med. 2005;352:1011-23.

Zou et al. "Physicochemical Characterization of Iron Carbohydrate Colloid Drug Products" The AAPS Journal, vol. 19, No. 5, Sep. 2017. DOI: 10.1208/sl2248-01 7-0126-0.
Technical Quality Dextran, Pamphlet by Pharmacosmos, Apr. 2014, 6 pages.
Teuten, A., Letter from SagittariusIP European Law Firm to European Patent Office regarding European Patent Application No. 07716309.5, dated Jan. 15, 2014, 7 pages.
Teuten, A., Letter from SagittariusIP European Law Firm to European Patent Office regarding European Patent Application No. 07716309.5, dated Dec. 14, 2012, 4 pages.
Thaburet, JF et al., "TEMPO-mediated oxidation of maltodextrins and D-glucose: effect of pH on the selectivity and sequestering ability of the resulting polycarboxylates," Carbohydrate Research, 330 (2001) pp. 21-29.
The Merck Index, Dextranase, 15th Edition, 2006, pp. 2959-2950.
The Official Compendia of Standards, Combined Index to USP 25 and NF 20, 2002, 30 pages.
The Official Compedia of Standards, Combined Index to USP 26 and NF 21, 2003, 35 pages.
Pink Sheet, "Fisons' Opticrom, Imferon May be off U.S. Market Until Late 1992 as the Company Upgrades U.K. Manufacturing Plant to Meet FDA Quality Control Concerns", Pharma intelligence, Word Count: 850 | Article# 00530510003 / Posted: Dec. 23, 1991 5:00 AM.
Thorek, D.L.J., et al., "Superparamagnetic Iron Oxide Nanoparticle Probes for Molecular Imaging," Annals of Biomedical Engineering, vol. 34, No. 1, Jan. 2006, pp. 23-38.
Till, M.C. letter to Office of Regulatory Policy , Food and Drug Administration for application for patent term extension of U.S. Pat. No. 7,612,109, received Oct. 22, 2014, 75 pages.
Till, M.C., letter regarding Patent Term Extension—Application for U.S. Pat. No. 6,599,498, received Mar. 26, 2014, 144 pages.
Tuomainen, T. P., et al., "Oral Supplementation with Ferrous Sulfate but not with Nonionic Iron Polymaltose Complex Increases the Susceptibility of Plasma Lipoproteins to Oxidation," Nutrition Research, vol. 19, No. 8, 1999, pp. 1121-1132.
Hartsfield, J, Iron Status in the Female Blood Donor, Nutrition Bytes, 4(1), 1998, pp. 1-6.
Umeki, K et al Structures of Multi-Branched Dextrins Produced by Saccharifying alpha-Amylase from Starch J. Biochem., 78, 897-903 (1975).
U.S. Court of Appeals Federal Circuit Judgement Affirmed in *Luitpold Pharmaceuticals, Inc.*, Appellant v. *Pharmacosmos A/S*, Cross-Appellant 2017-1715, 2017-1725 IPR2015-01490, IPR2015-01493 (Apr. 12, 2018) 2 pages.
U.S. Court of Appeals Federal Circuit Mandate Issued in *Luitpold Pharmaceuticals, Inc.*, Appellant v. *Pharmacosmos A/S*, Cross-Appellant 17/1715, 17/1725, 17/1786 IPR2015-01490, IPR2015-01493 (May 21, 2018) 1 page.
U.S. Court of Appeals Federal Circuit Notice of Entry of Judgment Without Opinion Issued in *Luitpold Pharmaceuticals, Inc.*, Appellant v. *Pharmacosmos A/S*, Cross-Appellant 17/1715, 17/1725, 17/1786 IPR2015-01490, IPR2015-01493 (Apr. 12, 2018) 1 page.
USPNF, Dextran Official Monographs, 601-606 (2005).
Declaration of Linhardt, Robert Filed on behalf of Pharmacosmos A/S, IPR2019-01142, Jun. 22, 2015, pp. 1-29 for U.S. Pat. No. 8,895,612.
USPNF, Maltodextrin Official Monographs, 2789-2791 (2003).
USP Pharmacists' Pharmacopoeia, 3 Supplement Pharmacists' Pharmacopoeia, second edition, official May 1, 2009-Aug. 1, 2009.
USP 28-NF 23, Official Monograph/Dextran, pp. 601-602, 2004.
United States Patent and Trademark Office, Help on the Quick Search Page, visited Oct. 6, 2015.
Van Wyck, David B. et al. "Making Sense: A Scientific Approach to Intravenous Iron Therapy", J Am Soc Nephrol 15: S91-S92, 2004.
Van Zyl-Smit, R., et al., "Experience with the Use of an Iron Polymaltose (Dextrin) Complex Given by Single Total Dose Infusion to Stable Chronic Haemodialysis Patients," Nephron 92, 2002, pp. 316-323.

(56) References Cited

OTHER PUBLICATIONS

Van Zyl-Smit, R., et al., "Experience with the Use of an Iron Polymaltose (Dextrin) Complex Given by Single Total Dose Infusion to Stable Chronic Haemodialysis Patients," Nephron, 2002, Web printout, 4 pages.
Vannotti, A., chairman of Colloquia Geigy on "Iron Deficiency, Pathogenesis• Clinical aspects• Therapy," 1970, 648 pages.
American Regent, "Venofer® (iron sucrose injection, USP) receives FDA approval for the Treatment of Iron Deficiency Anemia in Pre-Dialysis Patients", Press Release, Jun. 17, 2005.
Peter, K et al. "Organic Chemistry Structure and Function", Fifth Edition, Chapter 24, pp. 1096-1138, 2007.
Wallerstein, Ralph O., "Intravenous Iron-Dextran Complex", Blood, vol. 32, No. 4 (Oc-roeER), 1968.
Walters, Brian A. J., "Benchmarking iron dextran sensitivity: reactions requiring resuscitative medication in incident and prevalent patients", Nephrol Dial Transplant (2005) 20: 1438-1442.
Wang, C. et al. "Comparative Risk of Anaphylactic Reactions Associated With Intravenous Iron Products", JAMA. 2015;314(19):2062-2068. doi:10.1001/jama.2015.15572.
Wang, C. et al. "Supplementary Online Content", "Comparative Risk of Anaphylactic Reactions Associated With Intravenous Iron Products", JAMA. 2015;314(19):2062-2068. doi:10.1001/jama.2015.15572.
White, Jr., D.R., et al., "Dextrin characterization by high-performance anion-exchange chromatography-pulsed amperometric detection and size-exclusion chromatography-multi-angle light scattering-refractive index detection," Journal of Chromatography A, 997 (2003) pp. 79-85.
Wikstrom, B., et al., "Iron isomaltoside 1000: a new intravenous iron for treating iron deficiency in chronic kidney disease," J NephroL 2011; 24(05), pp. 589-596.
Woodman, J., et al., "A Surveillance Programme on a Long-established Product:Imferon (Iron Dextran BP)," Pharmaceut. Med. (1987), I, pp. 289-296.
WO2004037865, Certified Translation from German into English, May 27, 2015, 20 pages.
Wu, "Impact of Geographic and Cross-cultural Differences on Spontaneous Adverse Events Reporting," Drug Information Journal, vol. 33, 1999, pp. 921-931.
Yessayan, L., et al., "Intravenous Iron Dextran as a Component of Anemia Management in Chronic Kidney Disease: A Report of Safety and Efficacy," Int J Nephrol. 2013, published on line, 18 pages.
Yessayan, L., et al., "Intravenous Iron Dextran as a Component of Anemia Management in Chronic Kidney Disease: A Report of Safety and Efficacy," International Journal of Nephrology vol. 2013, Article ID 703038, 10 pages.
Zager, R.A., et al., "Parenteral Iron Formulations: A Comparative Toxicologic Analysis and Mechanisms of Cell Injury," American Journal of Kidney Diseases, vol. 40, No. 1 Jul. 2002: pp. 90-103.
Zager, R.A., et al., "Parenteral iron nephrotoxicity: Potential mechanisms and consequences", Kidney International, vol. 66 (2004), pp. 144-156.
Zhang, Z. "Tandem MS can Distinguish Hyaluronic Acid from NAcetylheparosan", J Am Soc Mass Spectrom. Jan. 2008; 19(1): 82-90.
Zolezzi, M., Intravenous Iron Saccharate Complex: Guidelines for its use in the Management of Anemia of Renal Disease, Saudi J. Kidney Dis. Transplant 2003;14(2), pp. 129-133.
Qassim, A., et al. "Safety and Efficacy of Intravenous iron polymaltose, iron sucrose and ferric carboxymaltose in pregnancy: a systematic review," Aust NZ Obstet Gyn, vol. 58, 2018, p. 22-39.
Registry Nos. 4600-00-4 through 12699-98-8. Chemical Abstract Service Registry Handbook—Number Section 1965-1971. American Chemical Society 1974.
United States Patent and Trademark Office Before the Patent Trial and Appeal Board *Pharmacosmos A/S*, Petitioner, v. *American Regent, Inc.*, Patent Owner Case IPR2019-01142, U.S. Pat. No. 8,431,549 Reply to Patent Owner's Preliminary Response.

Report of the ACS Carbohydrate Division Nomenclature Committee, Annual Meeting of the ACS Committee on Nomenclature, Terminology and Symbols. National Meeting in New Orleans, LA, Apr. 7, 2008.
Request for Rehearing Under 37 CFR 42.71(d) dated Jan. 22, 2016 in *Pharmacosmos A/S* v. *Luitpold Pharmaceuticals, Inc.* Case: IPR2015-01493 U.S. Pat. No. 8,431,549.
Response of Petitioner to Board's Dec. 18, 2019 Order Requiring a Showing of Good Cause. Dated Jan. 6, 2020 in *Pharmacosmos A/S* v. *Luitpold Pharmaceuticals, Inc.* Case: IPR2015-01493 U.S. Pat. No. 8,431,549.
Revised Patent Owner Notice of Depostion of Dr. Linhardt, dated Feb. 19, 2016 in *Pharmacosmos A/S* v. *Luitpold Pharmaceuticals, Inc.* Case: IPR2015-01493 U.S. Pat. No. 8,431,549 and IPR2015-01490 U.S. Pat. No. 7,754,702.
Richter, W. "Minimal molecular size of dextran required to elicit heterologous passive cutaneous anaphylaxis in guinea pigs," Int. Arch Allergy 43: 252-268 (1972).
Richter, W. "Effect of substitution on reactivity of B 512 dextran fractions with anti-B 512 dextran in heterologous passive cutaneous anaphylaxis," Int. Archs Allergy appl. Immun vol. 48:502-512 (1975).
Richter, A. W., et al. "Dextran hypersensitivity," Immunology Today, vol. 3, No. 5, 1982, pp. 137-139.
Ritcher, A.W. "Immune Complex Anaphylaxis Induced by Dextran and Its Elimination by Hapten Inhibition", J. Ring et al. (eds.), New Trends in Allergy 11, Springer-Verlag Berlin Heidelberg 1986.
Sofic, E., et al, "Increased iron (111) and total iron content in post mortem substantia nigra of parkinsonian brain", J. Neural Transm (1988) 74:199-205.
Declaration of Ellen C. Reimschneider, dated Feb. 4, 2016.
Rockey, Don C., et al. "Evaluation of the Gastrointestinal Tract in Patients with Iron Deficiency Anemia," Gastrointestinal and Iron Deficient Anemia—Rockey and Cello. vol. 329, No. 23 (1993).
Roe, F.J. C., "On Potential Carcinogenecity of the Iron Macromolecular Complexes", Reprinted from UICC Monograph Series vol. 7: Potential Carcinogenic Hazards from Drugs, Springer-Verlag Berlin • Heidelberg • New York 1967 Printed in Germany / Not a periodical.
Roeser, H.P., et al. "The Role of Ceruloplasmin in Iron Metabolism," Journal of Clinical Investigation, vol. 49, 1970.
Rong, Y., et al. "Determination of dextrose equivalent value and number average molecular weight of maltodextrin by osmometry," Journal of Food Science, vol. 74, No. 1, 2009.
Rosse, Wendell, et al. "The Effect of Iron Therapy in Paroxysmal Nocturnal Hemoglobinuria," Blood. vol. 36, No. 5, Nov. 1970.
Rote List 1996 BPI Service GmbH.
Sabatie, J., et al. "Shear-induced structure in enzymatically-synthesized dextran solutions," Rheol Acta. vol. 25:287-295 (1986).
U.S. Food and Drug Administration, "FDA strengthens warnings and changes prescribing instructions to decrease the risk of serious allergic reactions with anemia drug Feraheme (ferumoxytol)", Safety Announcement, Mar. 30, 2015.
Sax, N. Irving, et al., Hawley's Condensed Chemical Dictionary, eleventh edition, Van Nostrand Reinhold, 1987, pp. 797, 1081-1082.
Sell, Stewart "Chapter 5: Antigenicity and Immunogenicity," Immunology, Immunopathology and Immunity, 4th Ed. 1987 Elsevier Science Publishing.
Shearer, W., et al. "Section A Immunology—Chapter 1: The Immune System," Middleton's Allergy Principles and Practice, 6th Ed. vol. 1, 2003, Mosby.
Shekunov, Boris, et al. "Particle size analysis in pharmaceutics: principles methods and applications," Pharm Res. vol. 24, No. 2, Feb. 2007.
Silverstein, Scott B., et al. "Parenteral Iron Therapy Options," Amer J Hematology. vol. 76:74-78 (2004).
Singh, K. et al., "A comparison between intravenous iron polymaltose complex (Ferrum Hausmann) and oral ferrous fumarate in the treatment of iron deficiency anaemia in pregnancy.", Eur J Haematol. Feb. 1998;60(2):119-24.
Sipe, Jack C., et al. "Brain Iron Metabolism and Neurodegenerative Disorders", Dev Neurosci 2002;24:188-196.

(56) References Cited

OTHER PUBLICATIONS

Sogbanmu, M.O., "Anaemia of pregnancy treated with total dose infusion of iron-polymaltose complex, Teferrol," Current Therapeutic Research, vol. 20, No. 2, Aug. 1976.
St. Peter, Wendy, et al. "Randomized cross over study of adverse reactions and cost implications of intravenous push compared with infusion of iron dextran in hemodialysis patients," Amer J Kidney Diseases, vol. 28, No. 4, Oct. 1996.
Starzynski, R., et al. "Iron supplementation in suckling piglets: How to correct iron deficiency anemia without affecting plasma hepcidin levels," Plos One, vol. 8, No. 5, May 2013. www.plosone.org.
Stryer, Lubert "Chapter 18: Carbohydrates," Biochemistry, 4th Ed. 1995. W.H. Freeman and Co., New York.
Suarez V., Luis, "La Dirsecion del Servicio Quimico Farmaceutico Nacional al senor Ministro", 1960.
Summary of Product, "Ferinject", Jun. 18, 2012.
Sur-Reply to Petitioners Reply to Patent Owner Preliminary Response. *Pharmacosmos A/S* v. *American Regent, Inc.* Case No. IPR2019-01142 U.S. Pat. No. 8,431,549 (Oct. 15, 2019).
Svoboda, M., et al. "Intramuscular versus subcutaneous administration of iron dextran in suckling pigs," Acta. Vet. BRNO (2007) vol. 76: S11-S15.
United States Patent and Trademark Office Before the Patent Trial and Appeal Board *Pharmacosmos A/S* Petitioner, v. *Luitpold Pharmaceuticals, Inc.*, Patent Owner Case IPR2015-01490 U.S. Pat. No. 7,754,702 Patent Owner Mandatory Notices, Date: Jul. 15, 2015.
United States Patent and Trademark Office Before the Patent Trial and Appeal Board *Pharmacosmos A/S* Petitioner, v. *Luitpold Pharmaceuticals, Inc.*, Patent Owner Case IPR2015-01495 U.S. Pat. No. 8,895,612 Patent Owner Mandatory Notices Date: Jul. 15, 2015.
United States Patent and Trademark Office Before the Patent Trial and Appeal Board *Pharmacosmos A/S* Petitioner, v. *Luitpold Pharmaceuticals, Inc.*, Patent Owner. IPR2015-01490; U.S. Pat. No. 7,754,702 B2 Patent Owner Motion to Exclude, Dated: Aug. 9, 2016.
United States Patent and Trademark Office Before the Patent Trial and Appeal Board *Pharmacosmos A/S* Petitioner, v. *Luitpold Pharmaceuticals, Inc.*, Patent Owner. IPR2015-01493; U.S. Pat. No. 8,431,549 B2 Patent Owner Motion to Exclude, Dated: Aug. 9, 2016.
United States Patent and Trademark Office Before the Patent Trial and Appeal Board *Pharmacosmos A/S* Petitioner, v. *Luitpold Pharmaceuticals, Inc.*, Patent Owner Case IPR2015-01493 U.S. Pat. No. 8,431,549 Patent Owner's Notice of Appeal Dated: Mar. 2, 2017.
United States Patent and Trademark Office Before the Patent Trial and Appeal Board *Pharmacosmos A/S* Petitioner, v. *Luitpold Pharmaceuticals, Inc.*, Patent Owner Case IPR2015-01490 U.S. Pat. No. 7,754,702 Patent Owner's Notice of Appeal Dated: Mar. 2, 2017.
United States Patent and Trademark Office Before the Patent Trial and Appeal Board *Pharmacosmos A/S* Petitioner, v. *Luitpold Pharmaceuticals, Inc.*, Patent Owner Case IPR2015-01490 (U.S. Pat. No. 7,754,702 B2) 1 Case IPR2015-01493 (U.S. Pat. No. 8,431,549 B2) Patent Owner Notice of Deposition of Dr. Linhardt Dated: Feb. 17, 2016.
United States Patent and Trademark Office Before the Patent Trial and Appeal Board *Pharmacosmos A/S* Petitioner, v. *Luitpold Pharmaceuticals, Inc.*, Patent Owner IPR2015-01493; U.S. Pat. No. 8,431,549 B2 Patent Owner Notice of Disclaimer Dated: Sep. 27, 2016.
United States Patent and Trademark Office Before the Patent Trial and Appeal Board *Pharmacosmos A/S* Petitioner, v. *Luitpold Pharmaceuticals, Inc.*, Patent Owner IPR2015-01490; U.S. Pat. No. 7,754,702 B2 Patent Owner Notice of Disclaimer Dated: Sep. 27, 2016.
United States Patent and Trademark Office Before the Patent Trial and Appeal Board *Pharmacosmos A/S* Petitioner, v. *Luitpold Pharmaceuticals, Inc.*, Patent Owner Case IPR2015-01493 (U.S. Pat. No. 8,431,549 B2) Patent Owner Objections to Evidence Dated: Jan. 27, 2016.
United States Patent and Trademark Office Before the Patent Trial and Appeal Board *Pharmacosmos A/S* Petitioner, v. *Luitpold Pharmaceuticals, Inc.*, Patent Owner Case IPR2015-01490 (U.S. Pat. No. 7,754,702 B2) Patent Owner Objections to Evidence Dated: Jan. 27, 2016.
United States Patent and Trademark Office Before the Patent Trial and Appeal Board *Pharmacosmos A/S*, Petitioner v. *Luitpold Pharmaceuticals, Inc.*, Patent Owner Cases—IPR2015-01490; U.S. Pat. No. 7,754,702 B2 IPR2015-01493; U.S. Pat. No. 8,431,549 B2 Patent Owner Oral Hearing Demonstratives Dated: Sep. 15, 2016.
United States Patent and Trademark Office Before the Patent Trial and Appeal Board *Pharmacosmos A/S*, Petitioner v. *Luitpold Pharmaceuticals, Inc.*, Patent Owner U.S. Pat. No. 7,754,702 Issue Date: Jul. 13, 2010 Title: Methods and Compositions for Administration of Iron Inter Partes Review No. 2015-01490 Patent Owner Preliminary Response Dated:Oct. 12, 2015.
United States Patent and Trademark Office Before the Patent Trial and Appeal Board *Pharmacosmos A/S*, Petitioner v. *Luitpold Pharmaceuticals, Inc.*, Patent Owner U.S. Pat. No. 8,431,549 Issue Date: Apr. 30, 2013 Title: Methods and Compositions for Administration of Iron Inter Partes Review No. 2015-01493 Patent Owner Preliminary Response Dated: Oct. 12, 2015.
United States Patent and Trademark Office Before the Patent Trial and Appeal Board *Pharmacosmos A/S*, Petitioner v. *Luitpold Pharmaceuticals, Inc.*, Patent Owner U.S. Pat. No. 8,895,612 Issue Date: Nov. 25, 2014 Title: Methods and Compositions for Administration of Iron Inter Partes Review No. 2015-01495 Patent Owner Preliminary Response Dated: Oct. 12, 2015.
United States Patent and Trademark Office Before the Patent Trial and Appeal Board *Pharmacosmos A/S*, Petitioner, v. *American Regent, Inc.*, Patent Owner. Case IPR2019-01 142 U.S. Pat. No. 8,431,549 Patent Owner Preliminary Response Dated: Sep. 19, 2019.
United States Patent and Trademark Office Before the Patent Trial and Appeal Board *Pharmacosmos A/S*, Petitioner v. *Luitpold Pharmaceuticals, Inc.*, Patent Owner IPR2015-01490; U.S. Pat. No. 7,754,702 B2 Patent Owner Reply to Opposition to Motion to Amend Dated: Jul. 19, 2016.
United States Patent and Trademark Office Before the Patent Trial and Appeal Board *Pharmacosmos A/S*, Petitioner v. *Luitpold Pharmaceuticals, Inc.*, Patent Owner IPR2015-01493; U.S. Pat. No. 8,431,549 B2 Patent Owner Reply to Opposition to Motion to Amend Dated: Jul. 19, 2016.
United States Patent and Trademark Office Before the Patent Trial and Appeal Board *Pharmacosmos A/S*, Petitioner v. *Luitpold Pharmaceuticals, Inc.*, Patent Owner IPR-2015-01490; U.S. Pat. No. 7,754,702 B2 Patent Owner Reply to Opposition to Motion to Exclude Dated: Aug. 30, 2016.
United States Patent and Trademark Office Before the Patent Trial and Appeal Board *Pharmacosmos A/S*, Petitioner v. *Luitpold Pharmaceuticals, Inc.*, Patent Owner IPR2015-01493; U.S. Pat. No. 8,431,549 B2 Patent Owner Reply to Opposition to Motion to Exclude Dated: Aug. 30, 2016.
United States Patent and Trademark Office Before the Patent Trial and Appeal Board *Pharmacosmos A/S*, Petitioner v. *Luitpold Pharmaceuticals, Inc.*, Patent Owner IPR2015-01490; U.S. Pat. No. 7,754,702 B2 Patent Owner Request for Oral Argument Date: Aug. 9, 2016.
United States Patent and Trademark Office Before the Patent Trial and Appeal Board *Pharmacosmos A/S*, Petitioner v. *Luitpold Pharmaceuticals, Inc.*, Patent Owner IPR2015-01493; U.S. Pat. No. 8,431,549 B2 Patent Owner Request for Oral Argument Dated: Aug. 9, 2016.
United States Patent and Trademark Office Before the Patent Trial and Appeal Board *Pharmacosmos A/S*, Petitioner v. *Luitpold Pharmaceuticals, Inc.*, Patent Owner IPR2015-01490; U.S. Pat. No. 7,754,702 B2 Patent Owner Response Dated: Mar. 29, 2016.
United States Patent and Trademark Office Before the Patent Trial and Appeal Board *Pharmacosmos A/S*, Petitioner v. *Luitpold Pharmaceuticals, Inc.*, Patent Owner IPR2015-01493; U.S. Pat. No. 8,431,549 B2 Patent Owner Response Dated: Mar. 29, 2016.
United States Patent and Trademark Office Before the Patent Trial and Appeal Board *Pharmacosmos A/S*, Petitioner v. *Luitpold Phar-*

(56) References Cited

OTHER PUBLICATIONS

*maceuticals, Inc.*, Patent Owner Case IPR2015-01493 U.S. Pat. No. 8,431,549 B2 Patent Owner'S Response to Ultra Vires Order (Paper 57) Requiring a Showing of Good Cause Why Claim 15 of U.S. Pat. No. 8,431,549 Should Not be Deemed Unpatentable Dated: Jan. 6, 2020.
United States Patent and Trademark Office Before the Patent Trial and Appeal Board *Pharmacosmos A/S*, Petitioner v. *Luitpold Pharmaceuticals, Inc.*, Patent Owner Case IPR2015-01493 U.S. Pat. No. 8,431,549 B2 Patent Owner Updated Mandatory Notices Dated: Jan. 6, 2020.
Polysaccharide nomenclature (Provisional) Pure Appl. Chem., 1982, vol. 54, No. 8, pp. 1523-1526.
*Pharmacosmos A/S* v. *Luitpold Ex. Pharmaceuticals, Inc.*,Petitioner Ex. 1023—Iron Sorbitol Injection, British Pharmacopoeia Omitted Monograph.
Prakash, Sunil, et al. Experience With a Large Dose (500 Mg) of Intravenous Iron Dextran and Iron Saccharate in Peritoneal Dialysis Patients, Peritoneal Dialysis International, vol. 21, pp. 290-295 (May 2001).
Prince, Martin R., et al. A pilot investigation of new superparamagnetic iron oxide (ferumoxytol) as a contrast agent for cardiovascular MRI, Journal of X-Ray Science and Technology II (2003) 231-240.
Principles and Methods of Sterilization—Principles of Steam Sterilization, Sterilizing Conditions Basis-Temperature Rather Than Pressure, 116-121 (1960).
SPC-Y A460/ AU/E06 Product Information Ferrum H® Injection, Vifor (International) Inc., pp. 1-7 (Jun. 2, 2015).
Petitioner Ex. 1025, Promit(r) (dextran 1) , Consumer Medicine Information, Published by MIMS/myDr Apr. 2005.
Australian Government Department of Health Therapeutic Goods Administration, Public Summary—82435 Ferrosig Injection iron 100mg/2mL (as polymaltose) injection ampoule (Apr. 22, 2002).
Australian Government Department of Health Therapeutic Goods Administration, Public Summary—68110 Ferrum H iron 100mg/2mL (as polymaltose) injection ampoule. Jun. 27, 1999.
Purina Pigemia, 100cc 50 dose (Injectable), Jul. 25, 1968 Ralston Purina Co., St. Louis 2, Missouri.
Papanikolaou, G., et al., Iron metabolism and toxicity, Toxicology and Applied Pharmacology 202 (2005) 199-211.
Parham, Peter, The Immune System, Chapter 1, pp. 1-30 (2000).
Parkin, Jacqueline, et al., An Overview of the Immune System, The Lancet, vol. 357, Jun. 2, 2001, 1777-1789.
United States Patent and Trademark Office Before the Patent Trial and Appeal Board *Pharmacosmos A/S*, Petitioner, v. *American Regent, Inc.*, Patent Owner, Case IPR2019-01142, U.S. Pat. No. 8,431,549 Declaration of Vanessa Park-Thompson in Support of Petitioner Pharmacosmos A/S's Motion for Admission Pro Hac Vice Executed at New York, NY Aug. 20, 2019.
Usher, Thomas C., CA, Patel, Natu, US, Canadian Patent Application No. 2,195,283, Filed: Jan. 16, 1997, Title: Process for Manufacturing Iron Dextran Using Ultrafiltration.
U.K. Provisional Patent Specification 335,965, Application Date: Jun. 5, 1929, Inventor: Carpmael, Arthur, Title: Process for the Manufacture of Complex Lron Compounds.
U.K. Patent Specification 879,441, Application Date: May 26, 1959, No. 17695/59, Date of filing Complete Specification: May 24, 1960, Complete Specification Published: Oct. 11, 1961, Inventor: Michael, Stephen Ernest, et al. Title: Improved Injectable Iron Preparations.
U.K. Patent Specification 918,737, Date of Application and filing Complete Specification: Jun. 18, 1959. Application made in United States of America (No. 762230) on Sep. 22, 1958 Complete Specification Published: Feb. 20, 1963 Applicant: American Cyanamid Company, Title: Colloidal Ferric Hydroxide for Parenteral Administration.
U.K. Patent Specification 748,024, Date of filing Complete Specification: Feb. 23, 1954, Date of Application, Feb. 27, 1953, Complete Specification Published: Apr. 18, 1956 Applicant: Benger's Limited, Title: Improved Therapeutic Preparations of Iron.
U.K. Patent Specification 1377006, Application No. 38214/72, Filed Aug. 16, 1972 Convention Application No. 172865, Filed Aug. 18, 1971 in United States of America, Complete Specification Published Dec. 11, 1974 Applicant: The Central Pharmacal Company, Title: Process for Preparing an Iron-Saccharide Complex.
Peacock, Eileen, et al., Clinical Practice Guidelines for Maintaining Adequate Iron Status With Intravenous Iron Dextran in Hemodialysis Patients, ANNA Journal Jun. 1999 vol. 26 No. 3.
United States Patent and Trademark Office Before the Patent Trial and Appeal Board *Pharmacosmos A/S*, Petitioner v. *Luitpold Pharmaceuticals, Inc.*, Patent Owner. Case IPR2015-01490 (U.S. Pat. No. 7,754,702 B2)1 Case IPR2015-01493 (U.S. Pat. No. 8,431,549 B2) Petitioner's Notice of Deposition of Dr. Adriana Manzi, Dated: Apr. 20, 2016.
United States Patent and Trademark Office Before the PA Tent Trial and Appeal Board *Pharmacosmos A/S*, Petitioner v. *Luitpold Pharmaceuticals, Inc.*, Patent Owner. Case IPR2015-01490 (U.S. Pat. No. 7,754,702 B2)1 Case IPR2015-01493 (U.S. Pat. No. 8,431,549 B2) Petitioner's Corrected Notice of Deposition of Dr. Adriana Manzi, Dated: Apr. 21, 2016.
United States Patent and Trademark Office Before the Patent Trial and Appeal Board *Pharmacosmos A/S*, Petitioner v. *Luitpold Pharmaceuticals, Inc.*, Patent Owner Case IPR2015-01493 U.S. Pat. No. 8,431,549, Petitioner Pharmacosmos A/S's Motion for Pro Hac Vice Admission of Ryan P. Johnson Pursuant to 37 C.F.R. § 42.10(c) Dated: Jan. 6, 2020.
United States Patent and Trademark Office Before the Patent Trial and Appeal Board *Pharmacosmos A/S*, Petitioner, v. *American Regent, Inc.*, Patent Owner Case IPR2019-01142 U.S. Pat. No. 8,431,549, Petitioner Pharmacosmos A/S's Motion for Pro Hac Vice Admission of Ryan P. Johnson Pursuant to 37 C.F.R. § 42.10(c) Dated: Aug. 20, 2019.
United States Patent and Trademark Office Before the Patent Trial and Appeal Board *Pharmacosmos A/S*, Petitioner, v. *American Regent, Inc.*, Patent Owner, Case IPR2019-01142 U.S. Pat. No. 8,431,549, Petitioner Pharmacosmos A/S's Motion for Pro Hac Vice Admission of Vanessa Park-Thompson Pursuant to 37 C.F.R. § 42.10(c)) Dated: Aug. 20, 2019.
United States Patent and Trademark Office Before the Patent Trial and Appeal Board *Pharmacosmos A/S*, Petitioner v. *Luitpold Pharmaceuticals, Inc.*, Patent Owner, Case IPR2015-01493 U.S. Pat. No. 8,431,549 B2 Petitioner's Motion for Withdrawal of Counsel Dated: Dec. 19, 2019.
United States Patent and Trademark Office Before the Patent Trial and Appeal Board *Pharmacosmos A/S*, Petitioner v. *Luitpold Pharmaceuticals, Inc.*, Patent Owner. Case IPR2015-01490 U.S. Pat. No. 7,754,702 B2 Petitioner Pharmacosmos A/S's Notice of Cross-Appeal, Dated: Mar. 8, 2017.
United States Patent and Trademark Office Before the Patent Trial and Appeal Board *Pharmacosmos A/S*, Petitioner v. *Luitpold Pharmaceuticals, Inc.*Patent Owner IPR2015-01490; U.S. PAt. No. 7,754,702 B2 IPR2015-01493; U.S. Pat. No. 8,431,549 B2 Petitioner's Notice of Demonstrative Exhibits, Dated: Sep. 15, 2016.
United States Patent and Trademark Office Before the Patent Trial and Appeal Board *Pharmacosmos A/S*, Petitioner v. *Luitpold Pharmaceuticals, Inc.*, Patent Owner. Cases—IPR2015-01490; U.S. Pat. No. 7,754,702 B2 IPR2015-01493; U.S. Pat. No. 8,431,549 B2 Petitioner's Notice of Objections to Evidence, Dated: Apr. 5, 2016.
United States Patent and Trademark Office Before the PA Tent Trial and Appeal Board *Pharmacosmos A/S*, Petitioner v. *Luitpold Pharmaceuticals, Inc.*Patent Owner Cases—IPR2015-01490; U.S. Pat. No. 7,754,702 B2 IPR2015-01493; U.S. Pat. No. 8,431,549 B2 IPR2015-01495; U.S. Pat. No. 8,895,612 B2, Petitioner's Objection to Patent Owner Response in Lieu of Motion (to Patent Owner Response in Lieu of Motion, Paper 9) , Dated: Oct. 30, 2015.
United States Patent and Trademark Office Before the PA Tent Trial and Appeal Board *Pharmacosmos A/S*, Petitioner v. *Luitpold Pharmaceuticals, Inc.*, Patent Owner Cases—IPR2015-01490; U.S. Pat. No. 7,754,702 B2 IPR2015-01493; U.S. Pat. No. 8,431,549 B2 Petitioner's Objections to Patent Owner'S Demonstrative Exhibits, Dated: Sep. 20, 2016.
United States Patent and Trademark Office Before the Patent Trial and Appeal Board *Pharmacosmos A/S*, Petitioner v. *Luitpold Phar-*

(56) References Cited

OTHER PUBLICATIONS maceuticals, Inc., Patent Owner U.S. Pat. No. 7,754,702 Title: Methods and Compositions for Administration of Iron Inter Partes Review No. 2015-01490 Petitioner's Opposition to Patent Owner's Motion to Exclude, Dated: Aug. 23, 2016.
United States Patent and Trademark Office Before the Patent Trial and Appeal Board *Pharmacosmos A/S*, Petitioner v. *Luitpold Pharmaceuticals, Inc.*, Patent Owner. IPR2015-01493; U.S. Pat. No. 8,431,549 B2 Petitioner's Opposition to Patent Owner's Motion to Amend, Dated: Jun. 20, 2016.
United States Patent and Trademark Office Before the PA Tent Trial and Appeal Board *Pharmacosmos A/S*, Petitioner v. *Luitpold Pharmaceuticals, Inc.*, Patent Owner. IPR2015-01490; U.S. Pat. No. 7,754,702 B2 Petitioner's Reply to Patent Owner Response, Dated: Jun. 20, 2016.
United States Patent and Trademark Office Before the PA Tent Trial and Appeal Board *Pharmacosmos A/S*, Petitioner v. *Luitpold Pharmaceuticals, Inc.*, Patent Owner. IPR2015-01493; U.S. Pat. No. 8,431,549 B2 Petitioner's Reply to Patent Owner Response, Dated: Jun. 20, 2016.
United States Patent and Trademark Office Before the PA Tent Trial and Appeal Board *Pharmacosmos A/S*, Petitioner v. *Luitpold Pharmaceuticals, Inc.*, Patent Owner U.S. Pat. No. 7,754,702, Title: Methods and Compositions for Administration of Iron Inter Partes Review No. 2015-01490, Petitioner's Request for Oral Argument, Dated: Aug. 9, 2016.
United States Patent and Trademark Office Before the PA Tent Trial and Appeal Board *Pharmacosmos A/S*, Petitioner v. *Luitpold Pharmaceuticals, Inc.*, Patent Owner U.S. Pat. No. 8,431,549 Title: Methods and Compositions for Administration of Iron Inter Partes Review No. 2015-01493 Petitioner's Request for Oral Argument, Dated: Aug. 9, 2016.
United States Patent and Trademark Office Before the Patent Trial and Appeal Board *Pharmacosmos A/S*, Petitioner v. *Luitpold Pharmaceuticals, Inc.*, Patent Owner. Case No. IPR2015-01493 U.S. Pat. No. 8,431,549 Petitioner's Revocation of Power of Attorney and New Power of Attorney Pursuant to 37 C.F.R. §42.10(b) Dated: Dec. 30, 2019.
United States Patent and Trademark Office Before the Patent Trial and Appeal Board *Pharmacosmos A/S*, Petitioner v. *Luitpold Pharmaceuticals, Inc.*, Patent Owner IPR2015-01493; U.S. Pat. No. 8,431,549 B2 Petitioner's Sur-Reply Responding to PA Tent Owner's Reply to Opposition to Motion to Amend. Dated: Jul. 29, 2016.
United States Patent and Trademark Office Before the Patent Trial and Appeal Board *Pharmacosmos A/S*, Petitioner v. *Luitpold Pharmaceuticals, Inc.*, Patent Owner. PR2015-01490; U.S. Pat. No. 7,754,702 B2 Petitioner's Sur-Reply Responding to Patent Owner's Reply to Opposition to Motion to Amend Dated: Jul. 29, 2016.
United States Patent and Trademark Office Before the Patent Trial and Appeal Board *Pharmacosmos A/S*, Petitioner v. *Luitpold Pharmaceuticals, Inc.*, Patent Owner. IPR2015-01493 U.S. Pat. No. 8,431,549 Petitioner Pharmacosmos A/S's Updated Exhibit List as of Jan. 6, 2020, Dated: Jan. 6, 2020.
United States Patent and Trademark Office Before the Patent Trial and Appeal Board *Pharmacosmos A/S*, Petitioner v. *Luitpold Pharmaceuticals, Inc.*, Patent Owner. Case No. IPR2015-01493 U.S. Pat. No. 8,431,549 Petitioner's Updated Mandatory Notice Information Under 37 C.F.R. §42.8 Date: Dec. 30, 2019.
United States Patent and Trademark Office Before the Patent Trial and Appeal Board *Pharmacosmos A/S*, Petitioner v. *Luitpold Pharmaceuticals, Inc.*, Patent Owner. Petition for Inter Partes Review of U.S. Pat. No. 7,754,702.
United States Patent and Trademark Office Before the Patent Trial and Appeal Board *Pharmacosmos A/S*, Petitioner v. *Luitpold Pharmaceuticals, Inc.*, Patent Owner. Petition for Inter Partes Review of U.S. Pat. No. 8,431,549.
United States Patent and Trademark Office Before the Patent Trial and Appeal Board *Pharmacosmos A/S*, Petitioner, v. *American Regent, Inc.*, Patent Owner. Petition for Inter Partes Review of U.S. Pat. No. 8,431,549.

United States Patent and Trademark Office Before the Patent Trial and Appeal Board *Pharmacosmos A/S*, Petitioner, v. *American Regent, Inc.*, Patent Owner. Case No. PGR2020-00009 U.S. Pat. No. 10,478,450 Petition for Post Grant Review Dated: Jan. 6, 2020.
*Pharmacosmos A/S* v. *American Regent, Inc.* Petitioner Ex. 1027— Highlights of Prescribing Information Injectafer® (ferric carboxymaltose injection), for intravenous use Initial U.S. Approval: 2013.
*Pharmacosmos A/S* v. *American Regent, Inc.* Petitioner Ex. 1053— Ernster, Lars, Iron overload: molecular clues to its cause TIBS May 24, 1999 164-166.
United States Patent and Trademark Office Before the Patent Trial and Appeal Board *Pharmacosmos A/S*, Petitioner, v. *American Regent, Inc.*, Patent Owner. Case PGR2020-00009 U.S. Pat. No. 10,478,450, Mailed: Jan. 17, 2020 Before Steven M. Amitrani, Trial Paralegal, Notice of Filing Date Accorded to Petition and Time for Filing Patent Owner Preliminary Response.
Physcians Desk Reference 36th Edition, 1982, Fisons Corporation 920-925.
Physcians Desk Reference 55th Edition, 2001, INFeD® Uron Dextran Injection,, USP) 2879-2881.
Physcians Desk Reference 56th Edition, 2002, American Regent Laboratories, Inc, Venofer®.
United States Patent and Trademark Office Before the Patent Trial and Appeal Board *Pharmacosmos A/S*, Petitioner v. *Luitpold Pharmaceuticals, Inc.*, Patent Owner. IPR2015-01490; U.S. Pat. No. 7,754,702 B2 Patent Owner Certificate of Service.
United States Patent and Trademark Office Before the Patent Trial and Appeal Board *Pharmacosmos A/S*, Petitioner v. *Luitpold Pharmaceuticals, Inc.*, Patent Owner. IPR2015-01493; U.S. Pat. No. 8,431,549 B2 Patent Owner Exhibit List as of March 29, 2016.
United States Patent and Trademark Office Before the Patent Trial and Appeal Board *Pharmacosmos A/S*, Petitioner v. *Luitpold Pharmaceuticals, Inc.*, Patent Owner. IPR2015-01490; U.S. Pat. No. 7,754,702 B2 Patent Owner Exhibit List as of July 19, 2016.
United States Patent and Trademark Office Before the Patent Trial and Appeal Board *Pharmacosmos A/S*, Petitioner v. *Luitpold Pharmaceuticals, Inc.*, Patent Owner. IPR2015-01493; U.S. Pat. No. 8,431,549 B2 Patent Owner Exhibit List as of Jan. 6, 2020.
United States Patent and Trademark Office Before the Patent Trial and Appeal Board *Pharmacosmos A/S*, Petitioner v. *Luitpold Pharmaceuticals, Inc.*, Patent Owner Case IPR2015-01493 U.S. Pat. No. 8,431,549 Patent Owner Mandatory Notices, Date: Jul. 15, 2015.
United States Patent and Trademark Office Before the Patent Trial and Appeal Board *Pharmacosmos A/S* Petitioner, v. *American Regent, Inc.*, Patent Owner Case IPR2015-01493 U.S. Pat. No. 8,431,549 Patent Owner Mandatory Notices, Date: Jul. 15, 2015.
Kumpf, V., et al. Parenteral Iron Dextran Therapy. DICP The Annals of Pharmacotherapy, vol. 24, Feb. 1990.
Kulnigg, S. et al. A Novel Intravenous Iron Formulation for Treatment of Anemia in Inflammatory Bowel Disease: The Ferric Carboxymaltose (FERINJECT®) Randomized Controlled Trial. American Journal of Gastroenterolgy, 2008.
Lam-Po-Tang, M., et al. Icodextrin Hypersensitivity in a CAPD Patient. Peritoneal Dialysis International. Retrieved from Internet website URL: http:/www.pdiconnect.com on Mar. 25, 2016.
Lawrence, R. Development and Comparison of Iron Dextran Products. PDA Journal of Pharmaceutical Science and Technology, vol. 52, pp. 190-197 (1998).
Declaration Under 37 CFR 1.132 of Richard Lawrence, dated Dec. 5, 2012, as filed in U.S. Appl. No. 12/787,283 (Helenek) filed on May 25, 2010.
Lemley, M., et al. Divided Infringement Claims. AIPLA Quarterly Journal, vol. 33, No. 3, Summer 2005.
Leone, R., et al. Drug-Induced Anaphylaxis—Case/Non-case Study Based on an Italian Pharmacovigilance Database. Drug Safety, vol. 28, No. 6 (2005) 547-556.
Lewis, R. G. Practical Guide to Autoclave Validation. Pharmaceutical Engineering. Jul./Aug. 2002.
Deposition of Robert Linhardt, Ph.D. Mar. 2, 2016. In the USPTO, Before the Patent Trial and Appeal Board, *Pharmacosmos A/S* v. *Luitpold Pharmaceuticals, Inc.* Case Nos. IPR2015-01490 (U.S. Pat. No. 7,754,702) and IPR2015-01493 (U.S. Pat. No. 8,431,549).

(56) References Cited

OTHER PUBLICATIONS

Lindvall, S., et al. Studies on a New Intramuscular Haematinic, Iron-Sorbitol. British Journal of Pharmacology. vol. 17. 358-371 (1961).

Linhardt, R. J. Production and Chemical Processing of Low Molecular Weight Heparins. Seminars in Thrombosis and Hemostasis. vol. 25, Suppl. 3, 1999.

Curriculum Vitae. Robert J. Linhardt, Ph. D. 115 pages.

Declaration of Robert Linhardt, Ph.D. dated Jun. 22, 2015 with Curriculum Vitae. In the USPTO, Before the Patent and Trial Appeal Board, *Pharmacosmos A/S* v. *Luitpold Pharmaceuticals, Inc.* Case Unassigned (U.S. Pat. No. 8,431,549).

Expert Declaration of Robert Linhardt, Ph.D. dated Jun. 13, 2019 with Appendix A: Materials Considered. In the USPTO, Before the Patent Trial and Appeal Board, *Pharmacosmos A/S* v. *American Regent, Inc.* Case No. IPR2019-01142 (U.S. Pat. No. 8,431,549).

Declaration of Robert Linhardt, Ph.D. dated Jun. 17, 2015 with Curriculum Vitae. In the USPTO, Before the Patent and TrialAppeal Board, *Pharmacosmos A/S* v. *Luitpold Pharmaceuticals, Inc.* Case Unassigned (U.S. Pat. No. 7,754,702).

Fisons' Opticrom, Imferon May be Off U.S. Market Until Late 1992 as the Company Upgrades U.K. Manufacturing Plant to Meet FDA Quality Control Concerns. The Pink Sheet. Pharma Intelligence Informa. Retrieved from the Internet from website URL: https://www.pharm am edtechbi .com/publications/the-pi nk-sheet/53/051 on Jun. 13, 2016.

London, E. The Molecular Formula and Proposed Structure of the Iron-Dextran Complex, IMFERON, Journal of Pharmaceutical Sciences, vol. 93, No. 7, Jul. 2004, published online in Wiley InterScience (www.interscience.wiley.com).

Document 42, Case 17-1715. Brief of Appellant Luitpold Pharmaceuticals, Inc., United States Court of Appeals for the Federal Circuit, *Luitpold Pharmaceuticals, Inc.*, Appellant v. *Pharmacosmos A/S*, Cross-Appellant. Appeal from the United States Patent and Trademark Office, Patent Trial and Appeal Board in Inter Partes Review IPR 2015-01493 and IPR 2015-01490, Filed Jul. 27, 2017.

Document 53, Case 17-1715. Corrected Response and Reply Brief of Appellant, Luitpold Pharmaceuticals, Inc., United States Court of Appeals for the Federal Circuit, *Luitpold Pharmaceuticals, Inc.*, Appellant v. *Pharmacosmos A/S*Cross-Appellant. Appeal from the United States Patent and Trademark Office, Patent Trial and Appeal Board in Inter Partes Review IPR 2015-01493 and IPR 2015-01490, Filed Oct. 30, 2017.

Luitpold Pharmaceuticals—Executive Bios—Mary Jane Helenek, President and CEO, Luitpold Pharmaceuticals, Inc. retrieved from the Internet webpage URL: http://www.luitpold.com/ExecutiveBios.aspx on Oct. 7, 2015.

Lynch, R.E., et al. The Anemia of Vitamin E Deficiency in Swine: An Experimental Model of the Human Congenital Dyserythropoietic Anemias. American Journal of Hematology, vol. 2; 145-158; 1977.

Lyseng-Williamson, K. A., et al. Ferric Carboxymaltose. A Review of its Use in Iron-Deficiency Anaemia. Drugs 2009; vol. 69, No. 6; 739-756.

Macdougall, I. C., et al. Complement Activation-Related Pseudo-Allergy: A Fresh Look at Hypersensitivity Reactions to Intravenous Iron. Amer. Journal Nephrol 2017; vol. 45; 60-62 published online Nov. 29, 2016.

Macdougall, I. C. Intravenous administration of iron in epoetin-treated haemodialysis patients—which drugs, which regimen? Nephrol Dial Transplant (2000) 15: 1743-1745.

Macdougall, I. C. Evolution of IV Iron Compounds Over the Last Century. Journal of Renal Care. 2009. European Dialysis and Transplant Nurses Association/ European Renal Care Association.

Mackay, Ian R., et al. Advances in Immunology. The New England Journal of Medicine, vol. 344, No. 14, Apr. 5, 2001. www.nejm.org.

Maltodextrine (definition). Excerpt from Rompp Lexikon Chemie 1998.

Mamula, P., et al. Total Dose Intravenous Infusion of Iron Dextran for Iron-Deficiency Anemia in Children with Inflammatory Bowel Disease. Journal of Pediatric Gastroenterology and Nutrition, vol. 34; 286-290, Mar. 2002.

Resume/Curriculum Vitae. Adriana E. Manzi, PhD., Managing Director/Technical Consulting Group, Athelninc. 12 pgs.

Declaration of Dr. Adriana Manzi. In the United States Patent and Trademark Office, Before the Patent Trial and Appeal Board, *Pharmacosmos A/S*, Petitioner, v. *Luitpold Pharmaceuticals, Inc.*, Patent Owner, Case Nos. IPR2015-01490 (U.S. Pat. No. 7,754,702) and IPR2015-01493 (U.S. Pat. No. 8,431,549) dated Mar. 29, 2016.

Corrected Declaration of Dr. Adriana Manzi. In the United States Patent and Trademark Office, Before the Patent Trial and Appeal Board, *Pharmacosmos A/S*, Petitioner, v. *Luitpold Pharmaceuticals, Inc.*, Patent Owner, Case Nos. IPR2015-01490 (U.S. Pat. No. 7,754,702) and IPR2015-01493 (U.S. Pat. No. 8,431,549) dated Apr. 21, 2016.

Transcript of Video Deposition of Adriana Manzi, PhD. May 12, 2016. in the United States Patent and Trademark Office, Before the Patent Trial and Appeal Board, *Pharmacosmos A/S*, Petitioner, v. *Luitpold Pharmaceuticals, Inc.*, Patent Owner, Case Nos. IPR2015-01490 (U.S. Pat. No. 7,754,702) and IPR2015-01493 (U.S. Pat. No. 8,431,549).

Errata—Corrections on Transcript of Video Deposition of Adriana Manzi, PhD. May 12, 2016. Dated Jun. 3, 2016.

Marcy, R. et al. Injectable Ferric Hydroxide Polymaltose: I. Investigation of the Acute Toxicity of High and Very High Dosages in Rats and Mice. IRCS Medical Science: Drug Metabolism and Toxicology: Hematology: Pharmacology, vol. 5, p. 255 (1977).

McMurry, John. 4.9 Addition of Radicals to Alkenes: Polymers. Fundamentals of Organic Chemistry, 5th Edition. 2003.

McNaught, Alan D. Nomenclature of Carbohydrates (Recommendations 1996). Pure Applied Chemistry, vol. 68, No. 10, pp. 1919-2008,1996.

Mehmood, T., et al. Response to intravenous iron in patients with iron deficiency anemia (IDA) and restless leg syndrome (Willis-Ekbom disease). Sleep Medicine, vol. 14; pp. 1473-1476 (2014).

Meier T, Schropp P, Pater C, Leoni AL, Van VKT, Elford P. Physicochemical and toxicological characterization of a new generic iron sucrose preparation. Arzneimittel-Forsch. 2011; 61 (2):112-119.

Excerpt from Merrian Webster's Collegiate Dictionary, Eleventh Edition, 2005.

Mocan, H., et al. Breath holding spells in 91 children and response to treatment with iron. Arch Dis Child. vol. 81, pp. 261-262, Sep. 1999.

Monofer Summary of Product Characteristics. Pharmacosmos A/S, Holbaek, Denmark, Mar. 10, 2014.

Moore, A., et al. Uptake of Dextran-Coated Monocrystalline Iron Oxides in Tumor Cells and Macrophages. JMRI vol. 7, No. 6, Nov./Dec. 1997.

Moride, Y., et al. Under-reporting of adverse drug reactions in general practice. Br J Clin Pharmacol 1997; 43: 177-181.

Morris, E., et al. Conformation and Intermolecular Interactions of Carbohydrate Chains. Journal of Supramolecular Structure 6: 259-274 (1977).

Morton, D. B., et al. Refining procedures for the administration of substances. Report of the BVAAWF/FRAME/RSPCA/UFAW Joint Working Group on Refinement. Laboratory Animals Ltd. Laboratory Animals (2001) 35, 1-41.

Motion to Amend. United States Patent and Trademark Office. Before the PA Tent Trial and Appeal Board. *Pharmacosmos A/S*, Petitioner, v. *Luitpold Pharmaceuticals, Inc.*, Patent Owner. Case No. IPR2015-01490; U.S. Pat. No. 7,754,702 B2. Served Mar. 29, 2016.

Motion to Amend. United States Patent and Trademark Office. Before the PA Tent Trial and Appeal Board. *Pharmacosmos A/S*, Petitioner, v. *Luitpold Pharmaceuticals, Inc.*, Patent Owner. Case No. IPR2015-01493; U.S. Pat. No. 8,431,549 B2. Served Mar. 29, 2016.

Manuel Munoz & Elisa Martfn-Montafiez (2012) Ferric carboxymaltose for the treatment of iron-deficiency anemia, Expert Opinion on

(56) References Cited

OTHER PUBLICATIONS

Pharmacotherapy, 13:6, 907-921, DOI: 10.1517/14656566.2012. 669373 To link to this article: https://doi.org/10.1517/14656566. 2012.669373.

Nagpal, J. et al. Iron Formulations in Pediatric Practice. Indian Pediatrics 2004; 41:807-815.

National Kidney Foundation. K/DOQI Clinical Practice Guidelines for Anemia of Chronic Kidney Disease, 2000. Am J Kidney Dis 3 7 :S 182-S23 8, 2001 (suppl 1).

Paper 8. Order Conduct of the Proceeding 37 C.F.R. § 42.5. United States Patent and Trademark Office Before the Patent Trial and Appeal Board. *Pharmacosmos A/S*, Petitioner, v. *Luitpold Pharmaceuticals, Inc.*, Patent Owner. Cases1 IPR2015-01490; U.S. Pat. No. 7,754,702 B2; IPR2015-01493; U.S. Pat. No. 8,431,549 B2; IPR2015-01495; U.S. Pat. No. 8,895,612 B2. Entered: Oct. 14, 2015.

Paper 17. Amendment to Scheduling Order. United States Patent and Trademark Office Before the Patent Trial and Appeal Board. *Pharmacosmos A/S*, Petitioner, v. *Luitpold Pharmaceuticals, Inc.*, Patent Owner. Cases1 IPR2015-01490; U.S. Pat. No. 7,754,702 B2; IPR2015-01493; U.S. Pat. No. 8,431,549 B2. Entered: Feb. 17, 2016.

Paper 21. Order Conduct of the Proceeding 37 C.F.R. § 42.5. United States Patent and Trademark Office Before the Patent Trial and Appeal Board. *Pharmacosmos A/S*, Petitioner, v. *Luitpold Pharmaceuticals, Inc.*, Patent Owner. Cases1 IPR2015-01490; U.S. Pat. No. 7,754,702 B2; IPR2015-01493; U.S. Pat. No. 8,431,549 B2. Entered: Mar. 11, 2016.

Paper 45. Order Conduct of the Proceeding 37 C.F.R. § 42.5. United States Patent and Trademark Office Before the Patent Trial and Appeal Board. *Pharmacosmos A/S*, Petitioner, v. *Luitpold Pharmaceuticals, Inc.*, Patent Owner. Cases1 IPR2015-01490; U.S. Pat. No. 7,754,702 B2; IPR2015-01493; U.S. Pat. No. 8,431,549 B2. Entered: Aug. 19, 2016.

Paper 46. Order Trial Hearing 37 C.F.R. § 42.70. United States Patent and Trademark Office Before the Patent Trial and Appeal Board. *Pharmacosmos A/S*, Petitioner, v. *Luitpold Pharmaceuticals, Inc.*, Patent Owner. Cases1 IPR2015-01490; U.S. Pat. No. 7,754,702 B2; IPR2015-01493; U.S. Pat. No. 8,431,549 B2. Entered: Aug. 22, 2016.

Paper 53. Record of Oral Hearing. United States Patent and Trademark Office Before the Patent Trial and Appeal Board. *Pharmacosmos A/S*, Petitioner, v. *Luitpold Pharmaceuticals, Inc.*, Patent Owner. Cases1 IPR2015-01490; U.S. Pat. No. 7,754,702 B2; IPR2015-01493; U.S. Pat. No. 8,431,549 B2. Entered: Nov. 3, 2016.

Paper 12. Scheduling Order. United States Patent and Trademark Office Before the Patent Trial and Appeal Board. *Pharmacosmos A/S*, Petitioner, v. *Luitpold Pharmaceuticals, Inc.*, Patent Owner. Cases1 IPR2015-01490; U.S. Pat. No. 7,754,702 B2; IPR2015-01493; U.S. Pat. No. 8,431,549 B2. Entered: Jan. 8, 2016.

Paper 22. Order Conduct of the Proceeding 37 C.F.R. § 42.5. United States Patent and Trademark Office Before the Patent Trial and Appeal Board. *Pharmacosmos A/S*, Petitioner, v. *Luitpold Pharmaceuticals, Inc.*, Patent Owner. Cases1 IPR2015-01490; U.S. Pat. No. 7,754,702 B2; IPR2015-01493; U.S. Pat. No. 8,431,549 B2. Entered: Mar. 11, 2016.

Paper 4. Notice of Filing Date Accorded to Petition and Time for Filing Patent Owner Preliminary Response. United States Patent and Trademark Office Before the Patent Trial and Appeal Board. *Pharmacosmos A/S*, Petitioner, v. *Luitpold Pharmaceuticals, Inc.*, Patent Owner. Case IPR2015-01493; U.S. PAt. No. 8,431,549 B2. Mailed: Jul. 10, 2015.

Paper 11. Decision Institution of Inter Partes Review 37 C.F.R. § 42.108. United States Patent and Trademark Office Before the Patent Trial and Appeal Board. *Pharmacosmos A/S*, Petitioner, v. *Luitpold Pharmaceuticals, Inc.*, Patent Owner. Case IPR2015-01493; U.S. Pat. No. 8,431,549 B2. Entered: Jan. 8, 2016.

Paper 21. Decision Denying Petitioner's Request for Rehearing 37 C.F.R. § 42. 71 (d). United States Patent and Trademark Office Before the Patent Trial and Appeal Board. *Pharmacosmos A/S*, Petitioner, v. *Luitpold Pharmaceuticals, Inc.*, Patent Owner. Case IPR2015-01493; U.S. Pat. No. 8,431,549 B2. Entered: Feb. 26, 2016.

Paper 54. Final Written Decision 35 USC.§ 318(a) and 37 C.FR. § 42.73. United States Patent and Trademark Office Before the Patent Trial and Appeal Board. *Pharmacosmos A/S*, Petitioner, v. *Luitpold Pharmaceuticals, Inc.*, Patent Owner. Case IPR2015-01493; U.S. Pat. No. 8,431,549 B2. Entered: Dec. 28, 2016.

Paper 56. Panel Change Order Conduct of the Proceedings 37 C.F.R. § 42.5. United States Patent and Trademark Office Before the Patent Trial and Appeal Board. *Pharmacosmos A/S*, Petitioner, v. *Luitpold Pharmaceuticals, Inc.*, Patent Owner. Case IPR2015-01493; U.S. Pat. No. 8,431,549 B2. Entered: Dec. 18, 2019.

Paper 57. Order Conduct of the Proceeding—Requiring a Showing of Good Cause Why Claim 15 Should Not Be Deemed Unpatentable 37 C.F.R. § 42.5(a). United States Patent and Trademark Office Before the Trial and Appeal Board. *Pharmacosmos A/S*, Petitioner, v. *Luitpold Pharmaceuticals, Inc.*, Patent Owner. Case IPR2015-01493; U.S. Pat. No. 8,431,549 B2. Entered: Dec. 18, 2019.

Paper 59. Order Conditionally Granting Petitioner's Unopposed Motion to Withdraw and Substitute Counsel 37 C.F.R. § 42.10. United States Patent and Trademark Office Before the Patent Trial and Appeal Board. *Pharmacosmos A/S*, Petitioner, v. *Luitpold Pharmaceuticals, Inc.*, Patent Owner. Case IPR2015-01493; U.S. Pat. No. 8,431,549 B2. Entered: Dec. 23, 2019.

Paper 4. Notice of Filing Date Accorded to Petition and Time for Filing Patent Owner Preliminary Response. United States Patent and Trademark Office Before the Patent Trial and Appeal Board. *Pharmacosmos A/S*, Petitioner, v. *Luitpold Pharmaceuticals, Inc.*, Patent Owner. Case IPR2015-01495; U.S. Pat. No. 8,895,612 B2. Mailed Jul. 10, 2015.

Paper 11. Decision Denying Institution of Inter Partes Review 37 C.F.R. § 42.108. United States Patent and Trademark Office Before the Patent Trial and Appeal Board. *Pharmacosmos A/S*, Petitioner, v. *Luitpold Pharmaceuticals, Inc.*, Patent Owner. Case IPR2015-01495; U.S. Pat. No. 8,895,612 B2. Entered Jan. 8, 2016.

Paper 3. Notice of Filing Date Accorded to Petition and Time for Filing Patent Owner Preliminary Response. United States Patent and Trademark Office Before the Patent Trial and Appeal Board. *Pharmacosmos A/S*, Petitioner, v. *American Regent, Inc.*, Patent Owner. Case IPR2015-01492; U.S. Pat. No. 8,431,549 B2. Mailed: Jun. 19, 2019.

Paper 9. Order Granting Petitioner's Motions for Pro Hae Vice Admission of Vanessa Park-Thompson and Ryan P. Johnson 37 C.F.R. § 42.10. United States Patent and Trademark Office Before the Patent Trial and Appeal Board. *Pharmacosmos A/S*, Petitioner, v. *American Regent, Inc.*, Patent Owner. Case IPR2015-01492; U.S. Pat. No. 8,431,549 B2. Entered: Sep. 18, 2019.

Paper 13. Decision Denying Institution of Inter Partes Review 35 U.S.C. § 314 United States Patent and Trademark Office Before the Patent Trial and Appeal Board. *Pharmacosmos A/S*, Petitioner, v. *American Regent, Inc.*, Patent Owner. Case IPR2015-01492; U.S. Pat. No. 8,431,549 B2. Entered: Dec. 18, 2019.

NDA No. 40-024/S-022. Description and Prescribing Information. Dexferrum® (Iron Dextran Injection, USP) Rx Only. U.S. Pat. No. 5,624,668. American Regent, Inc. Shirley, NY 11967. Aug. 2008.

Guidelines for Administration of IV Iron Polymaltose in Chronic Kidney Disease Via Continuous Intravenous Infusion. Royal Perth Hospital Anaemia Co-ordinator Guidelines for Administration of Iron Polymaltose, Mar. 2002.

Iron Sorbitol Injection.doc. PB Monograph Template. British Pharmacopoeia Omitted Monograph.

Crighton, Robert R., et al. Chapter 7: Iron Therapy. Iron Therapy with Special Emphasis on Intravenous Administration. First Edition. 1996.

U.S. Appl. No. 12/787,283, filed May 25, 2010, now U.S. Pat. No. 8,431,549, issued Apr. 30, 2013.

U.S. Appl. No. 14/100,717, filed Dec. 9, 2013, now U.S. Pat. No. 8,895,612, issued Nov. 25, 2014.

Iron Corner: IV Iron Products. Society for the Advancement of Blood Management, Inc. Englewood, New Jersey. Nov. 2013.

Excerpt from "Iron and Erythrocytes in Dialysis Patients," J Am Soc Nephrol. 14:2003, p. 705A.

(56) References Cited

OTHER PUBLICATIONS

Jacobs, P., et al. "Comparative Bioavailability of Ferric Polymaltose and Ferrous Sulphate in Iron-Deficient Blood Donors," Journal of Clinical Apheresis. 8:89-95 (1993) Wiley-Liss, Inc.
Jankiewicz, B., et al. "Electrochemical Oxidation of Low Molecular Dextran" Chemia Stosowana XXXII, 2, 293-299 (1988).
Jayaseelan, T., et al. "Cost comparison, efficacy and safety of intravenous iron infusion versus push in maintenance haemodialysis patients in a tertiary care centre," Indian Journal of Nephrology, vol. 15, pp. 232-234, 2005.
Jeanes, A. et al. "Molecular Association in Dextran and in Branched Amylaceous Carbohydrates," Journal of Biological Chemistry, vol. 176: 617-627, 1948.
Johnson, G., et al. "Bioavailability and the Mechanisms of Intestinal Absorption of Iron from Ferrous Ascorbate and Ferric Polymaltose in Experimental Animals," Exp. Hematol. vol. 18;1064-1069 (1990).
Declaration of Ryan P. Johnson in Support of Petitioner Pharmacosmos A/S's Motion for Admission Pro Hac Vice. United States Patent and Trademark Office Before the Patent Trial and Appeal Board. *Pharmacosmos A/S*, Petitioner, v. *American Regent, Inc.*, Patent Owner. Case IPR2015-01492; U.S. Pat. No. 8,431,549 B2. Aug. 20, 2019.
Lee Josephson, Reading, MA. Curriculum Vitae.
Declaration of Lee Josephson. United States Patent and Trademark Office Before the Patent Trial and Appeal Board. *Pharmacosmos A/S*, Petitioner, v. *American Regent, Inc.*, Patent Owner. Case PGR2020-00009; U.S. Pat. No. 10,478,450 B2.
Kabat, E., et al. Dextran—An Antigen in Man. Journal of Immunology, vol. 70, Baltimore MD, 1953.
Kabat, E., et al. The Effect of Variation in Molecular Weight on the Antigenicity of Dextran in Man. Archives of Biochemistry and Biophysics. vol. 78, pp. 306-318 (1958).
Kalra, P., et al. Iron isomaltoside 1000: a new high dose option for parenteral iron therapy. Port J Nephrol Hypert 2012. vol. 26, No. 1, pp. 13-24. Mar. 2012.
Kantor, J., et al. Decreased Serum Ferritin is Associated With Alopecia in Women. The Society for Investigative Dermatology, Inc. 2003.
Kardos, N., et al. Sonochemistry of carbohydrate compounds. Carbohydrate Research. vol. 332 (2001) 115-131.
Keating, G. M. Ferric Carboxymaltose: A Review of Its Use in Iron Deficiency. Drugs (2015) 75:101-127.
Khalikova, E., et al. Microbial Dextran-Hydrolyzing Enzymes: Fundamentals and Applications. Microbiology and Molecular Biology Reviews, Jun. 2005, p. 306-325. American Society for Microbiology.
Ahsan, N., et al. Efficacy of Bolus Intravenous Iron Dextran Treatment in Peritoneal Dialysis Patients Receiving Recombinant Human Erythropoietin. Advances in Peritoneal Dialysis. vol. 12, 1996.
Kibbe, A. (Ed.) Maltodextrin. Excerpt from Handbook of Pharmaceutical Excipients, Third Edition. (2000).
Kocakoc, E., et al. Pediatric Idiopathic Pulmonary Hemosiderosis Diagnosed by Sputum Analysis: Plain Radiography and Computed Tomography Findings. Medical Principles and Practice, vol. 12, pp. 129-132 (2003).
Konofal, E., et al. Iron Deficiency in Children with Attention Deficit Hyperactivity Disorder. Arch Pediatr Med. vol. 158, pp. 1113-1115 (2004).
Kreuzer, K., et al. European Journal of Haematology, vol. 98, No. 3, Mar. 2017. (Excerpt, 2 pages).
Kudasheva, D., et al. Structure of carbohydrate-bound polynuclear iron oxyhydroxide nanoparticles in parenteral formulations. Journal of Inorganic Biochemistry, vol. 98, 1757-1769, 2004.
Kulnigg, S. et al. A Novel Intravenous Iron Formulation for Treatment of Anemia in Inflammatory Bowel Disease: The Ferric Carboxymaltose (FERINJECT®) Randomized Controlled Trial.
Frankenfield, et al. Anemia management of adult hemodialysis patients in the U.S.: Results from the 1997 ESRD Core Indicators Project. Kidney international, vol. 57 (2000), pp. 578-589.
Frankenfield, et al. Figures. Anemia management of adult hemodialysis patients in the U.S.: Results from the 1997 ESRD Core Indicators Project. Kidney International. vol. 57, Issue 2, pp. 578-589 (Oct. 2000).
Funk, et al. The new generation of intravenous iron: chemistry, pharmacology, and toxicology of ferric carboxymaltose. Ferric carboxylmaltose. Arzneimittelforschung 2010;60(6 a):345-353.
21 Years Later . . . One Group, two strategies—Separation scheduled for Q4 2016. The Galencia Group. Apr. 2016.
Application to USPTO for patent term extension of U.S. Pat. No. 7,612,109 was filed on Sep. 19, 2013, under 35 U.S.C. § 156. Food and Drug Administration, Office of Regulatory Policy. Oct. 22, 2014.
Geisser, et al. The Pharmacokinetics and Pharmacodynamics of Iron Preparations. Pharmaceutics 2011, 3, 12-33; doi:10.3390/pharmaceutics3010012. Jan. 4, 2011.
USPTO U.S. Appl. No. 13/556,733, filed Jun. 28, 2016.
USPTO communication to Goodwin Proctor dated Mar. 26, 2014, extending the term of U.S. Pat. No. 6,599,498 (Groman, et al., issued Jul. 29, 2003).
Health Bill No. 1325 of the Texas State Legislature.
Haines, et al. Delayed adverse reactions to total-dose intravenous iron polymaltose. Internal Medicine Journal 39 (2009) 252-255.
Hamstra, et al. Intravenous iron dextran in clinical medicine. (Abstract) JAMA. May 2, 1980;243(17):1726-31.
Kibbe, A. (Ed.) Maltodextrin. Handbook of Pharmaceutical Excipients, Third Ed. (2000) American Pharmaceutical Association and Pharmaceutical Press.
Hartsfield, J. Iron Status in the Female Blood Donor. Nutrition Bytes. vol. 4, No. 1, 1998. University of California.
Excerpt from Hawley's Condensed Chemical Dictionary Eleventh Edition. 1987 by Van Nostrand Reinhold Company Inc.
Hedin, et al. Pathomechanisms of Dextran-Induced Anaphylactoid/Anaphylactic Reactions in Man. Int. Archs Allergy Appl. Immun. 68: 122-126(1982).
U.S. Pat. No. 7,754,702 (Helenek) issued Jul. 13, 2010 from U.S. Appl. No. 11/620,986, filed Jan. 8, 2007.
Office Actions and Amendments from U.S. Appl. No. 11/620,986 (Helenek), filed Jan. 8, 2007.
Declaration of Richard P. Lawrence filed in U.S. Appl. No. 12/787,283 (Helenek), filed May 25, 2010 for Methods and Compositions for Adminstration of Iron.
Office Actions and Amendments from U.S. Appl. No. 12/787,283 (Helenek), filed May 25, 2010 for Methods and Compositions for Adminstration of Iron.
U.S. Pat. No. 8,431,549 issued Apr. 30, 2013 from U.S. Appl. No. 12/787,283 (Helenek), filed May 25, 2010 for Methods and Compositions for Administration of Iron.
Petitioner's Power of Attorney filed in USPTO Before the Patent Trial and Appeal Board in RE: U.S. Pat. No. 8,895,612(Helenek) issued Nov. 25, 2014 for Methods and Compositions for Administration of Iron.
Office Action and Amendment of U.S. Appl. No. 14/100,717 (Helenek), filed Dec. 9, 2009 for Methods and Compositions for Administration of Iron.
Petition for Inter Partes Review—Before the USPTO Patent Trial and Appeal Board—Filed in U.S. Pat. No. 8,895,612 (Helenek) issued Nov. 25, 2014 for Methods and Compositions for Administration of Iron.
U.S. Appl. No. 14/100,717 (Helenek), filed Dec. 9, 2009 for Methods and Compositions for Administration of Iron.
U.S. Appl. No. 13/847,254 (Helenek), filed Mar. 19, 2013.
USPTO Patent assignment 048067 /0271 Change of Name Recorded Jan. 11, 2019. Assignors Luitpold Pharmaceuticals, Inc. Reel/frame 048067 /0271 Execution Date Jan. 2, 2019. Assignee American Regent, Inc.
U.S. Pat. No. 8,431,549(Helenek) issued Apr. 30, 2013 for Methods and Compositions for Administration of Iron.
U.S. Pat. No. 10,478,450 (Helenek) issued Nov. 19, 2019 for Methods and Compositions for Administration of Iron.
U.S. Appl. No. 13/847,254 (Helenek), filed Mar. 19, 2013 for Methods and Compositions for Administration of Iron.

(56) References Cited

OTHER PUBLICATIONS

Amendment and Response to Office Action filed Jun. 9, 2014 in U.S. Appl. No. 14/100,717 (Helenek), filed Dec. 9, 2009 for Methods and Compositions for Administration of Iron.

Help on the Quick Search Page. Internet web page from USPTO Patent Full-Text and Image Database retrieved from the Internet on Oct. 6, 2015 from URL: http://patft .uspto.gov/netahtml/PTO/help/helpbool.htm#right.

Medical Definition of Hematinic from Internet web page Webster's Medical Dictionary retrieved on May 28, 2015 from URL: http://www.merriam-webster/Medical/hemalinic.

Highlights of Prescribing Information—Ferrlecit (sodium ferric gluconate complex in sucrose injection), for intravenous (IV) use. 2011 sanofi-aventis U.S. LLC.

Highlights of Prescribing Information—Venofer (iron sucrose), injection for intravenous use. 2018. American Regent, Inc. Shirley, NY.

Hood, S., et al. The Safety of Intravenous Iron Dextran (Dexferrum®) During Hemodialysis in Patients with End Stage Renal Disease. Nephrology Nursing Journal II Feb. 2000■ vol. 27, No. 1.

Beshara, S., et al. Pharmacokinetics and red cell utilization of 52Fe/59Fe-labelled iron polymaltose in anaemic patients using positron emission tomography. British ]011rnal of Haematology, 2003, 120, 853-859.

Icodextrin Hypersensitivity in a CAPD Patient. Peritoneal Dialysis International. Downloaded from website at URL: Http://www.pdiconnect.com on Mar. 25, 2016.

Drug package insert. Imferon iron dextran injection USP. Fisons Pharmaceuticals. Rochester, NY. May 1999.

Drug package insert. INFeD iron dextran injection USP. Schein Pharmaceutical Inc. Florham Park, NJ. Sep. 1996.

Highlights of Prescribing Information—INJECTAFER® (ferric carboxymaltose injection) for intravenous use. American Regent Inc. Shirley, NY.

Orange Book: Approved Drug Products with Therapeutic Equivalence Evaluations—Search results from the OB_Rx • table for query on "203565" —INJECTAFER® (ferric carboxymaltose injection) for intravenous use. Retrieved from the Internet on Mar. 9, 2015 from URL: http://www.accessdata.fda.gov/scri pts/cder/ob/docs/obdetail.cfm ?Appl_N o= 203565& T ABLE1 =OB_Rx.

(Drug Package Insert) Highlights of Prescribing Information—Full Prescribing Information—INJECTAFER® (ferric carboxymaltose injection) for intravenous use. American Regent, Inc. Shirley, NY. 2013.

(Drug Package Insert) Highlights of Prescribing Information—INJECTAFER® (ferric carboxymaltose injection) for intravenous use. American Regent, Inc. Shirley, NY. Apr. 2018.

Paper No. 4. Notice of Filing Date Accorded to Petition and Time for Filing Patent Owner Preliminary Response. United States Patent and Trademark Office—Before the Patent Trial and Appeal Board. *Pharmacosmos*, Petitioners, v. *Luitpold Pharmaceuticals, Inc.*, Patent Owner. Case IPR2015-01490; U.S. Pat. No. 7,754,702. Mailed: Jul. 10, 2015.

Paper No. 11. Decision Institution of Inter Partes Review 37 C.F.R. § 42.108. United States Patent and Trademark Office—Before the Patent Trial and Appeal Board. *Pharmacosmos*, Petitioners, v. *Luitpold Pharmaceuticals, Inc.*, Patent Owner. Case IPR2015-01490; U.S. Pat. No. 7,754,702. Entered Jan. 8, 2016.

Paper No. 13. Erratum Institution of Inter Partes Review C.F.R. § 42.108. United States Patent and Trademark Office—Before the Patent Trial and Appeal Board. *Pharmacosmos*, Petitioners, v. *Luitpold Pharmaceuticals, Inc.*, Patent Owner. Case IPR2015-01490; U.S. Pat. No. 7,754,702. Entered Jan. 21, 2016.

Paper No. 54. Final Written Decision 35 USC§ 318(a) and 37 C.FR. § 42. 73. United States Patent and Trademark Office—Before the Patent Trial and Appeal Board. *Pharmacosmos*, Petitioners, v. *Luitpold Pharmaceuticals, Inc.*, Patent Owner. Case IPR2015-01490; U.S. Pat. No. 7,754,702. Entered Jan. 4, 2017.

Paper No. 57. Order Conduct of the Proceeding 37 C.F.R. § 42.5. United States Patent and Trademark Office—Before the Patent Trial and Appeal Board. *Pharmacosmos*, Petitioners, v. *Luitpold Pharmaceuticals, Inc.*, Patent Owner. Case IPR2015-01490; U.S. Pat. No. 7,754,702. Entered Aug. 23, 2019.

Cisar, et al. Binding Properties of Immunoglobulin Combining Sites Specific for Terminal or Nonterminal Antigenic Determinants in Dextran. The Journal of Experimental Medicine • vol. 142, 1975.

Before the Patent Trial and Appeal Board—Corrected Motion to Amend—*Pharmacosmos A/S* v *Luitpold Pharmaceuticals, Inc.*Case No. IPR2015-01490; U.S. Pat. No. 7,754,702 B2. Apr. 25, 2016.

Before the Patent Trial and Appeal Board—Corrected Motion to Amend—*Pharmacosmos A/S* v *Luitpold Pharmaceuticals, Inc.*Case No: IPR2015-01493; U.S. Pat. No. 8,431,549 B2. Apr. 25, 2016.

Before the Patent Trial and Appeal Board—Corrected Patent Owner Exhibit List as of Apr. 25, 2016—*Pharmacosmos A/S* v *Luitpold Pharmaceuticals, Inc.*Case No. IPR2015-01490; U.S. Pat. No. 7,754,702 B2.

Before the Patent Trial and Appeal Board—Corrected Patent Owner Exhibit List as of Apr. 25, 2016—*Pharmacosmos A/S* v *Luitpold Pharmaceuticals, Inc.*Case No. IPR2015-01493; U.S. Pat. No. 8,431,549 B2.

Package Insert. CosmoFer 50 mg/ml Iron(III)-hydroxide dextran complex solution for injection and infusion single dose container. Vitaline Pharmaceuticals UK Limited. Mar. 10, 2005.

Coulson, et al. Some Observations on the Immunochemistry of Dextrans. The Journal of Immunology. vol. 86. 1961.

Crighton, et al. Iron therapy with special emphasis on intravenous administration. 3rd edition—Bremen: UNI-MED, 2006.

Crighton, et al. Iron therapy with special emphasis on intravenous administration. 4th edition—Bremen: UNI-MED, 2008.

Crighton, et al. 7. Iron Therapy. Iron therapy with special emphasis on intravenous administration. UNI-MED 2017.

Dandah, et al. Intravenous Iron Dextran Treatment in Predialysis Patients With Chronic Renal Failure. American Journal of Kidney Diseases, vol. 36, No. 4 Oct. 2000: pp. 775-782.

Danielson, et al. Iron Therapy with Special Emphasis on Intravenous Administration. First Edition. 1996. Vifor (International) Inc. MEDSAFE New Zealand Medicines and Medical Devices Safety Authority. Information for Health Professionals. Data Sheet—Ferrosig Iron polymaltose 50 mg/ml. Retrieved from the Internet Feb. 16, 2010 at URL: http://www.medsafe.govt.nz/Profs/Datasheet/f/F errosiginj .htm.

DeBelder, A.N. Dextran. Edition AA. Handbook 18/1166-12. Amersham Biosciences AB, 2003.

DeBelder, A.N. Dextran. Ullman's Encyclopedia of Industrial Chemistry, 6th Ed. vol. 10. Cyrogenic Technology to Dithiocarbarnic Acid and Derivatives. 2003 Wiley-VCHVcrlag GmbH & Co. KGaA, Weinheim.

DeNooy, et al. On the Use of Stable Organic Nitroxyl Radicals for the Oxidation of Primary and Secondary Alcohols. Sythesis. Oct. 1996.

Deary, et al. Evidence for cyclodextrin dioxiranes. Carbohydrate Research 309 (1998) 17-29.

Hill, Hugh, et al. Decision Memo for Ferrlecit®: Intravenous Iron Therapy (CAG-00046N). Apr. 20, 2000.

DeMaeyer, et al. Preventing and Controlling Iron Deficiency Anaemia Through Primary Health Care a Guide for Health Administrators and Programme Managers. World Health Organization, 1989. Praxis—Schweizerische Rund Schau Fur I\Iedizin. Revue Suisse De Medecine. No. 22. Jun. 1, 1950.

Dextran I for injection. European Pharmacopoeia 5.0.

Dextran I. USP28-NF23, Official Monographs/Dextran, pp. 601-602 © The United States Pharmacopeial Convention, Inc.

Dextran T1 Technical Quality | Pharmacosmos Dextran Safety Data Sheet May 27, 2015.

Dextran I. USP 28—The United States Pharmacopeia—NF 23—The National Formulary. Official Compendium of Standards. 2005.

O'Neill, et al. Dextran (definition entry) The Merck Index: An Encyclopedia ofChemicals, Drugs, and Biologicals, Fourteenth Edition, 2006.

Falbe, et al. Dextrin (definition entry) Rompp Lexikon Chemie. vol. 10. 1997.

Excerpt from Webster's Ninth New Collegiate Dictionary, 1986.

(56) References Cited

OTHER PUBLICATIONS

Excerpt from Merriam-Webster's Collegiate Dictionary, Eleventh Edition, 2005.
Dixon. Polysaccharide Nomenclature. Pura & Appl.Chem., vol. 54, No. 8, pp. 1523-1526, 1982.
Egeli, et al. An evaluation of iron-dextran supplementation in piglets administered by injection on the first, third or fourth day after birth. Research in Veterinary Science 1999, 66, 179-184 Article No. rvsc.1998.0223, available online at http://idealibrary.com.
Elephant. San Diego Zoo Animals. Retrieved from the Internet Jun. 13, 2016 at URL: http://animals.sandiegozoo.org/animals/elephant.
Eriksson, et al. Pharmacological Studies on an Iron-poly(sorbitol-gluconic acid) complex for Parenteral Treatment of Iron Deficiency Anaemia. Scand J Haematol (1977) Suppl. 32, 38-49.
Iron overload: molecular clues to its cause. Frontlines. TIBS May 24, 1999.
Ersoy, et al. Blood Pool MRAngiography of Aortic Stent-Graft Endoleak. American Journal of Roentgenology. vol. 182, No. 5, May 2004.
Esposito, et al. Labile iron in parenteral iron formulations and its potential for generating plasma non-transferrin bound iron in dialysis patients. Iron: Harmful biological affects of an essential nutrient. European Journal of Clinical Investigation. vol. 32 Supp 1. 2002.
Excerpt from European Journal of Haematology vol. 98, No. 3, Mar. 2017.
U.S. Appl. No. 13/857,254 (Helenek), filed Mar. 19, 2013.
Executive Bio. Mary Jane Helenek—President and CEO, Luitpold Pharmaceuticals Inc. Retrieved from the Internet on Oct. 7, 2015 at URL: http://www.luitpold.com/ExecutiveBios.aspx.
Google Scholar Search of Oct. 7, 2015—Experience with the use of an iron polymaltose ( dextrin) complex given by single total dose infusion to stable chronic haemodialysis patients.
Federal Register vol. 34 • No. 31. Friday, Feb. 14, 1969 • Washington, D. C. pp. 2173-2235.
Package Insert for FERAHEME® (ferumoxytol) Injection for Intravenous (IV) use AMAG Pharmaceuticals, Inc. Waltham, MA. 2015.
FDA strengthens warnings and changes prescribing instructions to decrease the risk of serious allergic reactions with anemia drug Feraheme (ferumoxytol). Safety Announcement. U.S. Food and Drug Administration. Mar. 30, 2015.
Package Insert for Ferrinject (ferric carboxylmaltose) Ferinject• 50 mg iron/111l solution for injection/infusion. Vifor France SA. Jun. 2012.
Iron Corner—IV Iron Products. Society for the Advancement of Blood Management, Inc. Englewood, NJ. Nov. 2013.
Ferrlecit® Description. NDA 20-955/S-003. pp. 3-11. Watson Pharmaceutical, Inc., and R&D Laboratories, Inc. 2001.
Fishbane, et al. The Comparative Safety of Intravenous Iron Dextran, Iron Saccharate, and Sodium Ferric Gluconate. Seminars in Dialysis—vol. 13, No. 6 Nov./Dec. 2000 pp. 387-384.
Fishbane, et al. Sodium Ferric Gluconate Complex in the Treatment of Iron Deficiency for Patients on Dialysis. American Journal of Kidney Diseases. vol. 37, No. 5, May 2001.
Fleming, et al. Dextran Antibodies, Complement Conversion and Circulating Immune Complexes After Intravenous Iron Dextran Therapy in Dialysed Patients. Nephrol Dial Transplant (1992) 7: 35-39.
Folb, Peter. The Safety of Iron Dextran and a Comparison With Iron Sucrose for Intravenous Use: A Short Report to the World Health Organization Advisory Committee on the Safety of Medicines. Oct. 18, 2004.
Ferrum Hausmann—Solution for Injection Bundesgesundheitsamt {BGA) [Federal Health Agency] Notification of a marketed finished dosage product according to Article 3 Section 7 (2) sentence 1 of the Act on the Reform of the Pharmaceutical Regulation, dated Aug. 24, 1976 (BGBL. (Federal law Gazette) I p. 2445).
Nasimul Ahsan, et al. Efficacy of Bolus Intravenous Iron Dextran Treatment in Peritoneal Dialysis Patients Receiving Recombinant Human Erythropoietin. Advances in Peritoneal Dialysis, vol. 12, 1996.

Report of the ACS Carbohydrate Division Nomenclature Committee. Annual Meeting of the ACS Committee on Nomenclature, Terminology and Symbols. New Orleans Apr. 7, 2008.
Shearer, William T., et al. Chapter 1: The Immune System. Adkinson, N. Franklin, et al. Middleton's Allergy Principles and Practice, 6th Ed. vol. 1, 2003.
Frank, Michael M., et al. Chapter 58: Immune Complexes and Allergic Disease. Adkinson, N. Franklin, et al. Middleton's Allergy Principles and Practice, 6th Ed. vol. 2, 2003.
Adkinson, Jr. M.D., N. Franklin. Curriculum Vitae. Jul. 9, 2019. The John Hopkins University School of Medicine.
Declaration of N. Franklin Adkinson, M.D. Before the Patent Trial and Appeal Board Case No. PGR2020-00009 U.S. Pat. No. 10,478,450. *Pharmacosmos A/S* Petitioner v. *American Regent Inc.* Patent Owner, Jan. 6, 2020.
Agarwal, R., et al. Oxidative stress and renal injury with intravenous iron in patients with chronic kidney disease. Kidney International, vol. 65 (2004), pp. 2279-2289.
Polimaltosa Ferrica—Iron Polymaltose. Medicamentos Veterinaria—Veterinary Drugs. Medicamentos de Actualidad—Drugs of Today. vol. XII No. 10 1976.
Ahsan, N. et al. Efficacy of Bolus Intravenous Iron Dextran Treatment in Peritoneal Dialysis Patients Receiving Recombinant Human Erythropoietin. Selected Papers of the 16th Annual Conference on Peritoneal Diaysis, Seattle, Washington, Feb. 1996. Advances in Peritoneal Dialysis, vol. 12, 1996.
Al, Ragip A., et al. Intravenous Versus Oral Iron for Treatment of Anemia in Pregnancy—A Randomized Trial. Obstetrics and Gynecology vol. 1 06, No. 6, Dec. 2005 American College of Obstetrics and Gynecology.
Alternative Dispute Resolution Statement Before the Patent Trial and Appeal Board Cases IPR2015-01490; U.S. Pat. No. 7,754,702 B2 and IPR2015-01493; U.S. Pat. No. 8,431,549 B2 *Pharmacosmos A/S*, Petitioner v. *Luitpold Pharmaceuticals, Inc.*, Patent Owner, Feb. 23, 2016.
New Drug Application (NDA) 22-054 for Injectafer (Ferric Carboxymaltose) for the treatment of iron deficiency anemia in patients with heavy uterine bleeding or postpartum patients. FDA Advisory Committee Briefing Document. Drug Safety and Risk Management Committee Feb. 1, 2008. Prepared by the Division of Medical Imaging and Hematology Products/Office of Oncology Drug Products/Office of New Drugs.
IV. NKF-K/DOQI Clinical Practice Guidelines for Anemia of Chronic Kidney Disease: Update 2000 National Kidney Foundation. K/DOQI Clinical Practice Guidelines for Anemia of Chronic Kidney Disease, 2000. Am J Kidney Dis 37:SI82-S238, 2001 (suppl 1).
KDOQI Clinical Practice Guidelines and Clinical Practice Recommendations for Anemia in Chronic Kidney Disease. American Journal of Kidney Diseases vol. 47, No. 5, Suppl 3, May 2006. National Kidney Foundation.
Anaemex 100 mL HDPE vials. Certificate of Analysis. Quality Department. P. Solla Gonzalez, Quality Department Manager. CZ Veterinaria S.L. Porrino (Pontevedra) Espana.
Andersson, Nils S. E. Clinical Investigations on a New Intramuscular Haematinic. British Medical Journal. Jul. 29, 1961.
Supplementary European Search Report issued by the European Patent Office in Application No. EP 07 71 6309 and dated Oct. 8, 2009.
Remarks section of an amendment response to Office Action filed in U.S. Appl. No. 10/531,895 on Feb. 4, 2008 in reply to USPTO Office Action dated Oct. 5, 2007.
USPTO Non-Final Office Action dated Oct. 3, 2011 issued in U.S. Appl. No. 12/581,212 (Geisser), filed Oct. 19, 2009.
USPTO Final Office Action dated Nov. 5, 2013 issued in U.S. Appl. No. 13/556,733 (Geisser), filed Jul. 24, 2012.
Arond, Lester H., et al. Molecular Weight, Molecular Weight Distribution and Molecular Size of Native Dextran. Native Dextran, vol. 58. Nov. 1954.
Auerbach, M., et al. How we diagnose and treat iron deficiency anemia. American Journal of Hematology, vol. 91, No. 1, Jan. 2016.

(56) References Cited

OTHER PUBLICATIONS

Auerbach, M., et al. The available intravenous iron formulations: History, efficacy, and toxicology. Scholarly Review. Hemodialysis International 2017; 21:S83-S92.
Avaltroni, F., et al. Maltodextrin molecular weight distribution influence on the glass transition temperature and viscosity in aqueous solutions. Carbohydrate Polymers 58 (2004) 323-334. Sep. 11, 2004.
Avni, T., et al. The Safety of Intravenous Iron Preparations: Systematic Review and Meta-analysis. Mayo Clin Proc. Jan. 2015;90(1):12-23 http://dx.doi.Org/10.1016/j.mayocp.2014.10.007 www.mayoclinicproceedings.org © 2015 Mayo Foundation for Medical Education and Research.
Bailie, George et al. Hypersensitivity reactions and deaths associated with intravenous iron preparations. Nephrology Dialysis Transplantation (2005) 20: 1443-1449 doi: 10.1093/ndt/gfh820 Advance Access publication Apr. 26, 2005.
BeMiller, James N. Polysaccharides. Encyclopedia of Life Sciences© 2001, John Wiley & Sons, Ltd. www.els.net.
Beshara, S., et al. Pharmacokinetics and red cell utilization of iron(III) hydroxide-sucrose complex in anaemic patients: a study using positron emission tomography. British Journal of Haematology, 1999, 104, 296-302. Nov. 9, 1998.
Haines, M. L., et al. Brief Communication—Delayed adverse reactions to total-dose intravenous iron polymaltose. Internal Medicine Journal 39 (2009) 252-255. Jul. 12, 2008.
Bhaskaran, Madhu et al. Hepatitis B Antibody Response in Hemodlalysls Patients: Impact of Iron Deficiency. Iron and Erythrocytes in Dialysis Patients. J Am Soc Nephrol 14: 2003.
Blaustein, et al. Recent experience with high-dose intravenous iron administration. Kidney International (2006) 70, S26-S29. doi:10.1038/sj.ki.5001973.
Saloojee, H., et al. Iron deficiency and impaired child development— The relation may be causal, but it may not be a priority for intervention. BMJ vol. 323 1377-8. Dec. 15, 2001 bmj.com.
DeBelder, Anthony. Dextran. Ullman's Encyclopedia of Industrial Chemistry. Sixth Ed. vol. 10. ISBN 3-527-30385-5 © 2003 Wiley-VCH Verlag GmbH & Co. KGaA, Weinheim.
Broadhead, Joanne. Parenteral Dosage Forms. Chapter in Gibson, Mark. Pharmaceutical Preformulation and Formulation. A Practical Guide from Candidate Drug Selection to Commercial Dosage Form. 2001. ISBN: 1-57491-120-1 HS* Health Group, Englewood, CO.
Brugnara, Carlo. Iron Deficiency and Erythropoiesis: New Diagnostic Approaches. Clinical Chemistry 49:10 1573-1578 (2003).
Brunner, et al. SANZ-StreiflichtNr. 21 Parenterale Eisenapplikation: Probleme mit Eisendextranpraparaten. Mosaik. vol. 76; Issue 9; 1995.
Brunner, et al. SANZ Highlight No. 21 Parenteral iron application: problems with iron dextran preparations. Mosaic. vol. 76; Issue 9; 1995 (Translation).
Burns, et al. Parenteral Iron Dextran Therapy: A Review. Nutrition— The International Journal of Applied and Basic Nutritional Sciences. vol. 11; No. 2; Mar./Apr. 1995.
Burns, et al. Toxicity of parenteral iron dextran therapy. Kidney international, vol. 55, Suppl. 69 (1999), S-119-S-124.
C57BL/6 Mice Nomenclature: C57BL/6NCrl. Charles River research models. © 2011,Charles River Laboratories International, Inc.
Cada, et al. Formulary Drug Reviews—Ferric Carboxymaltose. Hosp Pharm 2014;49(1):52-69 2014 © Thomas Land Publishers, Inc.
Caligur, V. Dextran and Related Polysaccharides BioFiles 2008, 3.10, 17. Sigma Aldrich.
Carley, A. Anemia: When is it Not Iron Deficiency? Pediatr Nurs 29(3):205-211, 2003. © 2003 Jannetti Publications, Inc. URL: http://www.medscape.com/viewarticle/457482.
Carroll, M. The complement system in regulation of adaptive immunity. Nature Immunology vol. 5 No. 10 Oct. 2004.
Chandler, G., et al. Intravenous Iron Sucrose: Establishing a Safe Dose. American Journal of Kidney Diseases, vol. 38, No. 5 Nov. 2001: pp. 988-991.

U.S. Appl. No. 11/620,986, filed Jan. 8, 2007 now U.S. Pat. No. 754702 issued Jul. 13, 2010.
Charytan, C., et al. Safety of Iron Sucrose in Hemodialysis Patients Intolerant to Other Parenteral Iron Products. Nephron Clin Pract 2004;96:c63-c66. Nov. 28, 2003.
Chemical Reviews. Center for Drug Evaluation and Research. Application No. 21-135 for Venofer Iron Sucrose Injection. Division of Gastrointestinal and Coagulation Drug Products. Review of Chemistry, Manufacturing and Controls. Oct. 27, 2000.
Chertow, et al. On the relative safety of parenteral iron formulations. Nephrol Dial Transplant (2004) 19:6: 1571-1575.
Redacted P-IV Notice of Certification Letter on behalf of Sandoz Inc. dated Jul. 10, 2019.
Barbara Jankiewicz et al., The Influence of Molar Mass of Oligosaccharides on Their Ability to Disperse Iron Hydroxide (III), Acta Poloniae Pharmaceutica—Drug Research, 1994; pp. 187-189, vol. 51, No. 2.
Iain C. MacDougall, Strategies for Iron Supplementation: Oral Versus Intravenous, Kidney International, 1999, pp. S-61-S-66, vol. 55, Suppl. 69.
Kanti M. Patel & J.A. Tulloch, Total Dose Imferon (Iron-dextran Complex) Infusion Therapy in Severe Hookworm Anemia, British Medical Journal, 1967, pp. 605-607, vol. 2.
Roger D. Hamstra et al., Intravenous Iron Dextran in Clinical Medicine, JAMA, 1980, pp. 1726-1731, vol. 243, No. 17.
John J. Perkins, Principles and Methods of Sterilization in Health Sciences, 2d Edition, 8th Printing, (1983) pp. 117-118.
Physician's Desk Reference, 55th Edition (2001) pp. 2879-2881 (INFeD).
Physician's Desk Reference, 56th Edition (2002) pp. 580-581 (Venofer), 3386-3388 (Ferrlecit).
INFeD FDA Label, Watson Pharmaceuticals, Inc. (Rev. Jul. 2009).
Dexferrum FDA Label, American Regent, Inc. (Rev. Aug. 2008).
Redacted P-IV Notice of Certification Letter on behalf of Mylan Laboratories Ltd. dated May 7, 2019.
Fielding, "Intravenous Iron-Dextrin in Iron-Deficiency Anaemia", British Medical Journal, Jul. 29, 1961, pp. 270-283.
Rutenberg et al., "Starch: Chemistry and Technology—Chapter X, Starch Derivatives: Production and Uses", Academic Press, 1984, pp. 311-388.
Funk et al., "Physical and Chemical Characterization of Therapeutic Iron Containing Materials: A Study of Several Superparamagnetic Drug Formulations with the β-FeOOH or Ferrihydrite Structure", Hyperfine Interactions, Mar. 2001 pp. 73-95.
Baker et al., "Hydrolysis of Potato and Malt Starches by Malt Amylase Part II: Maltodextrin", Journal of the Institute of Brewing, vol. 44, Issue 6, pp. 514-519, Nov.-Dec. 1938.
Goetsch et al., "Observations on the effect of massive doses of iron given intravenously to patients with hypochromic anemia", Blood 1: 129-142,1946.
Nagy et al., "Equillibrium and structural studies on metal complexes of carbohydrates and their derivatives", Journal of Inorganic Biochemistry 89 (2002) 1-12.
Gyurscik et al., "Carbohydrates as ligands: coordination equilibria and structure of the metal complexes", Coordination Chemistry Reviews 203 (2000) 81-149; p. 107.
21 Code of Federal Regulations Sec. 184.1444, Apr. 1, 2015.
Floor et al., "Oxidation of Maltodextrins and Starch by the System Tungstate—Hydrogen Peroxide", Starch/Starke 41 (1989) Nr. 8, S 303-309.
Pecsok et al., "The Gluconate Complexes. II. The Ferric-Gloconate System", J. Am. Chem Soc., 1955 77 (6), pp. 1489-1494.
Floor et al., "Preparation and calcium complexation of oxidized polysaccharides", Starch-Starke, 41 (9) : 348-354, 1989.
Edelman et al., Journal of Biological Chemistry 1954-55, 213:843-854.
Drug Approval Package: Venofer (Iron sucrose) NDA #21135, retrived Nov. 9, 2015 from http://www.accessdata.fda.gov/drugsatfda_docs/nda/2000/21135_Venofer.cfm.
Sucrose is digested to glucose and fructose (Wikipedia), Jul. 15, 2015.

(56) References Cited

OTHER PUBLICATIONS

Glucuronic acid., A Dictionary of Biology 2004. Retrieved Jul. 10, 2015 from Encyclopedia.com : http://www.enceclopedia.com/doc/106-glucuronicacid.html.
Fel'dman et al., "Methods of Synthesis and Technology of Drug Production. Methods of obtaining D-glucuronic acid from D-glucose. II. Synthesis of glucuronides and their conversion into D-glucuronic acid", Pharmaceutical Chemistry Journal, Feb. 1983, vol. 17, Issue 2, pp. 134-140.
Maltodextrin — Hyet Sweet, http://www.heyetsweet.com/product/bulkingagents/maltodextrin/ accessed on Jul. 16, 2015.
P. Lundsgaard-Hansen, "Treatment of Shock with Dextrans and Gelatins", Vox Sang. 17 161-193 (1969).
Sellevold et al., "Procaine is Effective for Minimixing Postichemic Ventricular fibrillation in Cardiac Surgery", Anaesthesia, 1991, vol. 46, pp. 1033-1035.
Faich et al., "Sodium Ferric Gluconate Complex in Sucrose: Safer Intravenous Iron Therapy Than Iron Dextrans", American Journal of Kidney Diseases, vol. 33, No. 3 Mar. 1999: pp. 464-470.
Bailie et al., "Parenteral Iron Use in the Management of Anemia in End-Stage Renal Disease Patients", American Journal of Kidney Diseases, vol. 35, No. 1 Jan. 2000: pp. 1-12.
Steven Fishbane, :Safety in Iron Management American Journal of Kidney Diseases, vol. 41, No. 6, Suppl 5 Jun. 2003: pp. S18-S26.
Form 3 detailing the status of corresponding applications filed by the Plaintiff dated May 24, 2005.
Espacenet Abstract of EP 1554315(a1), A comparison of the said Form 3 with the list of countries where corresponding patent applications has been filed (as obtained from the EPO website).
Excerpts from the CAS registry No. 1965-71 (9007-72-1)—Iron Polymaltose.
Jeanes et al., "Chemical Reactions of the chlorites with carbohydrates" National Bureau of Standards, vol. 27, Aug. 1941.
Ricketts et al. "The Iron Dextran Complex", Nature, No. 5007, pp. 237, 239, 1965.
Kearsley et al., "Handbook of Starch Hydrolysis Products and Their Derivatives", Maltodextrins, pp. 65-67 1995 Springer Science+ Business Media Dordrecht.
Marchasin et al., "The Treatment of Iron-Deficiency Anemia with Intravenous Iron Dextran", 1964, BI. 23(3), 354-358.
Preusser et al., "Effects of intravenous ABT-870 (iron (III)-hydroxide oligosaccharide) on mean arterial pressure and heart rate in the anaesthetized beagle: comparison with other iron-containing haematinic agents", Clinical and Experimental Pharmacology and Physiology (2005), 32, 1020-1026.
Crichton et al., "Iron Therapy with Special Emphasis on Intravenous Administration", UNI-MED, 2005, 2nd edition, cover page, foreword, acknowledgments, preface and contents; and chapters 7, 9, 10 and 11.
Van Wyck, "Labile Iron: Manifestations and Clinical Implications", (2004) J. Am. Soc. Nephrology 15, 5107-S111.
Dr. Barbara von Eisenhart-Rothe, Reproduction of a speech given at a press conference on Apr. 12, 2005, Subject: "Clinical Development Programme of VIT-45", including Screenshot showing results of google search for "eisenhart rothe vit-45", Screenshot showing document properties of D4, UBS report on Galenica's financial results.
Manley et al., "Determination of VIT 45 (IND#63,243—American Regent) removal by closed loop in vitro hemodialysis system", Int J Artif Organs. Nov. 2006; 29(11):1062-6.
Excerpt from Der Bund, edition of Apr. 13, 2005.
Consumer Medicine Information for Promit® "Dextran 1".
Research Subject Information and Consent Form "Evaluation of the safety, tolerability and pharmacokinetic profiles of single rising doses and increasing administration rates of ABT-870 in ESRO subjects on chronic hemodialysis with iron deficiency anemia", Apr. 2004.
Spinowitz et al., "The safety and efficacy of ferumoxytol therapy in anemic chronic kidney disease patients", Kidney International, vol. 68 (2005), 1801-1807.

Landry et al., "Pharmacokinetic study of ferumoxytol: A new iron replacement therapy in normal subjects and hemodialysis patients", American Journal of Nephrology, vol. 25, No. 4, 2005, pp. 400-410, XP009123870.
Hunnius Pharmazeutisches Wörterbuch, 8th edition, 1998, p. 710, catchword "Injections".
Van Zyl-Smit et al., Experience with the Use of an Iron polymaltose (Dextrin) Complex Given by Single Total Dose Infusion to Stable Chronic Haemodialysis Patients; 92 Nephron (2002).
Patent Term Extension Application of U.S. Pat. No. 7,612,109.
Aronoff, "Safety of Intravenous Iron in Clinical Practice: Implications for Anemia Management Protocols", Journal of the American Society of Nephrology, vol. 15, S99-S106 (2004).
Gupte et al., "Iron Deficiency Anemia: Management and Prevention in Children", JK Science, vol. 3(4), 160•165 (2001).
Venofer® approved by FDA ahead of company expectations for use in USA for treatment of iron deficiency anemia in pre-dialysis patients: http://www.evaluategroup.com/Universal/View.aspx?type-Story&id=14089, Jun. 2005.
Danielson, "Structure, chemistry and pharmacokinetics of intravenous iron agents", J Am Soc Nephrol 15, S93-S98 (2004).
Van Wyck et al., „A randomized, controlled tria/ comparing IV iron sucrose to oral iron in anemic patients with nondialysis-dependent CKD, Kidney International, vol. 68, 2846-2856 (2005).
Jahn et al., "A comparative study of the physicochemical properties of iron isomaltoside 1000 (Monofer)(R) a new intravenous iron preparation and its clinical implications", European Journal of Pharmaceutics and Biopharmaceutics, vol. 78, 480-491, (2011).
Assignment of U.S. Appl. No. 11/620,986 dated Mar. 1, 2007/ Mar. 2, 2007.
Seid et al., "Safety Profile of Iron Carboxymaltose, or Now High Dose Intravenus Iron in Patients", Blood,108(11), 3739 (2006).
Paschen, Geburtshilfe Frauenheilkunde, 9, 604-616 (including English translation) (1949).
Nissim, Depsotion of Iron in the Tests After Administration of an Iron-Dextran Complex, Lancet, 268, 701-702 (1955).
McCurdy et al., "Parenteral Iron Therapy", New Engl. J. Med., 257(24), 1147-1153 (1957).
Beshara et al., „Pharmacokinetics and red cell utilization of $^{52}$ Fe/$^{59}$ Fe-labelled iron polymaltose in anaemic patients using positron emission tomography, Brit. J. Haematol. 120, 853-89 (2003).
Product Information of Ferinject for Australia of 2011.
CARHBT(R2) 2025R-4072R (1965-1971)—Chemical Abstracts Service Registry Handbook Number Section.
Fong et al., "A Comparison Between Intravenous Iron Polymaltose Complex (Ferrum Hausmann) and Oral Ferrous Fumarate in the Treatment of Iron Deficiency Anaemia in Pregnancy", *Eur. J. Haematology*, vol. 60, pp. 119-124 (1998).
Rote Liste, product information for Ferrum Hausmann (1996).
Römpp encyclopedia chemistry 9 ("Römpp Chemie Lexikon"); 10th edition, vol. 2, Cm-G, p. 213, 1997, catchword "dextrin".
Römpp encyclopedia chemistry 9 ("Römpp Chemie Lexikon"); 10th edition, vol. 4, M-Pk, p. 518, 1998, catchword "maltodextrin".
German Marketing approval for Ferrum Hausmann (dated 1978).
Bailie, G., "Breaking New Ground in Intravenous Iron Therapy", European Haematology, (2008), pp. 58-60.
Ferinject: Product label in Europe.
Auerbach, M., et al., "Clinical Use of Intravenous Iron: Administration, Efficacy, and Safety, Hematology", (2010), pp. 338-347.
Besemer, A.C., et al., "The Relation between Calcium Sequestering Capacity and Oxidation Degree of Dicarboxy-Starch and Dicarboxy-Inulin", Starke-Starch, vol. 46, No. 11, (1994), pp. 419-422.
De Nooy, A.E.J., et al., "On the Use of Stable Organic Nitroxyl Radicals for the Oxidation of Primary and Secondary Alcohols", Synthesis, vol. 10, (1996), pp. 1153-1174.
Besemer, A. C., et al., "Dicarboxy-starch by Sodium Hypochlorite Bromide Oxidation and Its Calcium Binding Properties", Starch/Starke, vol. 46, No. 3, (1994), pp. 95-101.
Besemer, A.C., et al., "The Hypochlorite Oxidation of Inulin", Recueil Travaux Chim Pays-Bas, vol. 113, No. 9, (1994), pp. 398-402.

(56) References Cited

OTHER PUBLICATIONS

Besemer, A.C., et al., "The Catalytic Effect of Bromide in the Hypochlorite Oxidation of Linear Dextrins and Inulin", Starch/Stärke, vol. 46, No. 3, (1994), pp. 101-106.
Deary, M.E., et al., "Evidence for Cyclodextrin Dioxiranes", Carbohydrate Research, vol. 309, (1998), pp. 17-29.
Kardos, N., et al., "Sonochemistry of Carbohydrate Compounds", Carbohydrate Research, vol. 332, (2001), pp. 115-131.
Anelli, P.L., et al., "Fast and Selective Oxidation of Primary Alcohols to Aldehydes or to Carboxylic Acids and of Secondary Alcohols to Ketones Mediated by Oxammonium Salts Under Two-Phase Conditions", J. of Organic Chemistry, vol. 52, (1987), pp. 2559-2562.
Dextran Structure, http://www.dextran.net/dextran-structure.html.
De Belder, A.N., "Dextran" Dextran Handbook (Amersham) (2003), pp. 1-64.
CAS Registry Handbook(R2) 2025R-4072R (1965-1971)—Chemical Abstracts Service Registry Handbook Number Section.
Singh et al., "A Comparison Between Intravenous Iron Polymaltose Complex (Ferrum Hausmann) and Oral Ferrous Fumarate in the Treatment of Iron Deficiency Anaemia in Pregnancy", Eur. J. Haematology, vol. 60, pp. 119-124 (1998).
"International Nonproprietary Names for Pharmaceutical Substances (INN)", World Health Organization, vol. 22, No. 1 (2008), pp. 41-42, 54.
English translation of CN 1353194 (dated Jun. 12, 2002), ten pages.
Dokic et al., "Molecular characteristics of maltodextrins and rheological behaviour of diluted and concentrated solutions," Colloids Surfaces A: Physicochem. Eng. Aspects 141 (1998) pp. 435-440.
Thaburet et al., "TEMPO-mediated oxidation of maltodextrins and D-glucose: effect of pH on the selectivity and sequestering ability of the resulting polycarboxylates," Carbohydrate Research 330 (2001) pp. 21-29.
International Search Report for corresponding PCT/EP2003/11596 dated Jan. 23, 2004, three pages.
HCAPLUS Abstract 1960:117732 (1960), one page.
HCAPLUS Abstract 2003:135397 (2003), one page.
Bolivian Marketing approval for Ferrum Hausmann (dated 1960).
"International Nonproprietary Names for Pharmaceutical Substnaces (INN)", World Health Organization, vol. 22, No. 1, (2008), pp. 41-42, 54.
Product Information of Ferinject for Australia (2011).
Bailie, G.R., "Efficacy and Safety of Ferric Carboxymaltose in Correcting Iron-Deficiency Anemia: A Review of Randomized Controlled Trials across Different Indications", Arzneimittelforschung, vol. 60, No. 6a), (2010), pp. 386-398.
Burckhardt-Herold, S., et al., "Interactions Between Iron (III)-hydroxide Polymaltose Complex and Commonly Used Drugs", Arzneimittel-Forschung, vol. 57, No. 6a, (2007), pp. 360-369.
Burger, K., et al., "A Novel Plynuclear Iron(III) Mixed Ligand Complex for Use in Parenteral Iron Therapy", Inorganica Chimica Acta, vol. 80, (1983), pp. 231-235.
Coe, E., et al., "Comparison of Polysaccharide Iron Complexes Used as Iron Supplements", Journal of Inorganic Biochemistry, vol. 57, (1995), pp. 287-292.
Devaki, P. B., et al., "Effects of Oral Iron (III) Hydroxide Polymaltose Complex Supplementation of Hemoglobin Increase, Cognitive Function, Affective Behavior and Scholastic Performance of Adolescents with Varying Iron Status", Arzneimittel-Forschung, vol. 59, No. 6, (2009), pp. 303-310.
Driss, F., et al., "Effects of Intravenous Polymaltose Iron on Oxidant Stress and Non-Transferrin-Bound Iron in Hemodialysis Patients", Nephron Clinical Practice, (2005), vol. 99, pp. 63-67.
European Search Report EP 10 194 332.2, dated Jan. 12, 2011. (See Translation).
Ferrlecit NDA 20-955 Ferrlecit, (1999), pp. 1-10.
Ferrlecit 62,5, Beipackzettel Packungsbellage & Fachinformation, (2011), pp. 1-5. (German).

Funk, F., et al., "Interactions Between Iron (III)-hydroxide Polymaltose Complex and Commonly Used Medications", Arzneimittel-Forschung (Drug Research), vol. 57, No. 6a, (2007), pp. 370-375.
Geetha, K., et al., "Transition-Metal Saccharide Chemistry: Synthesis, Spectroscopy, Electrochemistry and Magnetic Susceptibility Studies of Iron (III) Complexes of Mono- and Disaccharides", Carbohydrate Research, vol. 271, (1995), pp. 163-175.
Geisser, P., et al., "Structure/Histotoxicity Relationship of Parenteral Iron Preparations", Arzneim.-Forsch/Drug Res., vol. 42 (ii), No. 12, (1992), pp. 1439-1452.
Geisser, P., "Safety and Efficacy of Iron (III)—hydroxide Polymaltose Complex", Arzneimittel-Forschung (Drug Research), vol. 57, No. 6a, (2007), pp. 439-452.
Kearsley, M. W., et al., "The Determination of the Iron/Chelating Ability of Different Carbohydrates and the Preparation of Ferric/Carbohydrate Complexes", Acia Alimentaria, vol. 8, No. 1, (1979), pp. 69-78.
Lange, W. E., et al., "Avalability of Ionic Iron from Iron Chelates", J. Pharmac. Sci., vol. 51, (1962), pp. 1128-1131.
Lundqvist, H., et al., "Food Interaction of Oral Uptake of Iron", Arzneimittel-Forschung (Drug Research), vol. 57, No. 6a, (2007), pp. 401-416.
MacDougall, I. C., "Evolution of IV Iron Compounds over the Last Centruy", Journal of Renal Care, vol. 35 (s2), (2009), pp. 8-13.
Mannich, C., et al., "Ueber die kolloide Natur des Eisenzuckers", (1922), p. 158-166.
Mannich, V.C., et al., "Wissenschaftliche Mitteilungen", Apotheker-Zeitung, No. 37, (1913), pp. 329-330. (German) See translation.
Mannich, V.C., et al., "Wissenschaftliche Mitteilungen", Apotheker-Zeitung, No. 37, (1913), pp. 329-330. Machine translation.
Picaud, J. C., et al., "Supplementation en fer chez les enfants prématurés traités par érythropoïétine", Arch Pediatr, vol. 6, (1999), pp. 657-664.
Pugh-Clarke, K., et al., "An Evidence-Based Approach to Anaemia Management in Predialysis Chronic Kidney Disease", Journal of Renal Care, vol. 35 (s2), (2009), pp. 29-31.
Qunibi, W. Y., "The Efficacy and Safety of Current Intravenous Iron Preparations for the Management of Iron-Deficiency Anaemia: A Review", Arzneimittelforschung, vol. 60, No. 6a, (2010), pp. 399-412.
Ranfaing, E., "Treatments of the Martial Deficiencies: Preparations Available in France", Néphrologie & Thérapeutique, vol. 5, (2006), pp. 5337-5340. (Abstract).
Rao, C. P., et al., "Fe (III) Complexes of D-glucose and D-Fructose", BioMetals, vol. 7, (1994), pp. 25-29.
Rao, C. P., et al., "Solution Stability of Iron-Saccharide Complexes", Bioorganic & Medicinal Chemistry Letters, vol. 2, No. 9, (1992), pp. 997-1002.
Rao, C. P., et al., "Transition Metal Saccharide Chemistry and Biology: Syntheses, Characterization, Solution Stability and Putative Bio-Relevant Studies of Iron-Saccharide Complexes", Inorganica Chimica Acta, vol. 297, (2000), pp. 373-382.
Tagboto, S., et al., "The Efficacy of a Single Dose of Intravenous Ferric Carboxymaltose (Ferinject®) on Anaemia in a Pre-Dialysis Population of Chronic Kideny Disease Patients", Journal of Renal Care, (2009), vol. 35, No. 1, pp. 18-22.
Tonkovic, M., et al., "Preparation and Properties of Fe(III)-Sugar Complexes", Inorganica Chimica Acta, vol. 80, (1983), pp. 251-254.
Venofer Label, American Regent, Inc. Shirley, NY 11967.
Dokic et al., "Molecular Characteristics of Maltodextrins and Rheological Behaviour of Diluted and Concentrated Solutions", Colloids Surfaces A: Physicochem. Eng. Aspects, vol. 141, (1998), pp. 435-440.
Thaburet et al., "TEMPO-mediated Oxidation of Maltodextrins and D-glucose: Effect of pH on the Selectivity and Sequestering Ability of the Resulting Polycarboxylates", Carbohydrate Research, vol. 330, (2001), pp. 21-29.
International Search Report for corresponding PCT/EP2003/11596 dated Jan. 23, 2004, 3 pages.
Machine English translation of FR 1 451 203 (dated Jan. 7, 1966), six pages.

(56) References Cited

OTHER PUBLICATIONS

English translation of CZ 245379 B1 (dated Jan. 16, 1986), eight pages.
Ferrlecit Highlights of Prescribing Information (Aug. 2011).
Opinion on Motion for Judicial Correction. United States District Court. District of New Jersey. *Vifor (International) AG and American Regent, Inc.*, Plaintiffs v. *Mylan Laboratories Ltd. and Sandoz, Inc.*, Defendants. Civil Action No. 19-13955 (FLW). Filed Apr. 26, 2021.
Exhibit A—Dec. 27, 2006 (Revised Feb. 2021) Statement on a Nonproprietary Name Adopted by the USAN Council: USAN Ferric Carboxymaltose.
Exhibit B—Dec. 27, 2006 (Revised Nov. 2016) Statement on a Nonproprietary Name Adopted by the USAN Council: USAN Ferric Carboxymaltose.
Exhibit C—USAN 2020 Winter Meeting minutes of the USAN Council—Meeting of Dec. 4, 2020 virtually via WebEx. Retrieved from the internet on Feb. 8, 2021 from URL https://www.ama-assn.org/about/united-states- adopted-names/usan-council.
Exhibit D—USAN Procedure for USAN Name Selection— Retrieved from the Internet on Feb. 8, 2021 from URL https://www.ama-assn.org/about/united-states-adopted-names/procedure-usan-name-selection.
Letter dated Feb. 8, 2021 from William P. Deni, Jr., Director, Gibbons P.C., Newark, NJ to the Honorable Freda L. Wolfson, C.U.S.D.J., United States District Court, District of New Jersey, RE: *Vifor (International) AG*, et al. v. *Mylan Laboratories Ltd. and Sandoz Inc.*, Civil Action No. 19-13955 (FLW) (DEA) (CONSOLIDATED).
Letter dated Mar. 10, 2021 from William P. Deni, Jr., Director, Gibbons P.C., Newark, NJ to the Honorable Freda L. Wolfson, C.U.S.D.J., United States District Court, District of New Jersey, RR: *Vifor (International) AG*, et al. v. *Mylan Laboratories Ltd. and Sandoz Inc.*, Civil Action No. 19-13955 (FLW) (DEA) (CONSOLIDATED).
Letter dated Mar. 2, 2021 from Eric I. Abraham, Hill Wallack, LLP to the Honorable Freda L. Wolfson, C.U.S.D. J., United States District Court, District of New Jersey, RE: *Vifor (International) AG*, et al. v. *Mylan Laboratories Ltd. and Sandoz Inc.*, Civil Action No. 19-13955 (FLW) (DEA) (CONSOLIDATED).
Exhibit 3—Form D—USAN Revised Application dated Oct. 29, 2020 for SS-40 Ferric Carboxymaltose.
Exhibit 2—USPTO Non-Final Office Action dated Jan. 13, 2021 issued in U.S. Appl. No. 17/087,132, filed Nov. 2, 2020.
Letter accompanying subsequently filed items. Filed in European Appl. No. 077163095 / European Patent No. EP 1973549 (Vifor (international) AG), submitted to European Patent Office dated Sep. 29, 2020, 4 pages.
Letter accompanying subsequently filed items. Filed in European Appl. No. 077163095 / European Patent No EP 1973549 (Vifor (International) AG), submitted to European Patent Office dated Sep. 28, 2020, 1 page.
Letter relating to appeal procedure. Filed in European Appl. No. 077163095 / European Patent No. EP 1973549 (Vifor (International) AG), submitted to European Patent Office dated Sep. 25, 2020, 1 page.
Reply to Appeal. Response to the communication dated May 19, 2020, forwarding the statements setting out the grounds of appeal of the opponents 03, 06, and 07. Appeal No. T1139/19-3.3.01 to Opposition in European Patent No. 1973549; Appellant: Vifor (International) AG; Respondents: Hoffmann Eitle Patent—und Rechtsanwalte, Partnerschaftsgesellschaft mbB, Pharmacosmos Holding A/S,Teva Pharmaceutical Industries LTD, HGF Limited, STADA Arzneimittel AG, Taylor Wessing LLP, Generics Limited.
Non Patent Literature cited during appeal. Appeal No. T1139/19-3.3.01. European Patent No. EP 1973549 (Vifor (International) AG). New Zealand Data Sheet—Ferrosig Solution for Injection 50 mg/mL.
Non Patent Literature cited during appeal. Appeal No. T1139/19-3.3.01. European Patent No. EP 1973549 (Vifor (International) AG). Single total dose infusion of ferumoxytol (1020 mg in 30 minutes) is an improved method of administration of intravenous iron. Correspondence. AJH. Wiley. pp. E228-E232.
Reply to the Patentee's Appeal. Appeal No. T1139/19-3.3.01; Opposition in European Patent No. 1973549 (Vifor (International) AG); Opponent:Generics [UK] Limited (07). Filed in the European Patent Office Sep. 28, 2020, 14 pages.
Reply to the Patentee's Appeal. Appeal No. T1139/19-3.3.01; Opposition in European Patent No. 1973549 (Vifor (International) AG); Opponent:Generics [UK] Limited (07). Filed in the European Patent Office Sep. 28, 2020, 15 pages.
Reply to the Patentee's Appeal. Appeal No. T1139/19-3.3.01; Opposition in European Patent No. 1973549 (Vifor (International) AG); Opponent: Teva Pharmaceutical Industries Ltd (03). Filed in the European Patent Office Sep. 17, 2020, 12 pages.
Defendant's Responsive Claim Construction Brief. In the United States District Court for the District of New Jersey. Civil Action No. 19-13955. *Vifor (International) AG* and *American Regent, Inc.*, Plaintiffs v. *Mylan Laboratories Ltd. and Sandoz, Inc.*, Defendants. Filed electronically in the Court on Sep. 28, 2020. 39 pages.
Plaintiff's Responsive Markman Brief (Redacted) in the United States District Court, District of New Jersey. Civil Action No. 19-13955. *Vifor (International) AG* and *American Regent, Inc.*, Plaintiffs v. *Mylan Laboratories Ltd. and Sandoz, Inc.*, Defendants. Dated Sep. 28, 2020. 36 pages.
Claim Construction Opinion. United States District Court—District of New Jersey. *Vifor (International) AG* and *American Regent, Inc.*, Plaintiffs, v. *Mylan Laboratories Ltd.* and *Sandoz Inc.*, Defendants. Civil Action No. 19-13955 (FLW) filed Jun. 28, 2021.
Claim Construction Order. Hon. Freda L. Wolfson. United States District Court - District of New Jersey. *Vifor (International) AG* and *American Regent, Inc.*, Plaintiffs, v. *Mylan Laboratories Ltd.* and *Sandoz Inc.*, Defendants. Civil Action No. 19-13955 (FLW) filed Jun. 28, 2021.
Opening Expert Report of Dr. Michael Auerbach, MD, FACP and Exhibit A (CV). United States District Court—District of New Jersey. *Vifor (International) AG* and *American Regent, Inc.*, Plaintiffs, v. *Mylan Laboratories Ltd.* and *Sandoz Inc.*, Defendants. Civil Action No. 19-13955 (FLW) (DEA) (Consolidated). Received May 11, 2021.
Opening Expert Report of Dr. John Glaspy Regarding Invalidity of U.S. Pat. No. 7,754,702 and 8,895,612 and Exhibit A (CV). United States District Court—District of New Jersey. *Vifor (International) AG* and *American Regent, Inc.*, Plaintiffs, v. *Mylan Laboratories Ltd.* and *Sandoz Inc.*, Defendants. Case No. 3.19-cv-13955 FLW-DEA (Consolidated). Received May 11, 2021.
Rebuttal Expert Report of Brian M. Stoltz, PhD. United States District Court - District of New Jersey. *Vifor (International) AG* and *American Regent, Inc.*, Plaintiffs, v.*Mylan Laboratories Ltd.* and *Sandoz Inc.*, Defendants. Civil Action No. 19-13955 (FLW) (DEA) (Consolidated). Received May 11, 2021.
Opening Expert Report of Daniel Hurnik, DVM, MSC. Regarding Validity of U.S. Pat. No. 7,754,702 And 8,895,612. United States District Court—District of New Jersey. *Vifor (International) AG* and *American Regent, Inc.*, Plaintiffs, v. *Mylan Laboratories Ltd.* and *Sandoz Inc.*, Defendants. Civil Action No. 19-13955 (FLW) (DEA) (Consolidated). Received May 11, 2021.
Responsive Expert Report of Christian Brueckner, Ph.D. United States District Court - District of New Jersey. *Vifor (International) AG* and *American Regent, Inc.*, Plaintiffs, v. *Mylan Laboratories Ltd.* and *Sandoz Inc.*, Defendants. Civil Action No. 19-13955 (FLW) (DEA) (Consolidated). Received May 11, 2021.
Rebuttal Expert Report of James A. Cowan, Ph. D. Regarding Validity of U.S. Pat. No. 7,612,109, 9,376,505, and 10,519,252. United States District Court—District of New Jersey. *Vifor (International) AG* and *American Regent, Inc.*, Plaintiffs, v. *Mylan Laboratories Ltd.* and *Sandoz Inc.*, Defendants. Civil Action No. 19-13955 (FLW) (DEA) (Consolidated). Received May 11, 2021.
Rebuttal Expert Report of Daniel W. Coyne, M.D., Regarding Validity of U.S. Patent Nos. 7,754,702 AND 8,895,612. United States District Court - District of New Jersey. *Vifor (International) AG* and *American Regent, Inc.*, Plaintiffs, v. *Mylan Laboratories Ltd.* and *Sandoz Inc.*, Defendants. Civil Action No. 19-13955 (FLW) (DEA) (Consolidated). Received May 11, 2021.

(56) References Cited

OTHER PUBLICATIONS

Rebuttal Expert Report of Jay B. Wish, M.D. Egarding Validity of U.S. Pat. No. 10,519,252. United States District Court—District of New Jersey. *Vifor (International) AG* and *American Regent, Inc.*, Plaintiffs, v. *Mylan Laboratories Ltd.* and *Sandoz Inc.*, Defendants. Civil Action No. 19-13955 (FLW) (DEA) (Consolidated). Received May 11, 2021.

Opening Expert Report of Paul J. Chirik, Ph.D. Regarding Iron Carbohydrate Coordination Chemistry. United States District Court - District of New Jersey. *Vifor (International) AG* and *American Regent, Inc.*, Plaintiffs, v. *Mylan Laboratories Ltd.* and *Sandoz Inc.*, Defendants. Civil Action No. 19-13955 (FLW) (DEA) (Consolidated). Received May 11, 2021.

Opening Expert Report of James E. Kipp, Ph.D. United States District Court—District of New Jersey. *Vifor (International) AG* and *American Regent, Inc.*, Plaintiffs, v. *Mylan Laboratories Ltd.* and *Sandoz Inc.*, Defendants. Case No. 3.19-cv-13955 FLW-DEA (Consolidated). Received May 11, 2021.

Expert Report of Jerome Lewis, Ph. D. United States District Court—District of New Jersey. *Vifor (International) AG* and *American Regent, Inc.*, Plaintiffs, v. *Mylan Laboratories Ltd.* and *Sandoz Inc.*, Defendants. Case No. 3.19-cv-13955 FLW-DEA (Consolidated). Received May 11, 2021.

Boruch, M. Transformations of Potato Starch During Oxidation with Hypochlorite. Starch/Starke. 1985, vol. 3, pp. 91-98.

Reply Expert Report of Dr. Michael Auerbach, Md, Facp and Exhibit A (CV). United States District Court—District of New Jersey. *Vifor (International) AG* and *American Regent, Inc.*, Plaintiffs, v. *Mylan Laboratories Ltd.* and *Sandoz Inc.*, Defendants. Civil Action No. 19-13955 (FLW) (DEA) (Consolidated). Received Aug. 3, 2021.

Reply Expert Report of Dr. John Glaspy. United States District Court—District of New Jersey. *Vifor (International) AG* and *American Regent, Inc.*, Plaintiffs, v. *Mylan Laboratories Ltd.* and *Sandoz Inc.*, Defendants. Case No. 3.19-cv-13955 FLW-DEA (Consolidated). Received Aug. 3, 2021.

Reply Expert Report of Ivan T. Hoffman. United States District Court—District of New Jersey. *Vifor (International) AG* and *American Regent, Inc.*, Plaintiffs, v. *Mylan Laboratories Ltd.* and *Sandoz Inc.*, Defendants. Case No. 3.19-cv-13955 FLW-DEA (Consolidated). Received Aug. 3, 2021.

Reply Expert Report of James E. Kipp, Ph.D. United States District Court—District of New Jersey. *Vifor (International) AG* and *American Regent, Inc.*, Plaintiffs, v. *Mylan Laboratories Ltd.* and *Sandoz Inc.*, Defendants. Case No. 3.19-cv-13955 FLW-DEA (Consolidated). Received Aug. 3, 2021.

Reply Expert Report of Jerome Lewis, Ph. D. United States District Court—District of New Jersey. *Vifor (International) AG* and *American Regent, Inc.*, Plaintiffs, v. *Mylan Laboratories Ltd.* and *Sandoz Inc.*, Defendants. Case No. 3.19-cv-13955 FLW-DEA (Consolidated). Received Aug. 3, 2021.

Letter of Supplement Approval for Injectafer—Highlights of Prescribing Information package insert. U.S. Food and Drug Administration to American Regent, Inc. U.S. Food & Drug Administration, Silver Springs, MD 20993. Received Aug. 3, 2021.

\* cited by examiner

AQUEOUS IRON CARBOHYDRATE COMPLEXES, THEIR PRODUCTION AND MEDICAMENTS CONTAINING THEM

This application is a continuation of U.S. application Ser. No. 16/389,234 filed on Apr. 19, 2019, which is a continuation of U.S. application Ser. No. 13/835,400, filed on Mar. 15, 2013, now U.S. Pat. No. 10,519,252, which is a continuation of U.S. application Ser. No. 13/556,733, filed on Jul. 24, 2012, now U.S. Pat. No. 9,376,505, which is a continuation of U.S. application Ser. No. 12/581,212, filed on Oct. 19, 2009, now abandoned, which is a divisional of U.S. application Ser. No. 10/531,895, filed on Oct. 20, 2003, now U.S. Pat. No. 7,612,109, and which is a National Stage of Application No. PCT/EP2003/011596, filed Oct. 20, 2003, which claims the benefit of German Application No. 10249552.1, filed on Oct. 23, 2002. These applications are herein incorporated by reference into the present application.

The present invention concerns water-soluble iron carbohydrate complexes which are used for the treatment of iron deficiency anemia, their preparation, medicaments containing them and their use for the prophylaxis or treatment of iron deficiency anemia. The medicaments are especially useful for parenteral application.

Iron deficiency anemia can be treated or prophylactically treated by the application of medicaments containing iron. In this respect the use of iron carbohydrate complexes is known. A water soluble iron (III) hydroxide sucrose complex is a frequently and successfully used preparation (Danielson, Salmonson, Derendorf, Geisser, Drug Res., Vol. 46: 615-621, 1996). It is also known in the art to use, for parenteral application, iron dextran complexes as well as complexes based on pullulans (WO 02/46241), which are difficult to obtain and have to be produced under pressure at high temperatures and involving hydrogenating steps. Other iron carbohydrate complexes are also known for oral application.

The problem to be solved by the present invention is to provide an iron preparation which is especially to be applied parenterally and which can easily be sterilized; the known parenterally applicable preparations on the basis of sucrose and dextran were only stable at temperatures up to 100° C., which made sterilization difficult. Further, the preparation to be provided by the invention shall have reduced toxicity and shall avoid dangerous anaphylactic shocks which can be induced by dextran. Also, the stability of the complexes of the preparation shall be high in order to enable a high applicable dosage and a high rate of application. Furthermore, the iron preparation is to be producible from easily obtainable starting products and without great effort.

In accordance with the present invention the problem can be solved by providing iron (III) carbohydrate complexes on the basis of the oxidation products of maltodextrins.

Therefore, an object of the present invention is water soluble iron carbohydrate complexes, which are obtainable from an aqueous solution of an iron (III) salt and an aqueous solution of the oxidation product of one or more maltodextrins, using an aqueous hypochlorite solution at an alkaline pH value, e.g., of 8 to 12 where, when one maltodextrin is applied, its dextrose equivalent lies between 5 and 20, and when a mixture of several maltodextrins is applied, the dextrose equivalent of the mixture lies between 5 and 20 and the dextrose equivalent of each individual maltodextrin contained in the mixture lies between 2 and 40.

A further object of the present invention is a process for producing the iron carbohydrate complexes according to the invention wherein one or more maltodextrins are oxidized in an aqueous solution at an alkaline pH value, e.g., of 8 to 12 using an aqueous hypochlorite solution and reacting the obtained solution with an aqueous solution of an iron (III) salt where, when one maltodextrin is applied, its dextrose equivalent lies between 5 and 20, and when a mixture of several maltodextrins is applied, the dextrose equivalent of the mixture lies between 5 and 20 and the dextrose equivalent of each individual maltodextrin contained in the mixture lies between 2 and 40.

The usable maltodextrins are easily obtainable starting products, and they are commercially available.

In order to prepare the ligands of the complexes of the invention, the maltodextrins are oxidized in an aqueous solution with a hypochlorite solution. Suitable examples are solutions of alkali hypochlorites such as a solution of sodium hypochlorite. Commercially available solutions can be used. The concentration of the hypochlorite solution, e.g., is at least 13% by weight, preferably on the order of 13 to 16% by weight, calculated as active chlorine. Preferably the solutions are used in such an amount that about 80 to 100%, preferably about 90%, of one aldehyde group per molecule of maltodextrin is oxidized. In this manner, the reactivity caused by the glucose content of the maltodextrin molecules is lowered to 20% or less, preferably to 10% or less.

The oxidation is carried out in an alkaline solution, e.g., at a pH of 8 to 12, for example 9 to 11. As an example, oxidation can be carried out at temperatures on the order of 15 to 40° C., preferably of 25 to 35° C. The reaction times are, e.g, on the order of 10 minutes to 4 hours, e.g., 1 to 1.5 hours.

By this procedure the degree of depolymerization of the starting maltodextrins is kept at a minimum. Only theoretically it is assumed that the oxidation occurs mainly at the terminal aldehyde group (acetal or semiacetal group, respectively) of the maltodextrin molecules.

It is also possible to catalyze the oxidation reaction of the maltodextrins. The addition of bromide ions is suitable, e.g., in the form of alkali bromides, for example sodium bromide. The added amount of bromide is not critical. The amount is kept as low as possible in order to achieve an end product (Fe-complex) which can easily be purified. Catalytic amounts are sufficient. As stated above, the addition of bromide is possible, however, not necessary.

Further, it is also possible to use other oxidation systems, such as, e.g., the known ternary oxidation system hypochlorite/alkali bromide/2,2,6,6-tetramethylpiperidine-1-oxyl (TEMPO) for the oxidation of the maltodextrins. The process to oxidize maltodextrins catalytically with alkali bromides or with the ternary TEMPO system is described, e.g., by Thaburet et al, in Carbohydrate Research 330 (2001) 21-29, which method can be used for the present invention.

In order to prepare the complexes of the invention, the obtained oxidized maltodextrins are reacted with an iron (III) salt in an aqueous solution. In order to do so, the oxidized maltodextrins can be isolated and redissolved. It is also possible, however, to use the obtained aqueous solutions of the oxidized maltodextrins directly for the further reaction with the aqueous iron (III) solutions.

Water soluble salts of inorganic or organic acids, or mixtures thereof, such as halides, e.g., chloride and bromide, or sulfates can be used as iron (III) salts. It is preferred to use physiologically acceptable salts. It is especially preferred to use an aqueous solution of iron (III) chloride.

It has been found that the presence of chloride ions favors the formation of the complexes. The chloride ions can be used in the form of water soluble chlorides such as alkali metal chlorides, e.g., sodium chloride, potassium chloride or ammonium chloride. As stated, the iron (III) is preferably used in the form of the chloride.

For instance, the aqueous solution of the oxidized maltodextrin can be mixed with an aqueous solution of the iron (III) salt in order to carry out the reaction. Here, it is preferred to proceed in a manner so that during and immediately after mixing the oxidized maltodextrin and the iron (III) salt, the pH is strongly acid or so low that no hydrolysis of the iron (III) salt occurs, e.g., pH 2 or less, in order to avoid an undesired precipitation of iron hydroxides. In general, it is not necessary to add an acid, if iron (III) chloride is used, since aqueous solutions of iron (III) chloride can be sufficiently acidic. Only after mixing, the pH is raised to values, e.g., on the order of at least 5, for example, up to 11, 12, 13 or 14. The pH is preferably raised slowly or gradually which, for example, can be achieved by first adding a weak base, for example, up to a pH of about 3, and then neutralizing further using a stronger base. Examples of weak bases are alkali—or alkaline earth—carbonates, bicarbonates, such as sodium and potassium carbonate or bicarbonate, or ammonia. Examples of strong bases are alkali—or alkaline earth—hydroxides such as sodium, potassium, calcium or magnesium hydroxide.

The reaction can be improved by heating. For example, temperatures on the order of 15° C. up to boiling point can be used. It is preferred to raise the temperature gradually. Thus, for example, it is possible to heat to about 15 to 70° C. and then raise the temperature gradually up to boiling point.

The reaction times are, for example, on the order of 15 minutes up to several hours, e.g., 20 minutes to 4 hours, such as 25 to 70 minutes, e.g., 30 to 60 minutes.

The reaction can be carried out in a weakly acid range, for example, at a pH on the order of 5 to 6. However, it has been found, that it is useful, but not necessary, to raise the pH during the formation of the complexes to higher values of up to 11, 12, 13 or 14. In order to complete the reaction, the pH can be lowered then by addition of an acid, for example, to the order of 5 to 6. It is possible to use inorganic or organic acids or a mixture thereof, especially hydrogen halide acids such as hydrogen chloride or aqueous hydrochloric acid, respectively.

As stated above, the formation of the complexes is usually improved by heating. Thus, at the preferred embodiment of the invention, wherein the pH is raised during the reaction to ranges of at least 5 and above, up to 11 or 14, it is, for instance, possible to work at first at lower temperatures on the order of 15 to 70° C., such as 40 to 60° C., e.g., about 50° C., whereafter the pH is reduced to values on the order of at least 5, and the temperature is gradually raised over 50° C. up to boiling point The reaction times are on the order of 15 minutes up to several hours and they can vary depending on the reaction temperature. If the process is carried out with an intermediate pH of more than 5, it is, for example, possible to work 15 to 70 minutes, e.g., 30 to 60 minutes, at the enhanced pH, for example, at temperatures of up to 70° C., whereafter the pH is lowered to a range on the order of at least 5 and the reaction is carried out for a further 15 to 70 minutes, e.g., 30 to 60 minutes, at temperatures, e.g., up to 70° C., and optionally a further 15 to 70 minutes, e.g., 30 to 60 minutes, at higher temperatures up to boiling point.

After the reaction the obtained solution can be cooled, e.g., to room temperature and can optionally be diluted and optionally be filtered. After cooling, the pH can be adjusted to the neutral point or a little below, for example, to values of 5 to 7, by the addition of an acid or base. It is possible to use, e.g., the acids and bases which have been mentioned for carrying out the reaction. The solutions obtained are purified and can directly be used for the production of medicaments. However, it is also possible to isolate the iron (III) complexes from the solution, e.g., by precipitation with an alcohol such as an alkanol, for example, ethanol. Isolation can also be effected by spray-drying. Purification can take place in the usual way, especially in order to remove salts. This can, for example, be carried out by reverse osmosis. It is, for example, possible to carry out the reverse osmosis before spray-drying or before a direct application in medicaments.

The iron content of the obtained iron (III) carbohydrate complexes is, for example, 10 to 40% weight/weight, especially, 20 to 35% weight/weight. They can easily be dissolved in water. It is possible to prepare neutral aqueous solutions which, e.g., have an iron content of 1% weight/vol. to 20% weight/vol. Such solutions can be sterilized thermically. The weight average molecular weight of the obtained complexes, is, for example, 80 kDa to 400 kDa, preferably 80 kDa to 350 kDa, especially preferred up to 300 kDa (measured by gel permeation chromatography, e.g., as described by Geisser et al, in Arzneim. Forsch/Drug Res. 42(11), 12, 1439-1452 (1992), paragraph 2.2.5).

As stated above, it is possible to provide aqueous solutions from the complexes of the invention. These solutions are especially useful for parenteral application. However, it is also possible to apply them orally or topically. Contrary to the known parenterally applicable iron preparations, they can be sterilized at high temperatures, e.g., at 121° C. and above, at short contact times of, e.g., 15 minutes, by acquiring $F_0 \geq 15$. The contact times are correspondingly shorter at higher temperatures. Preparations hitherto known had to be sterilely filtrated and mixed with preservatives, such as benzyl alcohol or phenol. Such additives are not necessary in the invention. Hence, it is possible to fill the solutions of the complexes, for example, into ampoules. It is, for example, possible to fill solutions having a content of 1 to 20% by weight, e.g., 5% by weight, into vessels such as ampoules or phials, e.g., of 2 to 100 ml, e.g., up to 50 ml. The preparation of the parenterally applicable solutions can be carried out as known in the art, optionally using additives which are normally used for parenteral solutions. The solutions can be formulated in such a way that they can be administered by injection or in the form of an infusion, e.g., in brine solution. For the oral or topical application it is possible to formulate preparations with usual excipients and additives.

Thus, a further object of the invention is aqueous medicaments which are especially useful for the parenteral, intravenous but also intramuscular application, as well as for oral or topical application. The aqueous medicaments are especially useful for the treatment of iron deficiency anemia. A further object of the invention is also the use of the iron (III) carbohydrate complexes according to the invention for the treatment and prophylaxis of iron deficiency anemia or the production of medicaments especially for the parenteral treatment of iron deficiency anemia. The medicaments can be used in human and veterinary medicine.

The advantages which are achieved with the iron (III) carbohydrate complexes of the invention are the above-mentioned high sterilization temperatures, as well as the low toxicity and the reduced danger of anaphylactic shock. The toxicity of the complexes according to the invention is very low. The $LD_{50}$ lies at over 2000 mg Fe/kg, compared to the $LD_{50}$ of the known pullulan complexes, which lies at 1400 mg Fe/kg. In view of the high stability of the complexes of the invention, it is possible to enhance the rates of application as well as the dosages. Thus, it is possible to apply the medicaments of the invention parenterally in the form of a single dose. Such a single dose is, for example, 500 to 1000 mg iron. The dose can be applied, for example, during the course of one hour. A further advantage lies in the high degree of availability of the maltodextrins used as starting products, which are, e.g., commercially available additives in the food processing industry.

In the present description, as well as in the following examples, the dextrose equivalents are measured gravimetrically. In order to do so, the maltodextrins are reacted in a boiling aqueous solution with Fehling's solution. The reaction is carried out quantitatively, i.e. until the Fehling's solution is no longer discolored. The precipitated copper (I) oxide is dried at 105° C. until a constant weight is achieved and measured gravimetrically. The glucose content (dextrose equivalent) is calculated from the obtained results as % weight/weight of the maltodextrin dry substance. It is, for example, possible to use the following solutions: 25 ml Fehling's solution I, mixed with 25 ml Fehling's solution II; 10 ml aqueous maltodextrin solution (10% mol/vol) (Fehling's solution I: 34.6 g copper (II) sulfate dissolved in 500 ml water; Fehling's solution II: 173 g potassium sodium tartrate and 50 g sodium hydroxide dissolved in 400 ml water).

EXAMPLE 1

100 g maltodextrin (9.6 dextrose equivalent measured gravimetrically) are dissolved by stirring in 300 ml water at 25° C. and oxidized by addition of 30 g sodium hypochlorite solution (13 to 16 weight percent active chlorine) at pH 10.

At first, the oxidized maltodextrin solution and then 554 g sodium carbonate solution (17.3% weight/weight) are added at room temperature to 352 g of a stirred iron (III) chloride solution (12% weight by weight Fe).

Then, the pH is adjusted to 11 by addition of sodium hydroxide, and the solution is heated to 50° C. and kept at 50° C. for 30 minutes. Then, acidification to a pH of 5 to 6 is effected by addition of hydrochloric acid, the solution is kept at 50° C. for a further 30 minutes and then heated to 97-98° C., and the temperature is kept for 30 minutes at this range. After cooling the solution to room temperature, the pH is adjusted to 6-7 by the addition of sodium hydroxide.

The solution is then filtered through a sterilization filter and then examined for sediments. Thereafter, the complex is isolated by precipitation with ethanol in a range of 1:0.85, and then dried in vacuum at 50° C.

The yield is 125 g (corresponding to 87% of the theoretical value) of a brown amorphic powder having an iron content of 29.3% weight/weight (measured complexometrically).

Molecular weight mw 271 kDa.

EXAMPLE 2

200 g maltodextrin (9.6 dextrose equivalent measured gravimetrically) are dissolved by stirring in 300 ml water at 25° C. and oxidized by addition of 30 g sodium hypochlorite solution (13 to 16 weight percent active chlorine) at pH 10.

At first, the oxidized maltodextrin solution and then 554 g sodium carbonate solution (17.3% weight/weight) are added at room temperature to 352 g of a stirred iron (III) chloride solution (12% weight by weight Fe).

Then, the pH is adjusted to 11 by addition of sodium hydroxide, and the solution is heated to 50° C. and kept for 30 minutes at 50° C. Then, acidification to a pH of 5 to 6 is effected by addition of hydrochloric acid, the solution is kept at 50° C. for a further 30 minutes and then heated to 97-98° C., and the temperature Is kept for 30 minutes at this range. After cooling the solution to room temperature, the pH is adjusted to 6-7 by the addition of sodium hydroxide.

The solution is then filtered through a sterilization filter and then examined for sediments. Thereafter, the complex is isolated by precipitation with ethanol in a range of 1:0.85, and then dried in vacuum at 50° C.

The yield is 123 g (corresponding to 65% of the theoretical value) of a brown amorphic powder having an iron content of 22.5% weight/weight (measured complexometrically).

Molecular weight mw 141 kDa,

EXAMPLE 3

100 g maltodextrin (9.6 dextrose equivalent measured gravimetrically) are dissolved by stirring in 300 ml water at 25° C. and oxidized by addition of 30 g sodium hypochlorite solution (13 to 16 weight percent active chlorine) and 0.7 g sodium bromide at pH 10.

At first, the oxidized maltodextrin solution and then 554 g sodium carbonate solution (17.3% weight/weight) are added at room temperature to 352 g of a stirred iron (III) chloride solution (12% weight by weight Fe).

Then, the pH is adjusted to 6.5 by addition of sodium hydroxide and the solution is heated to 50° C. and kept for 60 minutes at 50° C. Then, acidification to a pH of 5 to 6 is effected by addition of hydrochloric acid, the solution is kept at 50° C. for a further 30 minutes and then heated to 97-98° C., and the temperature is kept for 30 minutes at this range. After cooling the solution to room temperature the pH is adjusted to 6-7 by the addition of sodium hydroxide.

The solution is then filtered through a sterilization filter and then examined for sediments. Thereafter, the complex is isolated by precipitation with ethanol in a range of 1:0.85 and then dried in vacuum at 50° C.

The yield is 139 g. (corresponding to 88% of the theoretical value) of a brown amorphic powder having an iron content of 26.8% weight/weight (measured complexometrically).

Molecular weight mw 140 kDa.

EXAMPLE 4

A mixture of 45 g maltodextrin (6.6 dextrose equivalent measured gravimetrically) and 45 g maltodextrin (14.0 dextrose equivalent measured gravimetrically) is dissolved by stirring in 300 ml water at 25° C. and oxidized by addition of 25 g sodium hypochlorite solution (13 to 16 weight percent active chlorine) and 0.6 g sodium bromide at pH 10.

At first, the oxidized maltodextrin solution and then 554 g sodium carbonate solution (17.3% weight/weight) are added at room temperature to 352 g of a stirred iron (III) chloride solution (12% weight by weight Fe).

Then, the pH is adjusted to 11 by addition of sodium hydroxide and the solution is heated to 50° C. and kept for 30 minutes at 50° C. Then, acidification to a pH of 5 to 6 is effected by addition of hydrochloric acid, the solution is kept at 50° C. for a further 30 minutes and then heated to 97-98° C., and the temperature is kept for 30 minutes at this range. After cooling the solution to room temperature the pH is adjusted to 6-7 by the addition of sodium hydroxide.

The solution is then filtered through a sterilization filter and then examined for sediments. Thereafter, the complex is isolated by precipitation with ethanol in a range of 1:0.85 and then dried in vacuum at 50° C.

The yield is 143 g (corresponding to 90% of the theoretical value) of a brown amorphous powder having an iron content of 26.5% weight/weight (measured complexometrically).

Molecular weight mw 189 kDa.

EXAMPLE 5

90 g maltodextrin (14.0 dextrose equivalent measured gravimetrically) are dissolved by stirring in 300 ml water at 25° C. and oxidized by addition of 35 g sodium hypochlorite solution (13 to 16 weight percent active chlorine) and 0.6 g sodium bromide at pH 10.

At first, the oxidized maltodextrin solution and then 554 g sodium carbonate solution (17.3% weight/weight) are added at room temperature to 352 g of a stirred iron (III) chloride solution (12% weight by weight Fe).

Then, the pH is adjusted to 11 by addition of sodium hydroxide and the solution is heated to 50° C. and kept for 30 minutes at 50° C. Then, acidification to a pH of 5 to 6 is effected by addition of hydrochloric acid, the solution is kept at 50° C. for a further 30 minutes and then heated to 97-98° C. and the temperature is kept for 30 minutes at this range. After cooling the solution to room temperature the pH is adjusted to 6-7 by the addition of sodium hydroxide.

The solution is then filtered through a sterilization filter and then examined for sediments. Thereafter, the complex is isolated by precipitation with ethanol in a range of 1:0.85 and then dried in vacuum at 50° C.

The yield is 131 g (corresponding to 93% of the theoretical value) of a brown amorphous powder having an iron content of 29.9% weight/weight (measured complexometrically).

Molecular weight mw 118 kDa.

EXAMPLE 6

A mixture of 45 g maltodextrin (5.4 dextrose equivalent measured gravimetrically) and 45 g maltodextrin (18.1 dextrose equivalent measured gravimetrically) is dissolved by stirring in 300 ml water at 25° C. and oxidized by addition of 31 g sodium hypochlorite solution (13 to 16 weight percent active chlorine) and 0.7 g sodium bromide at pH 10.

At first, the oxidized maltodextrin solution and then 554 g sodium carbonate solution (17.3% weight/weight) are added at room temperature to 352 g of a stirred iron (III) chloride solution (12% weight by weight Fe).

Then, the pH is adjusted to 11 by addition of sodium hydroxide and the solution is heated to 50° C. and kept for 30 minutes at 50° C. Then, acidification to a pH of 5 to 6 is effected by addition of hydrochloric acid, the solution is kept at 50° C. for a further 30 minutes and then heated to 97-98° C. and the temperature is kept for 30 minutes at this range. After cooling the solution to room temperature the pH is adjusted to 6-7 by the addition of sodium hydroxide.

The solution is then filtered through a sterilization filter and then examined for sediments. Thereafter, the complex is isolated by precipitation with ethanol in a range of 1:0.85 and then dried in vacuum at 50° C.

The yield is 134 g (corresponding to 88% of the theoretical value) of a brown amorphous powder having an iron content of 27.9% weight/weight (measured complexometrically).

Molecular weight mw 178 kDa.

EXAMPLE 7

100 g maltodextrin (9.6 dextrose equivalent measured gravimetrically) are dissolved by stirring in 300 ml water at 25° C. and oxidized by addition of 29 g sodium hypochlorite solution (13 to 16 weight percent active chlorine) and 0.7 g sodium bromide at pH 10.

At first, the oxidized maltodextrin solution and then 554 g sodium carbonate solution (17.3% weight/weight) are added at room temperature to 352 g of a stirred iron (III) chloride solution (12% weight by weight Fe).

Then, the pH is adjusted to 11 by addition of sodium hydroxide and the solution is heated to 50° C. and kept for 30 minutes at 50° C. Then, acidification to a pH of 5 to 6 is effected by addition of hydrochloric acid, the solution is kept at 50° C. for a further 70 minutes. After cooling the solution to room temperature the pH is adjusted to 6-7 by the addition of sodium hydroxide.

The solution is then filtered through a sterilization filter and then examined for sediments. Thereafter, the complex is isolated by precipitation with ethanol in a range of 1:0.85 and then dried in vacuum at 50° C.

The yield is 155 g (corresponding to 90% of the theoretical value) of a brown amorphous powder having an iron content of 24.5% weight/weight (measured complexometrically).

Molecular weight mw 137 kDa.

EXAMPLE 8

126 g maltodextrin (6.6 dextrose equivalent measured gravimetrically) are dissolved by stirring in 300 ml water at 25° C. and oxidized by addition of 24 g sodium hypochlorite solution. (13 to 16 weight percent active chlorine) and 0.7 g sodium bromide at pH 10.

At first, the oxidized maltodextrin solution and then 554 g sodium carbonate solution (17.3% weight/weight) are added at room temperature to 352 g of a stirred iron (III) chloride solution (12% weight by weight Fe).

Then, the pH is adjusted to 11 by addition of sodium hydroxide and the solution is heated to 50° C. and kept for 30 minutes at 50° C. Then, acidification to a pH of 5 to 6 is effected by addition of hydrochloric acid, the solution is kept at 50° C. for a further 70 minutes. After cooling the solution to room temperature the pH is adjusted to 6-7 by the addition of sodium hydroxide.

The solution is then filtered through a sterilization filter and then examined for sediments. Thereafter, the complex is isolated by precipitation with ethanol in a range of 1:0.85 and then dried in vacuum at 50° C.

The yield is 171 g (corresponding to 86% of the theoretical value) of a brown amorphous powder having an iron content of 21.35% weight/weight (measured complexometrically).

Molecular weight mw 170 kDa.

Comparative Test

In the following, the characteristics of the iron carbohydrate complexes are compared with a commercially available iron sucrose complex. It can be seen that the iron content can be enhanced, the thermal treatment can be carried out at higher temperatures and the toxicity ($LD_{50}$) can be lowered in accordance with the invention.

|  | According to the invention | Iron hydroxide/ sucrose complex |
| --- | --- | --- |
| Fe content [%] | 5.0 | 2.0 |
| pH | 5-7 | 10.5-11.0 |
| mw [kDa][1] | 80-350 | 34-54 |
| Thermal treatment | 121° C./15' | 100° C./35' |
| $LD_{50}$ i.v., w.m. [mg Fe/kg body weight] | >2000 | >200 |

The invention claimed is:

1. An iron (III) carboxymaltodextrin complex which has a weight average molecular weight in the range of from 118 kDa to 271 kDa as measured by gel permeation chromatography, and is obtained from the oxidation of maltodextrin, wherein when one maltodextrin is present its dextrose equivalent lies between 5 and 20, and when a mixture of several maltodextrins is present, the dextrose equivalent of the mixture lies between 5 and 20 and the dextrose equivalent of each individual maltodextrin contained in the mixture lies between 2 and 40, and iron is present in an amount ranging from 20% to 35% by weight, relative to said iron (III) carboxymaltodextrin complex measured complexometrically.

2. The iron (III) carboxymaltodextrin complex of claim 1, wherein the oxidized maltodextrin is obtained by oxidation of maltodextrin in an aqueous hypochlorite solution.

3. The iron (III) carboxymaltodextrin complex of claim 1, wherein from about 80% to about 100% of an aldehyde group per molecule of maltodextrin is oxidized.

4. The iron (III) carboxymaltodextrin complex of claim 1, wherein from about 90% to about 100% of an aldehyde group per molecule of maltodextrin is oxidized.

5. The iron (III) carboxymaltodextrin complex of claim 2, wherein a concentration of the hypochlorite solution is from 13% to 16% by weight, calculated as active chlorine.

6. A medicament comprising the iron (III) carboxymaltodextrin complex of claim 1 and at least one pharmaceutically acceptable carrier, excipient, or additive, wherein said medicament is an aqueous solution of said iron (III) carboxymaltodextrin complex.

7. The medicament comprising the iron (III) carboxymaltodextrin complex of claim 6, wherein said iron (III) carboxymaltodextrin complex is present in said aqueous solution in an amount of from 1% to 20% by weight, based on a total weight of the aqueous solution.

8. The medicament comprising the iron (III) carboxymaltodextrin complex of claim 6, wherein the oxidized maltodextrin is obtained by oxidation of maltodextrin in an aqueous hypochlorite solution.

9. The medicament comprising the iron (III) carboxymaltodextrin complex of claim 6, wherein from about 80% to about 100% of an aldehyde group per molecule of maltodextrin is oxidized.

10. The medicament comprising the iron (III) carboxymaltodextrin complex of claim 6, wherein from about 90% to about 100% of an aldehyde group per molecule of maltodextrin is oxidized.

11. The medicament comprising the iron (III) carboxymaltodextrin complex of claim 8, wherein a concentration of the hypochlorite solution is from 13% to 16% by weight, calculated as active chlorine.

12. The medicament comprising the iron (III) carboxymaltodextrin complex of claim 8, wherein said iron (III) carboxymaltodextrin complex is present in said aqueous solution in an amount of from 1% to 20% by weight, based on a total weight of the aqueous solution.

13. The medicament comprising the iron (III) carboxymaltodextrin complex of claim 6, wherein the aqueous solution has been sterilized at a temperature of 121° C. and above.

14. The medicament of claim 6, wherein the aqueous solution has been sterilized at a temperature of 121° C. and above at a contact time of 15 minutes.

15. The medicament of claim 7, wherein the aqueous solution has been sterilized (i) at a temperature of 121° C. at a contact time of 15 minutes; or (ii) at a temperature of above 121° C. at a contact time of 15 minutes.

16. The medicament of claim 8, wherein the aqueous solution has been sterilized at a temperature of 121° C. and above.

17. The medicament of claim 8, wherein the aqueous solution has been sterilized at a temperature of 121° C. and above at a contact time of 15 minutes.

18. The medicament of claim 9, wherein the aqueous solution has been sterilized at a temperature of 121° C. and above.

19. The medicament of claim 10, wherein the aqueous solution has been sterilized (i) at a temperature of 121° C. at a contact time of 15 minutes or less; or (ii) at a temperature of 121° C. and above at a contact time of 15 minutes.

20. The medicament of claim 13 for parenteral administration to a subject in need thereof in the form of a single dose of 500 mg to 1000 mg of iron.

21. The medicament of claim 6, wherein the iron (III) carboxymaltodextrin complex has a weight average molecular weight of from about 118 kDa to about 189 kDa.

22. The medicament of claim 6 for parenteral administration to a subject in need thereof in the form of a single dose of 500 mg to 1000 mg of iron.

23. The medicament of claim 18 for parenteral administration to a subject in need thereof in the form of a single dose of 500 mg to 1000 mg of iron.

24. The medicament of claim 6, wherein the iron (III) carboxymaltodextrin complex has a weight average molecular weight of: about 141,000 Da, or about 140,000 Da, or about 189,000 Da, or about 178,000 Da, or about 137,000 Da, or about 170,000 Da.

25. The medicament of claim 12, wherein the iron (III) carboxymaltodextrin complex has a weight average molecular weight of: about 141,000 Da, or about 140,000 Da, or about 189,000 Da, or about 178,000 Da, or about 137,000 Da, or about 170,000 Da.

26. The medicament of claim 18, wherein the iron (III) carboxymaltodextrin complex has a weight average molecular weight of: about 141,000 Da, or about 140,000 Da, or about 189,000 Da, or about 178,000 Da, or about 137,000 Da, or about 170,000 Da.

27. A method for treating an iron deficiency condition in a subject in need thereof, the method comprising administering to the subject in need thereof a pharmaceutically effective amount of a medicament of claim 6, wherein the iron deficiency condition is anemia.

28. The method of claim 27, wherein said medicament is administered (i) intravenously; (ii) by injection; or (iii) by infusion.

29. A method for treating an iron deficiency condition in a subject in need thereof, the method comprising administering to the subject in need thereof a pharmaceutically effective amount of a medicament of claim 22, wherein the iron deficiency condition is anemia and wherein said medicament is administered (i) intravenously; (ii) by injection; or (iii) by infusion.

* * * * *